(12) United States Patent
Jean-Claude et al.

(10) Patent No.: US 7,879,861 B2
(45) Date of Patent: Feb. 1, 2011

(54) COMBI-MOLECULES HAVING EGFR AND DNA TARGETING PROPERTIES

(76) Inventors: Bertrand Jean-Claude, 18473 Poitiers Street, Pierrefonds, Québec (CA) H9K 1P8; Zakaria Rachid, 2560 Mayfield Street, Apt. 33, Montréal, Québec (CA) H4B 2C8; Fouad Brahimi, 5052 Brazier Street, St-Leonard, Québec (CA) H1R 1G6

( * ) Notice: Subject to any disclaimer, the term of this patent is extended or adjusted under 35 U.S.C. 154(b) by 985 days.

(21) Appl. No.: 11/151,959

(22) Filed: Jun. 14, 2005

(65) Prior Publication Data

US 2006/0003970 A1 Jan. 5, 2006

(51) Int. Cl.
*A61K 31/517* (2006.01)
*A61K 31/519* (2006.01)
*C07D 239/72* (2006.01)
(52) U.S. Cl. .................. 514/258.1; 514/259.1; 544/293
(58) Field of Classification Search ................ 514/258, 514/259, 258.1, 259.1; 544/293
See application file for complete search history.

(56) References Cited

U.S. PATENT DOCUMENTS 5,475,001 A * 12/1995 Barker ........................ 514/183

OTHER PUBLICATIONS

Neal DE, March C, Bennett MK, Abel PD, Hall RR, Sainbury JR, Harris AL; Epidermal-growth-factor receptors in human bladder cancer: comparison of invasive and superficial tumours. *The Lancet*, Feb. 16, 1985; 366-368.
Gross ME, Zorbas MA, Danels YJ, Garcia R, Gallick GE, Olive M, Brattain MG, Boman BM, Yeoman LC; Cellular growth response to epidermal growth factor in colon carcinoma cells with an amplified epidermal growth factor receptor derived from a familial adenomatous polyposis patient. *Cancer Research* 1991; 51: 1452-1459.
Damstrup L, Rygaard K, Spang-Thomsen M, Poulsen HS; Expression of the epidermal growth factor receptor in human small cell lung cancer cell lines. *Cancer Research* 1992; 52: 3089-3093.
Koenders PG, Beex LV, Guerts-Moespat A, Heuvel JJ, Kienhuis CB, Benraad TJ; Epidermal growth factor receptor-negative tumors are predominantly confined to the subgroup of estradiol receptor-positive human primary breast cancers. *Cancer Research* 1991; 51: 4544-4548.

Slamon DJ, Godolphin W, Jones LA, Holt JA, Wong SG, Keith DE, Levin WJ, Stuart SG, Udove J, Ullrich A, Press MF; Studies of the HER-2/neu proto-oncogene in human breast and ovarian cancer. *Science: New Series* 1989; vol. 244: 707-712.
Carraway KL, Cantely LC (1994); A neu acquaintance for ErbB3 and ErbB4: a role for receptor heterodimerization in growth signaling. *Cell*, 1994; vol. 78: 5-8.
Stebbing J, Copson E, O'Reilly S; Herceptin (trastuzamab) in advanced breast cancer. *Cancer Treatment Reviews* 2000; 26: 287-290.
Ciardiello F, Caputo R, Bianco R, Damiano V, Pomatico G, De Placido S, Bianco AR, Tortora G; Antitumor effect and potentiation of cytotoxic drugs activity in human cancer cells by ZD-1839 (Iressa), an epidermal growth factor receptor- selective tyrosine kinase inhibitor. *Clinical Cancer Research* 2000; vol. 6: 2053-2063.
Rewcastle GW, Denny WA, Bridges AJ, Zhou H, Cody DR, McMichael A, Fry DW; Tyrosine kinase inhibitors. 5. Synthesis and structure-activity relationships for 4 [(*phenylmethyl*)*amino*]-and 4-(phenylamino)quinazolines as potent adenosine 5'-triphosphate binding site inhibitors of the tyrosine kinase domain of the epidermal growth factor receptor. *J. Med Chem.* 1995; 38:3482-3487.
Rewcastle GW, Bridges AJ, Fry DW, Rubin JR, Denny WA; Tyrosine kinase inhibitors. 12. Synthesis and structure-activity relationships for 6-substituted 4-(phenylamino)pyrimido[5,4-d]pyrimidines designed as inhibitors of the epidermal growth factor receptor. *J. Med Chem.* 1997; 40:1820-1826.
Rewcastle GW, Murray DK, Elliot WL, Fry DW, Howard CT, Nelson J.M, Roberts BJ, Vincent PW, Showalter HD, Winters TR, Denny WA; Tyrosine kinase inhibitors.14. Structure-activity relationships for methylamino-substituted derivatives of 4-[(3-bromophenyl)amino]-6-(methylamino)-pyrido[3,4-d]pyrimidine (PD 158780), a potent and specific inhibitor of the tyrosine kinase activity of receptors for the EGF family growth factors. *J. Med. Chem.* 1998;41: 742-751.
Fry DW; Inhibition of the epidermal growth factor receptor family of tyrosine kinases as an approach to cancer chemotherapy: progression from reversible to irreversible inhibitors. *Pharmacol. Ther*. 1999, vol. 82: 207-218.

(Continued)

*Primary Examiner*—James O Wilson
*Assistant Examiner*—Ebenezer Sackey
(74) *Attorney, Agent, or Firm*—Choate, Hall & Stewart LLP; Charles E. Lyon; John P. Rearick

(57) ABSTRACT

A series of new chemical agents that demonstrate anti-tumor activity are described. The new chemical agents combine two major mechanisms of anti-tumor action. In an embodiment, the agents are capable of both inhibiting EGFR and damaging DNA while also, upon degradation, degrading to an inhibitor of EGFR and to an agent capable of damaging DNA. Moreover, a novel series of molecules capable of releasing two moles of EGFR inhibitor and a potent bi-functional alkylating agent are also described.

6 Claims, 24 Drawing Sheets

OTHER PUBLICATIONS

Fry DW, Bridges AJ, Denny WA, Doherty A, Greis KD, Hicks JL, Hook KE, Keller PR, Leopold WR, Loo JA; Specific, irreversible inactivation of the epidermal growth factor receptor and erbB2, by a new class of tyrosine kinase inhibitor. *Proc. Natl. Acad. Science.* 1998; vol. 95: 12022-12027.

Smaill JB, Rewcastle GW, Loo JA, Greis KD, Chan OH, Reyner EL, Lipka L, Showalter HD, Vincent PW, Elliott WL; Tyrosine kinase inhibitors. 17. Irreversible inhibitors of the epidermal growth factor receptor: 4-(phenylamino)quinazoline and 4-(phenylamino)pyrido[3,2- d]pyrimidine-6-acrylaminde bearing additional solubilizing functions. *J. Med. Chem.* 2000; 43: 1380-1397.

Discafani, CM, Carroll, M, Floyd, MB, Hollander, J; Irreversible inhibition of epidermal growth factor tyrosine kinase with in vitro activity by N-[4-[(3-bromophenylamino]-6-quinazolinyl]-2-butynamide (CL-397,785). *Biochemical Pharmacology* 1999, vol. 57, 917-925.

Tsou, HR, Mamuya, N; 6-substituted-4-(3-bromophenylamino)quinazolines as putative irreversible inhibitors of the epidermal growth factor receptor (EGFR) and human epidermal growth factor receptor (HER-2) Tyrosine kinase with enhanced antitumor activity. *J. Med. Chem.* 2001; 44, 2719-2734.

Sirotnak FM, Zakowski MF, Miller VA, Scher HI, Kris MG; Efficacy of cytotoxic agents against human tumor *xenografts* is markedly enhanced by coadministration of ZD1839 (Iressa), an inhibitor of EGFR tyrosine kinase. *Clinical Cancer Research* 2000; vol. 6: 4885-4892.

Sirotnak FM, She Y, Lee F, Chen J, Scher HI; Studies with CWR22 xenografts in nude mice suggest that ZD1839 may have a role in the treatment of both androgen-dependent and androgen-independent human prostate cancer. *Clinical Cancer Research* 2002; vol. 8: 3870-3876.

Brahimi F, Matheson SL, McNamee JP, Tari A, Jean-Claude, BJ; Inhibition of epidermal growth factor receptor-mediated signaling by "combi-triazene" BJ2000, a new probe for the Combi-Targeting postulates. *The Journal of Pharmacology and Experimental Therapeutics* 2002; vol. 303: 238-246.

Matheson SL, McNamee JP, Jean-Claude BJ; Design of a chimeric 3-methyl-1,2,3-triazene with mixed receptor tyrosine kinase and DNA damaging properties: a novel tumor targeting strategy. *The Journal of Pharmacology and Experimental Therapeutics* 2001; vol. 296: 832-840.

Qiu Q, Dudouit F, Matheson SL, Brahimi F, Banerjee R, Mcnamee JP, Jean-Claude BJ; The combi-targeting concept: a novel 3,3-disubstitued nitrosourea with EGFR tyrosine kinase inhibitory properties. *Cancer Chemother Pharmacol* 2003; 51: 1-10.

Rachid Z, Brahimi F, Teoh N, Katsoulas A, Jean-Claude BJ; The combi-targeting concept: Chemical Dissection of the dual targeting properties of a series of "combi-triazenes". *J. Med. Chem.* 2003, 46: 4313-4321.

Tari and Lopez-Berestein G; Serum predominantly activates MAPK and *Akt* kinases in EGFR-and ErbB2-over-expressing cells, respectively. *Int. J. Cancer*: 2000; 86: 295-297.

Skehan P, Storeng R, Scudiero D, Monks A, McMahon J, Vistica D, Warren JT, Bokesch H, Kenney S, Boyd MR; New colorimetric cytotoxicity assay for anti cancer-drug screening. *Journal of National Cancer Institute* 1990; 82: 1107-1112.

Martin SJ, Finucane DM, Amarante-Mendes GP, O'Brien GA, Green DR; Phosphatidylserine externalization during CD95-induced apoptosis of cells and cytoplasts requires ICE/CED-3 protease activity. *The Journal of Biological. Chemistry* 1996; vol. 271:28753-6.

Davis RJ; The mitogen-activated protein kinase signal transduction pathway. *The Journal of Biological Chemistry* 1993; vol. 268: 14553-14556.

Davis RJ; Transcriptional regulation by MAP kinases. *Molecular Reproduction Development* 1995; 42: 459-67.

Mabuchi S, Ohmichi M, Kimura A, Hisamoto K, Hayakawa J, Nishio Y, Adachi K, Takahashi K, Arimoto-Ishida E, Nakatsuji Y, Tasaka K, Murata Y; Inhibition of phosphorylation of BAD and Raf-1 by Akt sensitizes human ovarian cancer cells to paclitaxel. *The Journal of Biological Chemistry* 2002; vol. 277:33490-500.

Yacoub A, McKinstry R, Hinman D, Chung T, Dent P, Hagan MP; Epidermal growth factor and ionizing radiation up-regulate the DNA repair genes XRCC1 and ERCC1 in DU145 and LNCaP prostate carcinoma through MAPK signaling. *Radiation Research* 2003; 159: 439-452.

Vaughan K, Manning H. W; Open chain nitrogen compounds. Part XIII. 1-Aryl-3 arylthiomethy1-3-methyltriazenes and 3-(arylazo)-1,3-thiazolidines. *Canadian Journal of Chemistry*, vol. 66:2487-2491,1988.

Zakaria Rachid, Fouad Brahimi, Juozas Domarkas, Bertrand Jacques Jean-Claude. Synthesis of half-mustard combi-molecules with fluorescence properties: correlation with EGFR status, *Bioorganic & Medical Chemistry Letters* 15 (2005) 1135-1138.

Brock R, Hamelers IH, Jovin TM. Comparison of fixation protocols for adherent cultured cells applied to a GFP fusion protein of the epidermal growth factor receptor. *Cytometry* 1999; 35:353-62.

Brahimi F, Zakaria R, Qiu Q, McNamee JP, Li YJ, Tari A, Jean-Claude BJ. Multiple mechanisms of action of ZR2002 in human breast cancer cells: A novel combi-molecule designed to block signaling mediated by the erb family of oncogenes and to damage genomic DNA. *Int. J. Cancer* 2004; 112: 484-91.

Reyderman L., Statkevich P., Thonoor C.M., Patrick J., Batra V.K., Wirth M., Disposition and pharmacokinetics of temozolomide in rat. *Xenobiotica*, May 2004, vol. 34, No. 5, 487-500.

McKillop D., Partridge E.A., Kern J.V., Spence M.P., Kendrew J., Barrett S., Woog P.G., Giles P.B., Patterson A.B., Bichat N., Guilbaud N., Stephens T.C. Tumor penetration of gefitinib (Iressa), an epidermal growth factor receptor tyrosine kinase inhibitor; *Mol Cancer Ther* 2005; 4(4). Apr. 2005, 641-647.

\* cited by examiner (A)

(B)

(C)

(A)

(B)

(C)

(A)

(B)

(C)

(A)

(B)

5

7

9

A) ZR2002     B) ZR2002

A) ZR01     A) ZR01

A

COMBI-MOLECULES HAVING EGFR AND DNA TARGETING PROPERTIES

The present application claims benefit of priority to Canadian Informal application Serial No. 2,471,177 filed Jun. 14, 2004, the entire contents of which is incorporated by reference

FIELD OF THE INVENTION

The present invention relates to novel combi-molecules and bi-combi-molecules having EGFR and DNA targeting properties. More specifically, the present invention relates to novel combi-molecules and bi-combi-molecules capable of blocking signaling mediated by the erbB family of oncogenes and damaging genomic DNA. The present invention also relates to a process for the synthesis of high affinity irreversible inhibitors of epidermal growth factor receptor (EGFR) having fluorescence properties and significant anti-proliferative activity.

BACKGROUND OF THE INVENTION

Overexpression of certain growth factor receptors such as epidermal growth factor receptor (EGFR) as well as the closely related c-erbB2, also known as HER2, are observed in many human cancers including bladder cancer (1), colon carcinoma (2) and lung cancer (3). In breast cancer, high levels of EGFR (4) and erbB2 (5) correlate strongly with poor prognosis. More importantly, these receptors can intensify the transforming signal in a synergistic manner through their ability to form both homo- and heterodimers (6). It has now been shown that by activation of a certain growth factor, the epidermal growth factor receptor (EGFR) induces expression of DNA repair enzymes including ERCC1 and XRCC1, two DNA repair enzymes that are involved in nucleotide excision (NER) and base-excision repair (BER) of alkylated adducts. Tumors overexpressing EGFR are resistant to apoptosis, leading to reduced sensitivity to anti-tumor drugs.

Agents capable of blocking disordered growth signaling, mediated by the tyrosine kinase (TK) activity of these receptors, are now used or are in clinical trials against breast cancer (7, 8). Herceptin (trastuzamad), a humanized antibody against erbB2, showed a 22% response rate as a single agent in metastatic breast cancer (7). ZD1839 (Iressa), an inhibitor of EGFR tyrosine kinase (TK), is now in phase III clinical trials (8).

Agents targeting EGFR and erbB2 present two major advantages. Firstly, they induce selective antitumor activities and secondly, they exhibit a good toxicity profile with only mild side effects. However, where they cannot induce apoptosis, they are cytostatic agents capable of inducing reversible anti-tumor effects.

The anilinoquinazolines are considered the most potent class of EGFR TK inhibitors acting through competitive inhibition of ATP in the TK domain (9, 10, 11). More precisely, anilinoquinazolines inhibit EGFR-related signal transduction by competitive binding in the ATP site. Moreover, a significant number of structure-activity-relationship (SAR) studies on 4-anilinoquinazolines and pyrido[d]pyrimidines as EGFR TK inhibitors have accumulated to suggest that the compounds bind to the ATP site of EGFR. Recently, irreversible inhibitors of EGFR and erbB2 have been developed based on the quinazoline class, by appending an acryloyl group to the 6-position of the anilinoquinazolines as exemplified by PD168393 (Scheme 1).

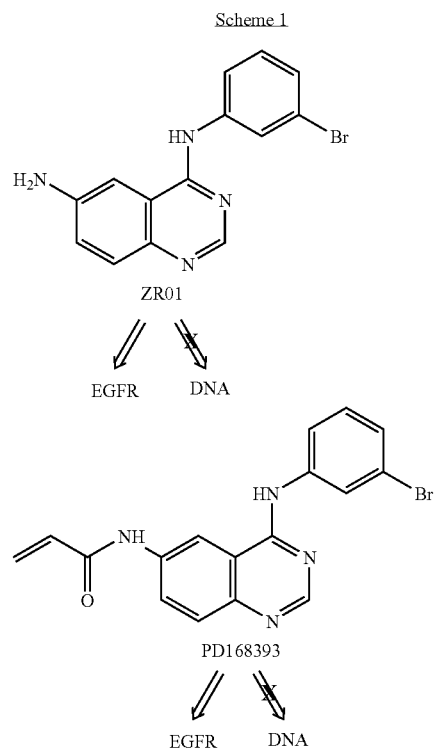

Scheme 1

These inhibitors, containing a Michael acceptor at the 6-position, showed greater potency than their reversible predecessors (12, 13, 14). Their mechanism of action is based on the specific alkylation of Cys-773 of EGFR and erbB2, leading to a covalent inactivation and irreversible inhibition of these receptors. Molecular modeling suggests that the N-1 atom accepts an H-bond from Met-769 and N-3 from the side chain of Thr-766 on strand 5 deep in the binding cleft. The anilino moiety binds in an adjacent hydrophobic pocket.

The binding mode of quinazoline in the ATP site of EGFR has recently been confirmed by X-ray crystallography. These models suggest that the only positions on the inhibitors where substituents can be altered without affecting binding affinity are the 6- and 7-positions which are located at the entrance of binding cleft. Indeed, a variety of compounds with bulky side chains on the 6- and 7-positions have been synthesized and found to retain significant binding affinity for the EGFR ATP binding site.

Fry et al. (13) (Park-Davis Pharmaceutical Research, Division of Warner-Lambert) demonstrated that an acrylamide moiety (Michael acceptor), appended to the 6-position of a quinazoline, adopts the appropriate orientation in order to react with the nucleophilic thiol atom of Cys-773. The distance between these groups was measured as being not greater than 2.8 Å. In contrast, the 7-position is oriented at a distance greater than 7 Å, and the 7-acrylamide substituted analogues alkylate EGFR at a considerably slower rate than those in which it is appended to the 6-position.

More recently, Discafini et al, (15) and Tsou et al. (16) (Wyeth-Ayerst Research, A Division of American Home Products), developed novel compounds bearing different types of Michael acceptors such as butynamides or cyclic α,β-unsaturated ketones. The choice of Michael acceptors is inspired by their mild alkylating activity, a property that is considered critical for specific alkylation of the cystein residue of EGFR to occur.

In order to further potentiate the action of EGFR TK inhibitors, studies have been designed to combine them with classical cytotoxic drugs (8, 17, 18). Within the same line of idea, Jean-Claude et al. have recently developed a novel tumor targeting strategy, termed "combi-targeting", that seeks to The first prototypes of combi-molecules contained a quinazoline head and a triazene (ZRBA1) or a nitrosourea tail (FD137) (Scheme 2). These combi-molecules were designed not only to bind to the receptor on their own, but also to degrade to an aminoquinazoline capable of further blocking EGFR TK and an alkylating species. While the binary potency of these compounds has now been well demonstrated, they were all designed to release a stoichiometric amount to the free inhibitor in addition to the release of a stoichiometric amount of an alkylating species.

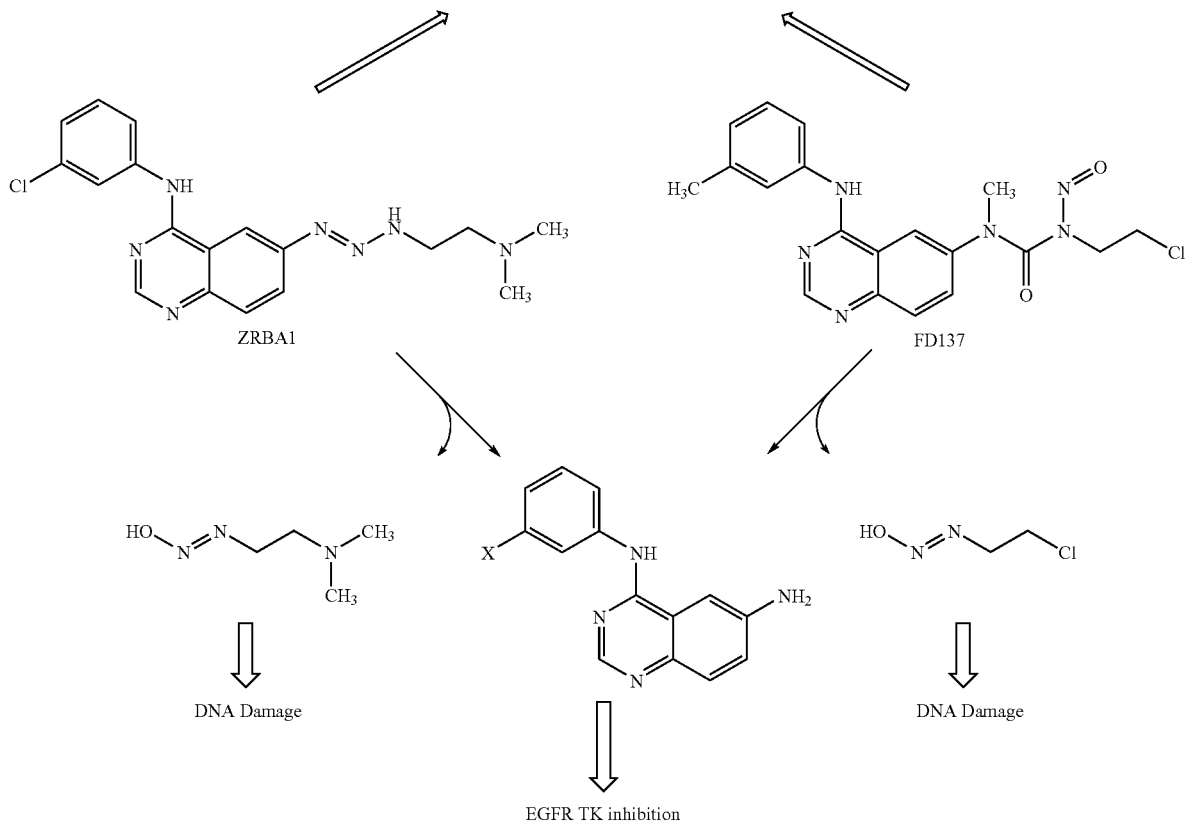

develop novel drugs designated as "combi-molecules" capable of blocking growth factor-mediated signaling while inducing cytotoxic DNA damage. The "combi-targeting" strategy consists of combining a cytotoxic DNA damaging function with an EGFR inhibitory property into single molecule i.e. "combi-molecule". These "combi-molecules" are designed to release to the two moieties (i.e. the cytotoxic DNA damaging function and the EGFR inhibitory function) upon hydrolysis. Furthermore, Jean-Claude et al. have recently demonstrated that following cell penetration, these combi-molecules require hydrolytic scission to generate the cytotoxic function (19, 20, 21). The combi-targeting strategy is based on the premise that blocking EGFR-mediated signaling via a kinase inhibitory component and damaging DNA by an alkylating function will induce a tandem block of EGFR activation and that of DNA repair enzymes required to rescue the cells. This in turn is expected to lead to synergistic killing of EGFR-overexpressing cells.

There thus remains a need for the development of a new prototype of combi-molecule having increased tumor selectivity and improved efficacy in refractory tumors. Moreover specifically, there remains a need to develop a new prototype type of combi-molecule that does not require hydrolysis to generate the mixed EGFR and DNA targeting properties. There also remains a need to develop a process for the synthesis of novel potent inhibitors of epidermal growth factor receptor having fluorescent properties. Finally, there remains a need to develop biomarkers having high selectivity for EGFR.

The present invention seeks to meet these and other needs.

The present invention refers to a number of documents, the content of which is herein incorporated by reference in their entirety.

SUMMARY OF THE INVENTION

The present invention relates to combi-molecules including a 4-anilinoquinazoline ring system comprising an alkylating moiety. The present invention relates to a new prototype of combi-molecule having increased tumor selectivity and improved potency and efficacy. The present invention also relates to a new prototype type of combi-molecule that does not require hydrolysis to generate the mixed EGFR and DNA targeting properties. Moreover, the present invention relates a new class of combi-molecule potentially capable of releasing 2-moles of inhibitor in addition to the release of a DNA damaging function.

In an embodiment, the present invention relates to a combi-molecule comprising a first portion being an inhibitor to a molecule involved in cell signaling pathways and a second portion being an agent capable of damaging DNA, the combi-molecule being capable of (a) inhibiting the molecule involved in cell signaling pathways; and (b) damaging DNA.

In an embodiment, the present invention relates to a double-arm combi-triazene comprising a pair of ligands to a molecule involved in cell signaling pathways, the double-arm combi-triazene being capable of (a) inhibiting the molecule involved in cell signaling pathways; and (b) generating a pair of inhibitors to the molecule involved in cell signaling pathways and generating a DNA damaging agent upon degradation.

In an embodiment, the present invention relates to a combi-molecule being an inhibitor to a molecule involved in cell signaling pathways, said combi-molecule being capable upon metabolic activation of degrading to (a) a further inhibitor to the molecule involved in cell signaling pathways, and (b) an agent capable of damaging DNA.

In an embodiment, the present invention relates to a molecule of Formula I or a pharmaceutically acceptable salt thereof:

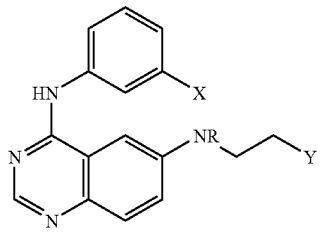

Formula I wherein:
a) R is selected from the group consisting of: H, Me, and 2-chloroethyl;
b) X is selected from the group consisting of Cl, Br, I, H and Me; and
c) Y is selected from the group consisting of Cl, Br, I, OTs, and OMs.

In a further embodiment, the present invention relates to a molecule of Formula II or a pharmaceutically acceptable salt thereof:

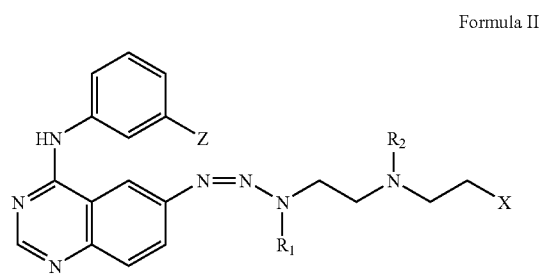

Formula II wherein:
a) $R_1$ is selected from the group consisting of H and Me;
b) $R_2$ is selected from the group consisting of H, Me, $CH_2CN$, 2-chloroethyl, ethyl, propyl, butyl, pentyl, cyclopentyl, hexyl, cyclohexyl, benzyl, phenyl, pyridyl, and imidazolyl;
c) X is selected from the group consisting of Cl, Br, I, OTs, OMs and $OSO_2Me$; and
d) Z is selected from the group consisting of Cl, Br, I, H and Me.

In yet a further embodiment, the present invention relates to a molecule of Formula III or a pharmaceutically acceptable salt thereof:

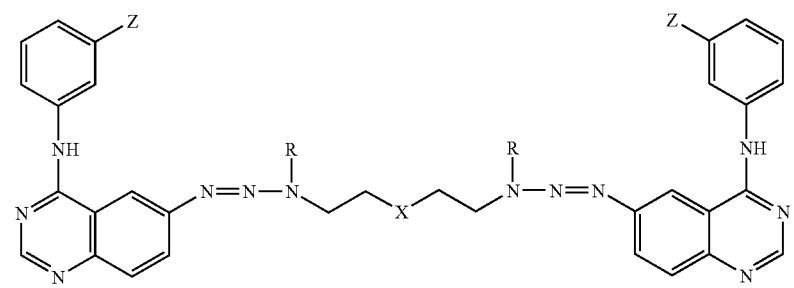

Formula III wherein:
a) R is selected from the group consisting of H and Me;
b) X is selected from the group consisting of O, NMe, N-cyclohexyl and

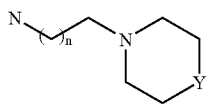

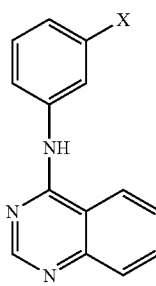

wherein n is an integer ranging from 1 to 4 and wherein Y is selected from the group consisting of O, C and N; and c) Z is selected from the group consisting of Cl, Br, I, H and Me.

In yet a further embodiment, the present invention relates to a molecule of general Formula IV or a pharmaceutically acceptable salt thereof:

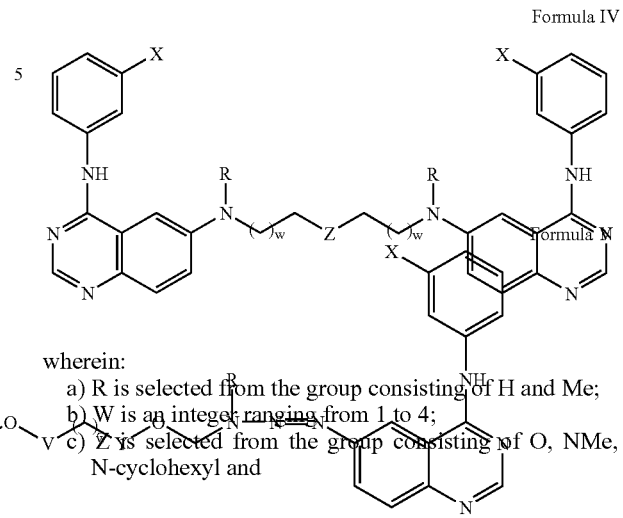

Formula IV wherein:
a) R is selected from the group consisting of H and Me;
b) W is an integer ranging from 1 to 4;
c) Z is selected from the group consisting of O, NMe, N-cyclohexyl and

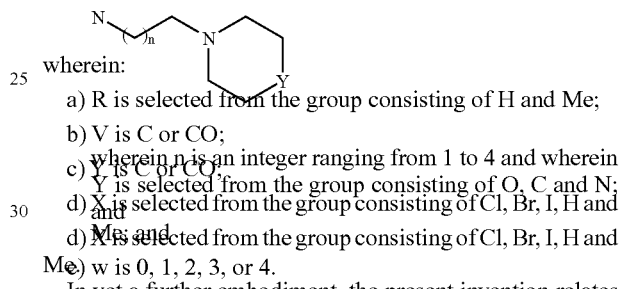

wherein:
a) R is selected from the group consisting of H and Me;
b) V is C or CO;
c) wherein n is an integer ranging from 1 to 4 and wherein Y is selected from the group consisting of O, C and N; and
d) X is selected from the group consisting of Cl, Br, I, H and Me; and
e) w is 0, 1, 2, 3, or 4.

In yet a further embodiment, the present invention relates to a molecule of general Formula VI or a pharmaceutically acceptable salt thereof:

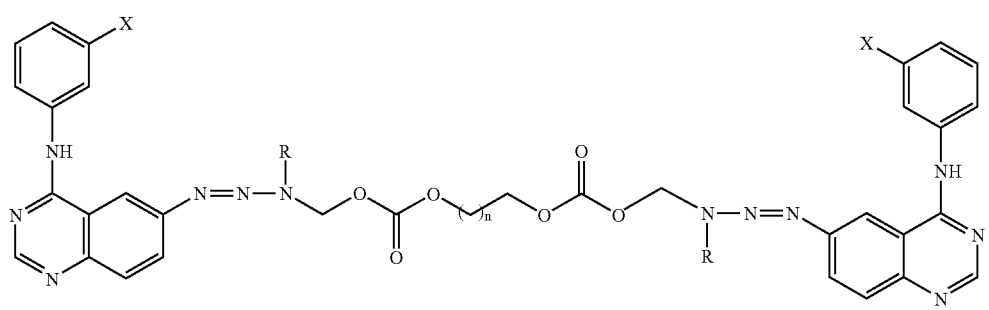

Formula VI wherein:
a) R is selected from the group consisting of H and Me;
b) X is selected from the group consisting of Cl, Br, I, H and Me; and
c) n is 0, 1, 2, 3, or 4.

In yet a further embodiment, the present invention relates to a molecule of Formula VII or a pharmaceutically acceptable salt thereof:

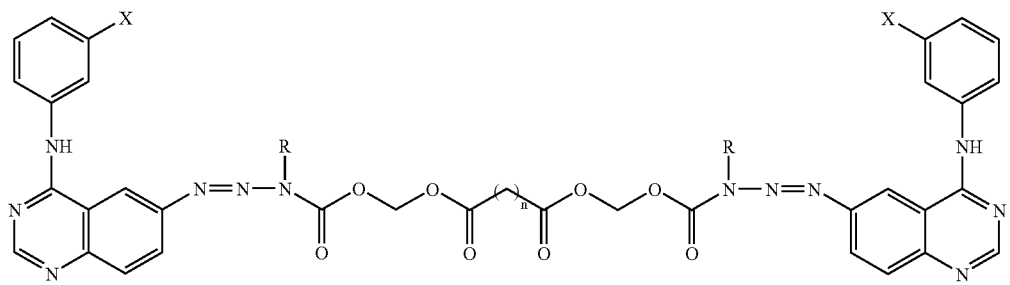

Formula VII

In yet a further embodiment, the present invention relates to a molecule of Formula VIII or a pharmaceutically acceptable salt thereof:

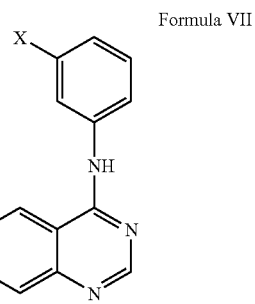

Formula VIII wherein:
a) R is selected from the group consisting of H and Me; and
b) X is selected from the group consisting of Cl, Br, I, H and Me; and
c) n is 0, 1, 2, 3, or 4.

In yet a further embodiment, the present invention relates to a molecule of Formula X or a pharmaceutically acceptable salt thereof:

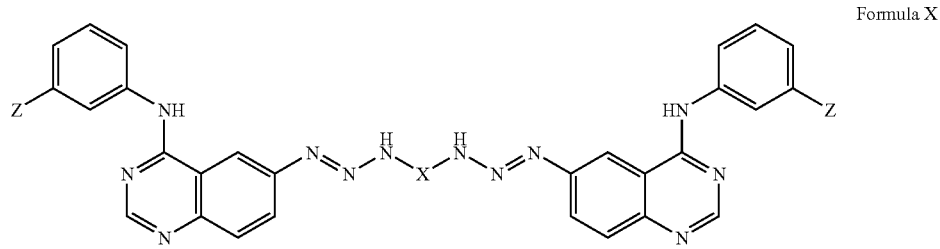

Formula X wherein:
a) Z is selected from the group consisting of Cl, Br, I, H and Me; and
b) X is selected from the group consisting of

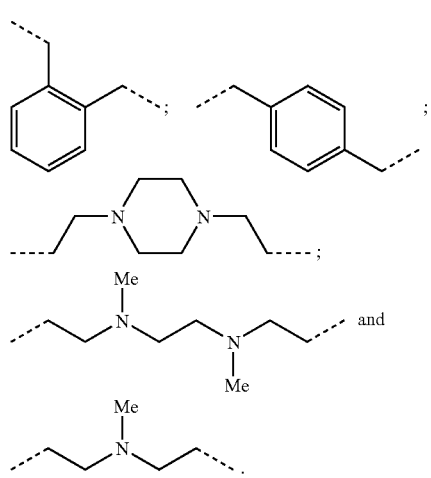

wherein:
a) X is selected from the group consisting of Cl, Br, I, H or Me; and
b) R is selected from the group consisting of methyl, phenyl, pyridyl, imidazolyl, N-morpholine, and

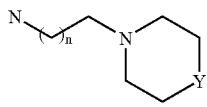

wherein n is an integer ranging from 1 to 4 and wherein Y is selected from the group consisting of O, C and N.

In yet a further embodiment, the present invention relates to a molecule of Formula IX or a pharmaceutically acceptable salt thereof:

Formula IX

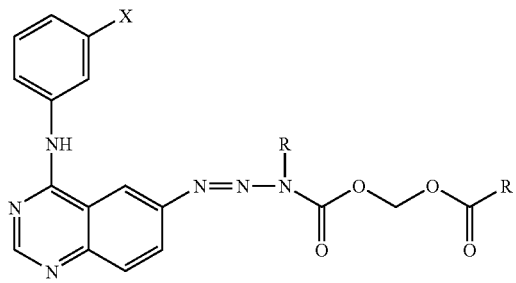

wherein
a) X is Cl, Br, I, H, or Me; and
b) R is selected from the group consisting of methyl, phenyl, pyridyl, and

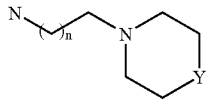

wherein n is an integer ranging from 1 to 4 and wherein Y is selected from the group consisting of O, C, and N.

The present invention also relates to a combi-molecule (ZR2002) having a 2-chloroethyl group appended to the 6-position of an anilinoquinazoline.

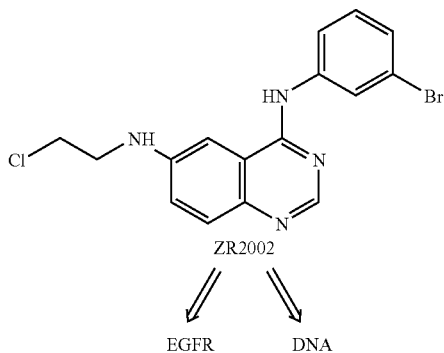

The present invention also relates to a combi-molecule (ZR2003) having a 2-chloroethyl group appended to the 6-position of an anilinoquinazoline.

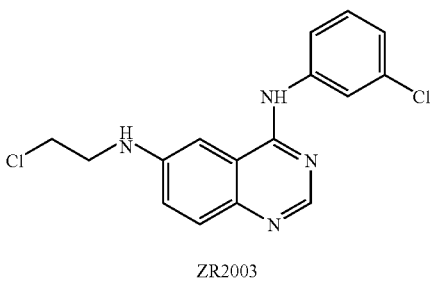

The present invention also relates to a non-Michael acceptor approach to irreversible inhibitors of EGFR, involving a mild alkylating $S_N2$ type reaction. In contrast to the amidic acrylamide moieties that are electron-withdrawing groups, the present invention relates to the synthesis of electron-rich irreversible inhibitors, which, by electron delocalization toward the quinazoline ring system, confer fluorescence properties to the inhibitors. The synthesis of the compounds of the present invention lends itself to the facile incorporation of radiolabeled atoms.

Furthermore, the present invention relates to a process for appending a 2-chloroethyl group to the 6-position of quinazolines without being affected by the 1,3 nitrogens.

Moreover, the present invention relates to a process permitting the rapid and facile appending of a radio-labeled haloalkyl group to the quinazoline.

Moreover, the present invention relates to molecules having potent and selective anti-proliferative activity in cells expressing EGFR as well as the closely related c-erbB2, also known as HER2.

Finally, the present invention relates to biomarkers having high selectivity for EGFR Further scope and applicability will become apparent from the detailed description given herein after. It should be understood however, that this detailed description, while indicating preferred embodiments of the invention, is given by way of illustration only, since various changes and modifications within the spirit and scope of the invention will become apparent to those skilled in the art.

BRIEF DESCRIPTION OF THE DRAWINGS

Having thus generally described the invention, reference will now be made to the accompanying drawings, showing by way of illustration a preferred embodiment thereof, and in which.

Figure 1:
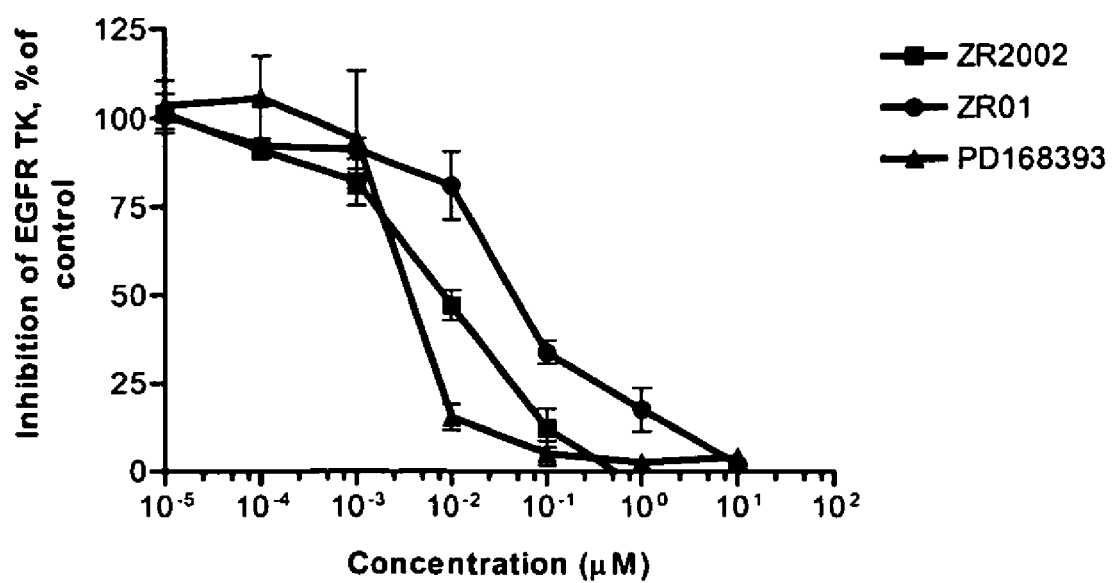
FIG. 1 shows the competitive binding (ELISA) to EGFR by ZR2002, PD168393 and ZR01. Poly (L-glutamic acid-L-tyrosine, 4:1) substrate phosphorylation was detected using an anti-antiphostyrosine antibody. ZR2002 ($IC_{50}$=0.010 µM), PD168393 ($IC_{50}$=0.0321 µM), ZR01 ($IC_{50}$=0.048 µM). Each point represents at least two independent experiments.

Other objects, advantages and features of the present invention will become more apparent upon reading of the following non-restrictive description of preferred embodiments with reference to the accompanying drawing which is exemplary and should not be interpreted as limiting the scope of the invention.

DETAILED DESCRIPTION OF EMBODIMENTS

Selected abbreviations: EGFR: Epidermal Growth Factor Receptor; TK: Tyrosine Kinase; EGF: Epidermal Growth Factor; DMSO: Dimethyl Sulfoxide; FBS: Fetal Bovine Serum; SRB: Sulforhodamine B; PGT, Poly (L-Glutamic acid-L-Tyrosine, 4:1); PBS: Phosphate-Buffered Saline; HRP: Horseradish Peroxidase; ELISA: Enzyme-Linked Immunosorbent Assay; PDGF: Platelet-Derived Growth Factor; MAPK: Mitogen-Activated Protein Kinase; Erk1, 2: Extracellular Signal-Regulated Kinase 2; TGFa: Transforming Growth Factor alpha; AGT: $O^6$-Alkylguanine Transferase; PI: Propidium Iodide.

As used herein, pharmaceutically acceptable salts include the acid addition and the base salts of the combi-molecules of the present invention. Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts. Suitable base salts are formed from bases which form non-toxic salts and examples are the sodium, potassium, aluminum, calcium, magnesium, zinc and diethanolamine salts.

As used herein, pharmaceutically acceptable solvates include the hydrates of the combi-molecules of the present invention.

In broad terms, the present invention relates to a new prototype of combi-molecules designed to block EGFR and its closest homologue p185$^{neu}$, the gene product of HER2, and to damage DNA. Kinase-targeted molecules, designed to possess DNA damaging properties should be more potent than their mono-targeted counterparts in refractory tumors. In one embodiment of the present invention, the combi-molecules were designed to (a) induce binary kinase inhibitory activity/DNA lesions without the requirement for hydrolytic cleavage, and (b) hydrolyze to generate an inhibitor of a kinase as well as a DNA damaging species.

In an embodiment of the present invention and as outlined in Scheme 3, a combi-molecule TZ-I containing a DNA damaging tail (TZ) and an EGFR targeting head (I), can directly damage DNA (TZ-I-DNA), and block EGFR TK activity (TZ-I-EGFR) without the requirement for hydrolytic scission (Mechanism A). Alternatively, in a further embodiment of the present invention, the combi-molecule TZ-I can be programmed to not only be an EGFR inhibitor on its own but to also degrade to generate another molecule of inhibitor I and a DNA damaging agent TZ (Mechanism B).

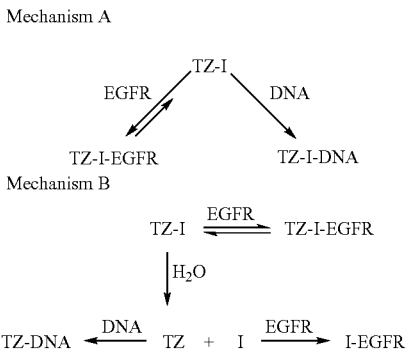

Diverse irreversible inhibitors of EGFR were obtained by appending an acryloyl group to the 6-position of an anilinoquinazoline. However, the use of other alkylating functional groups at this position has remained unexplored. The acryloyl group exhibits the advantage of being a moderately reactive Michael acceptor while neither causing autoalkylation nor unspecific alkylation of biological nucleophiles. More importantly, the appending of the acryloyl group to the 6-position of an anilinoquinazoline does not involve an alkylation reaction that may be hampered by the reactivity of the 1,3-nitrogens of the pyrimidine ring of the quinazolines. The reactivity of the 1,3-nitrogens has limited the synthesis of 6-substituted quinazolines and more specifically those containing 6-haloalkyl groups.

In an embodiment, the present invention relates to a process for appending a chloroethyl group to the 6-position of quinazolines without being affected by the 1,3 nitrogens. ZR2002, a compound obtained by such a process, is a stable compound that does not self-alkylate. The process lends itself to the facile appending of a radio-labeled haloalkyl group to the quinazoline structure (i.e. to the 6-position). These compounds display potent and selective anti-proliferative activity in cells expressing EGFR or p185neu, the HER2 gene product.

The synthesis of ZR2002 is carried out as outlined in Scheme 4 and involves the alkylation of amine 2 using an electrophile. However, this synthesis often results in complex reaction mixtures and complex purification and isolation procedures, due to alkylation of the 1,3-nitrogens of the pyrimidine ring of the quinazolines.

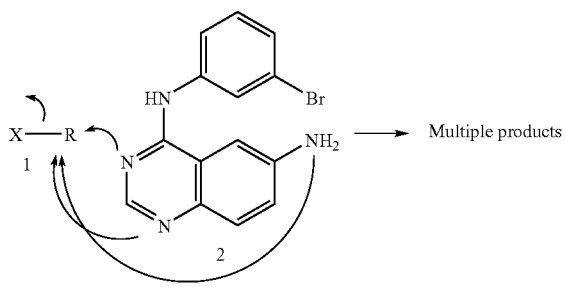

As outlined in Scheme 5, chloroethylamine can be directly used in the synthesis of the desired compound ZR2002. Amine 1 is diazotized using nitrosonium tetrafluoroborate to give rise to the diazonium complex 2. Addition of chloroethylamine hydrochloride provides the metastable triazene 3 which self-decomposes to the desired chloroethylamine 4 (ZR2002). ZR2002 is a typical example of a "combi-molecule" capable of directly alkylating DNA and binding to EGFR according to mechanism A (Scheme 3).

involves the use of commercially available dimethylethylamine and pyrrolidine respectively.

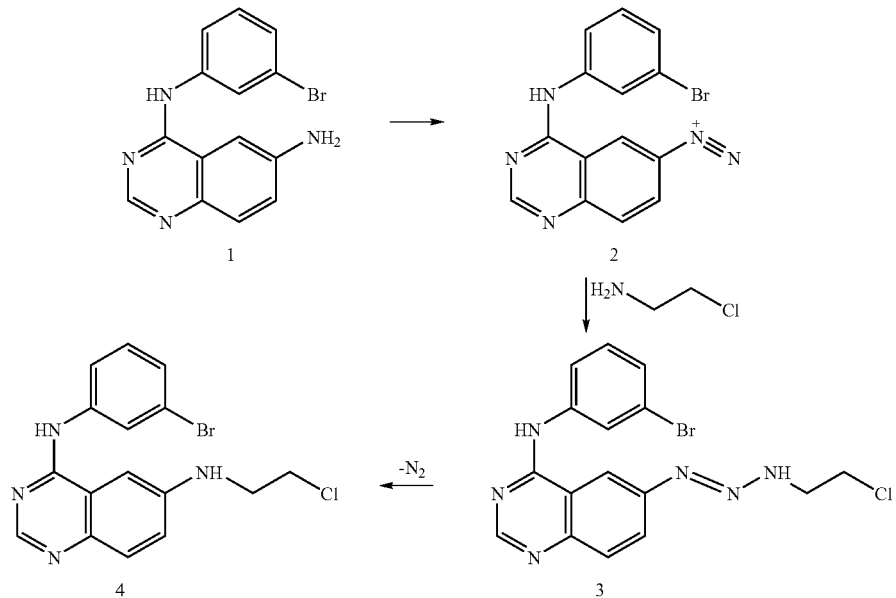

Further examples of "combi-molecules" capable of directly alkylating DNA and binding to EGFR according to mechanism A (Scheme 3) as contemplated by the present invention, are illustrated by the more general structure illustrated in Scheme 6.

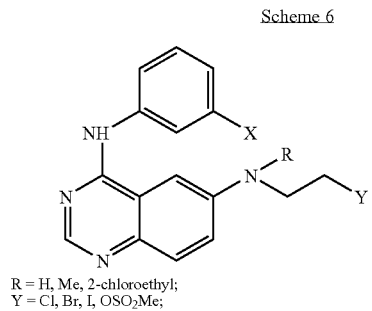

R = H, Me, 2-chloroethyl;
Y = Cl, Br, I, OSO$_2$Me;
X = Cl, Br, I, H, Me

Triazenes have been previously designed to be hydrolyzed under physiological conditions to generate an amine (I) and a DNA damaging alkyldiazonium (TZ) (20). Therefore, combi-molecules such as ZRBA1 and ZRBA2 require hydrolysis to generate their binary targeting properties as per mechanism B (Scheme 3). The synthesis of these compounds proceeded via diazotization of the corresponding aminoquinazolines followed by the addition of the corresponding alkylamine and subsequent neutralization with triethylamine. The synthesis of ZRBA1 and ZRBA2, is shown below in Scheme 7, and

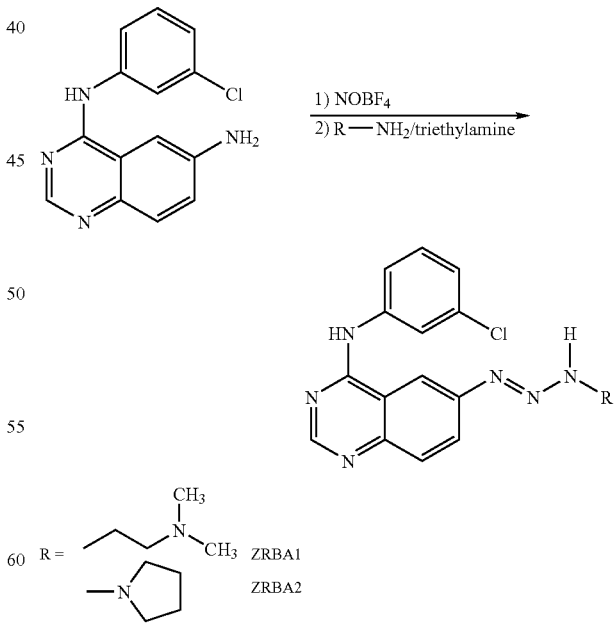

The synthesis of ZRBA4 is shown below in Scheme 8, and involves N-(2-chloroethyl)-N-methylethylenediamine which was synthesized as shown in Scheme 9.

Scheme 8
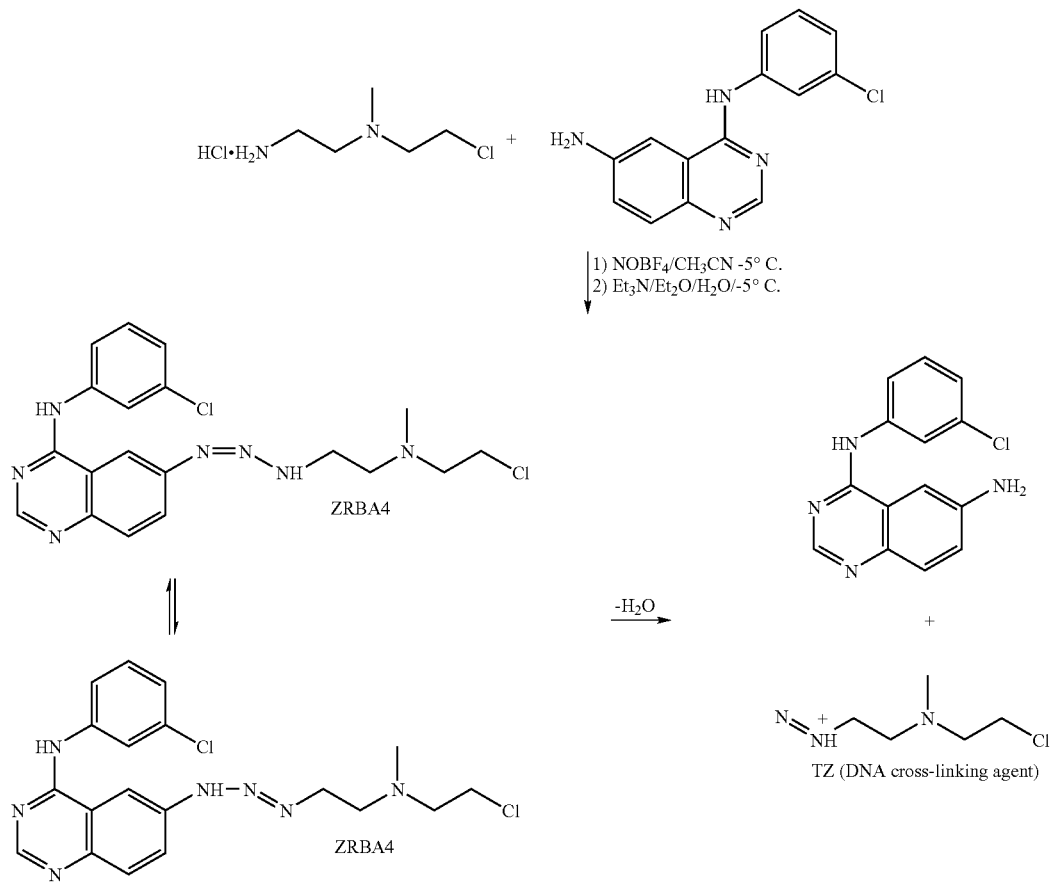

Scheme 9

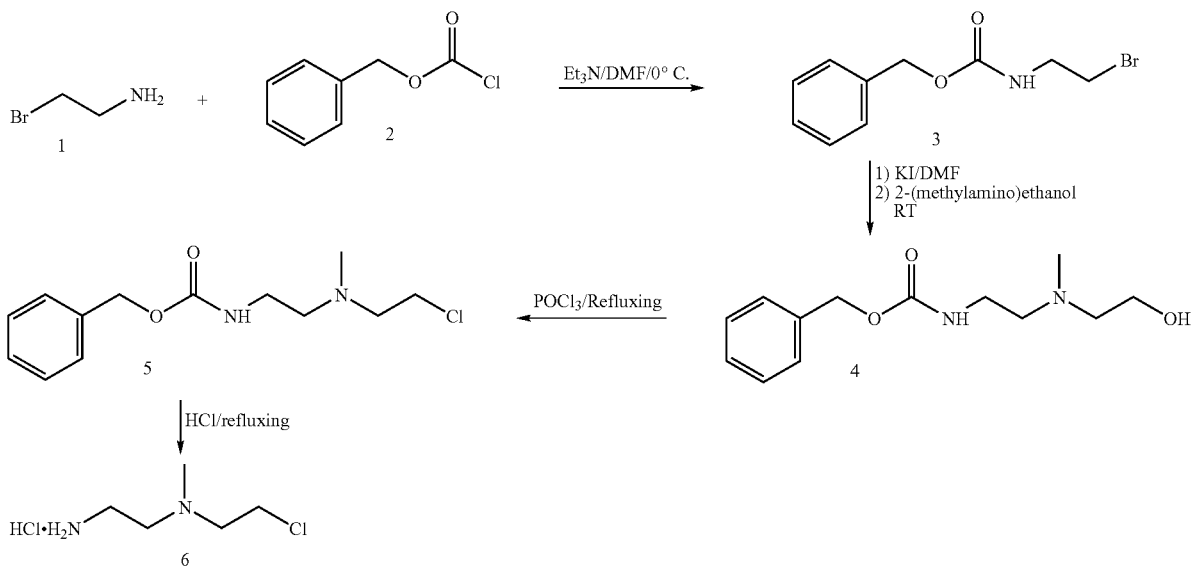

While the hydrolysis of ZRBA1 and ZRBA2 will provide a mono-functional alkylating agent, ZRBA4 is designed to generate a bifunctional alkylating agent reminiscent of mechlorethamine, the latter compound being a clinical antitumor agent used in the therapy of a variety of neoplasms.

Further examples of "triazenes" capable of generating a bi-functional alkylating agent as contemplated by the present invention are illustrated by the general structure illustrated below in Scheme 10.

Scheme 10

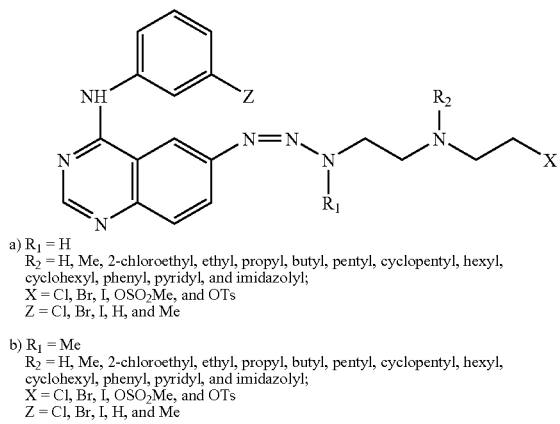

a) $R_1$ = H
$R_2$ = H, Me, 2-chloroethyl, ethyl, propyl, butyl, pentyl, cyclopentyl, hexyl, cyclohexyl, phenyl, pyridyl, and imidazolyl;
X = Cl, Br, I, $OSO_2Me$, and OTs
Z = Cl, Br, I, H, and Me b) $R_1$ = Me
$R_2$ = H, Me, 2-chloroethyl, ethyl, propyl, butyl, pentyl, cyclopentyl, hexyl, cyclohexyl, phenyl, pyridyl, and imidazolyl;
X = Cl, Br, I, $OSO_2Me$, and OTs
Z = Cl, Br, I, H, and Me In order to (a) further enhance the potency of the released cytotoxic agent, and (b) enhance EGFR TK inhibitory activity, bis-molecules ("bi-combi-molecules") capable of releasing a bi-functional alkylating agent and 2 moles of inhibitor were designed (equation 1).

$$I\text{-}TZ\text{-}I \rightarrow TZ+2I \tag{1}$$

In an embodiment of the present invention, a second anilinoquinazoline ring was appended to the 6-position of an anilinoquinazoline through a spacer. Moreover, by inserting a double-arm spacer attached to a triazene chain, a novel class of combi-molecules could be obtained that upon hydrolysis releases: (a) a bi-functional alkylating agent and (b) two moles of 6-aminoquinazoline (shown below), a potent EGFR inhibitor. One of the characteristics of this new class of combi-molecule is the presence of an axis of symmetry.

Examples of "bi-combi-molecules" as contemplated by the present invention and capable of releasing a bi-functional alkylating agent and 2 moles of inhibitor are illustrated by the general structures shown below in Scheme 11.

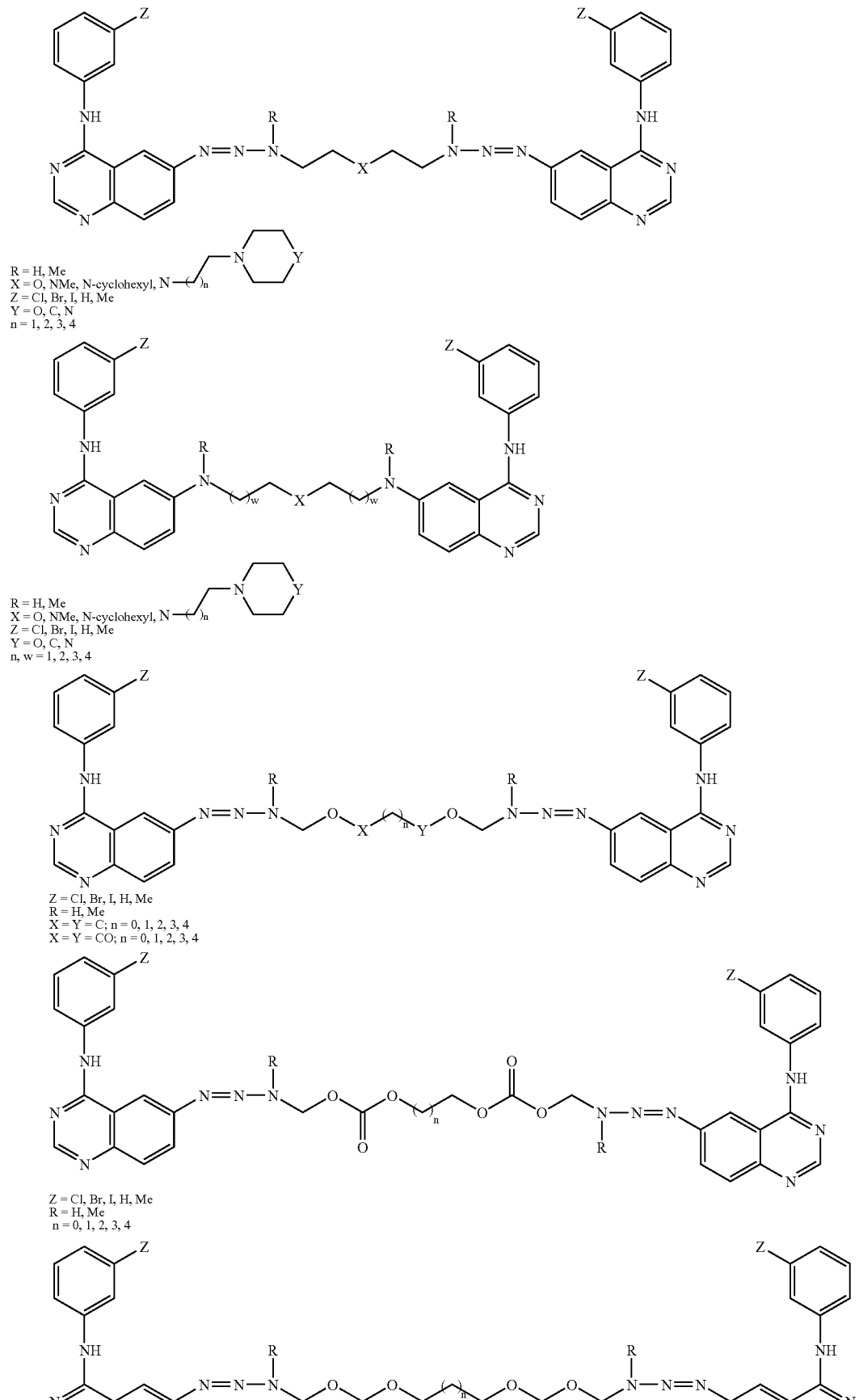

Further examples of "bi-combi-molecules" as contemplated by the present invention, more specifically double-arm combi-triazenes capable of releasing a bi-functional alkylating agent and 2 moles of inhibitor are illustrated below in Scheme 12. These "bi-combi-molecules" are characterized by an amine spacer linking a pair of triazene chains.

An o-diaminoxylene system (2, Scheme 13) would favor a more compact molecule (5, Scheme 12) by imposing a shoulder to the system. On the other hand, the use of commercially available p-diaminoxylene provided a more open-armed structure (6, Scheme 12). Based on the significant antitumor activity observed in vivo with ZRBA1 (Scheme 2), which

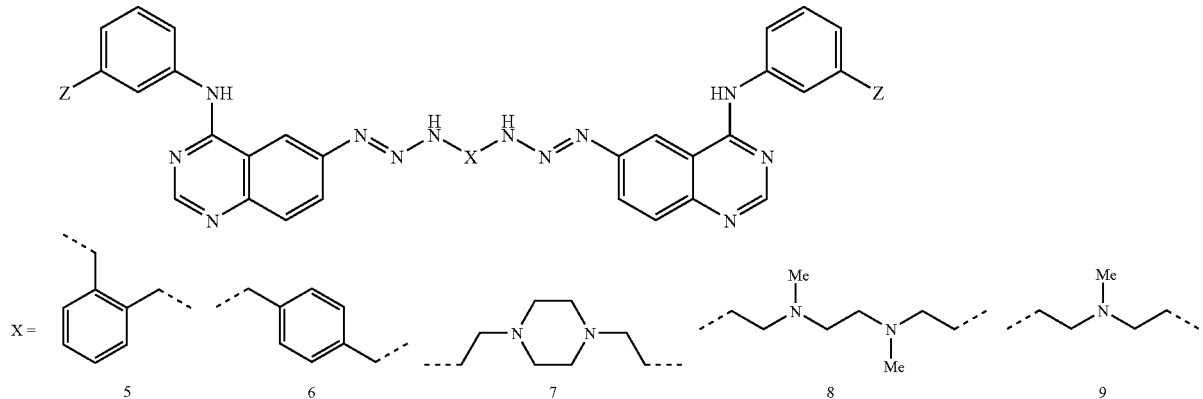

The synthesis of the double-arm combi-triazenes is preceded by the preparation of bis-aminoethyl spacers as illustrated below in Scheme 13 [(i) (t-Bu)$_2$NH, NaH, DMF, 60° C., 6 h; then, addition of xylene, 60° C., 4 h; (ii) HCl conc., heat, 15 min.; (iii) ClCH$_2$CN, CH$_3$CN, RT, overnight; (iv) LiAlH$_4$, THF, reflux, 3 h] The amine spacers are designed so as to be capable of imposing different geometries to the double-arm molecule.

contains a diaminoethylamine function, double-arm combi-triazenes 7 and 8 were designed (Scheme 12). Double-arm combi-triazenes 7 and 8 respectively comprise a conformationally restricted N,N'-bis-(2-aminoethyl)-piperazine and a conformationally free N,N'-bis-(2-aminoethyl)-N,N'-dimethylethylene diamine spacer. Furthermore, in the category of flexible spacers, a N,N-bis-(2-aminoethyl)-methylamine spacer was incorporated to provide double-arm combi-triazene 9 which was designed to release a nitrogen mustard species.

As illustrated below in Scheme 14 [(i) NOBF$_4$, CH$_3$CN, −5° C., 15 min.; (ii) NH$_2$XNH$_2$, DIPEA, CH$_3$Cl, −5° C., 5 min] the synthesis of the double-arm combi-triazenes proceeded by coupling of the diazonium salt of 6-aminoquinazoline 1, prepared in situ by nitrosation of 1 with NOBF$_4$ in acetonitrile, with the diamine spacer. Purification of the double-arm combi-triazenes has proven difficult. However a significant degree of purity could be achieved by chromatography using basic alumina and an eluent system comprising THF and 0.5-1% water. The double-arm combi-triazenes were subsequently characterized by NMR and by mass spectrometry (electrospray).

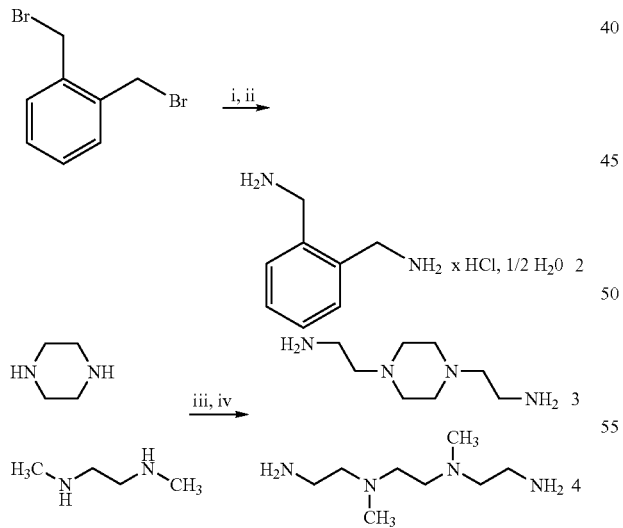

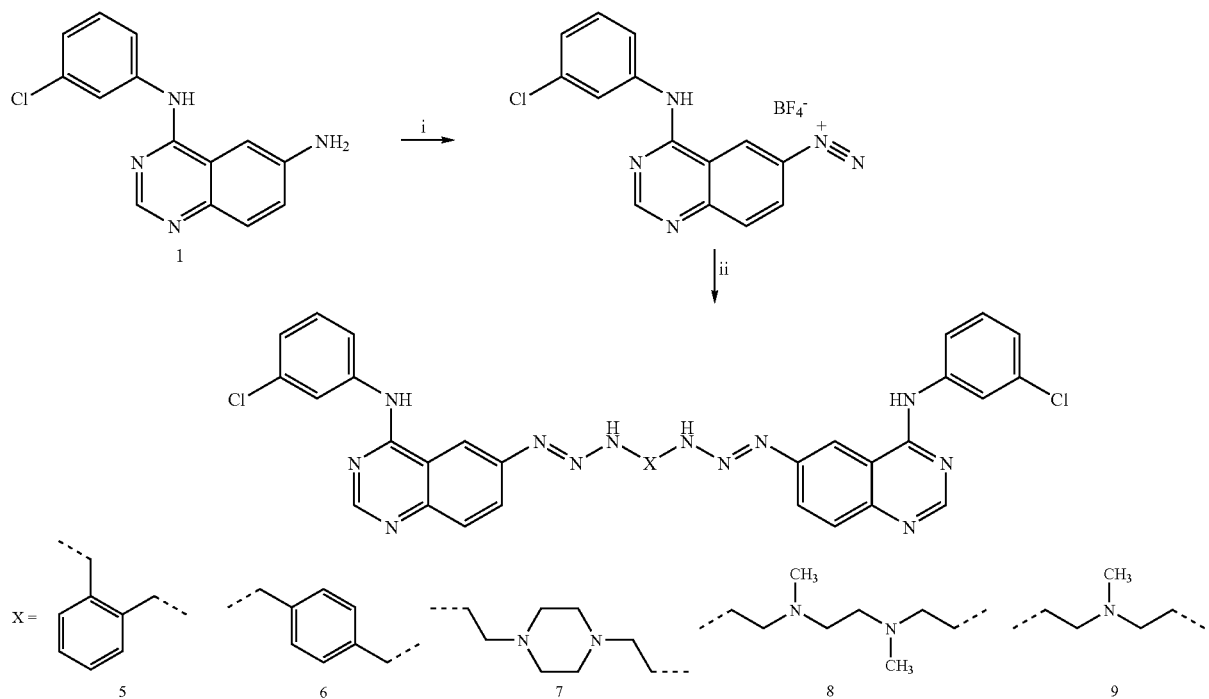

Scheme 14

Figure 12:
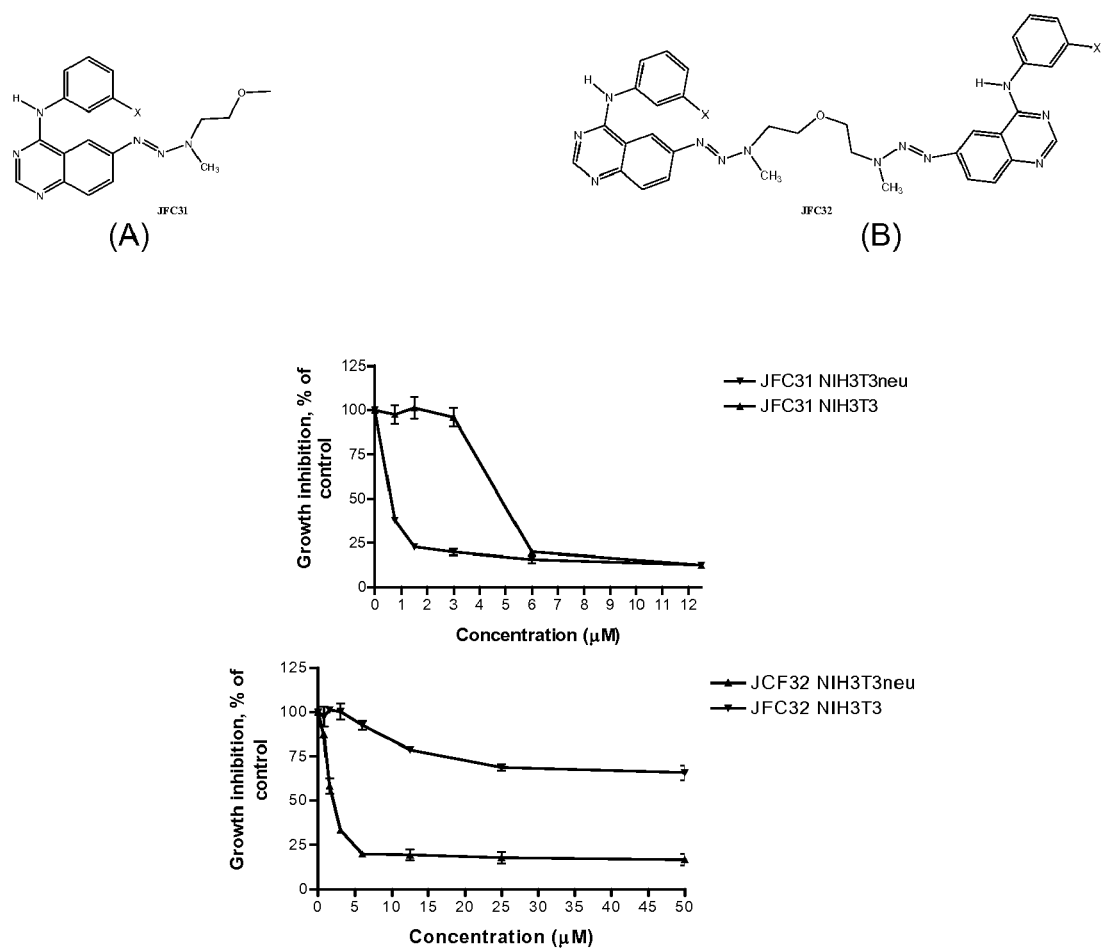
FIG. 12 shows the effect of JFC31 (A) and JFC32 (B) on growth proliferation in NIH3T3 and NIH3T3neu cells. Cells were exposed to each drug for 72 h. Cell growth was measured using the SRB assay. Each point represents at least two independent experiments.

An important aspect of the present "combi-molecule" approach is that the combi-molecule (TZ-I) itself must be an EGFR inhibitor. A series of stable "bi-combi-molecules" were synthesized and their affinity for the ATP binding site of EGFR evaluated. Since the SAR (structure activity relationship) in the quinazolines series showed a high tolerance for bulkiness at the 6-position, some EGFR inhibitory activity for the bi-combi-molecules was expected, and this despite the bulkiness of the structures. Surprisingly, the bi-combi-molecules, and more specifically JFC31, showed significant potency against tumor cells overexpressing HER2 or EGFR. More importantly, in an isogenic model, JFC31 showed significant selectivity for the transformed NIH3T3 HER2 transfected cells, indicating a remarkable normal cell sparing effect (FIG. 12). JFC31 was designed to be demethylated in vivo to generate the mono-alkyltriazene capable of being hydrolyzed to two inhibitors of EGFR and a DNA damaging agent as per equation (1). Results for other "bi-combi-molecules" are illustrated in Table 1.

TABLE 1

$IC_{50}$ values (μM) for inhibition of EGFR kinase and blockade of serum-stimulated growth.

| Compounds | EGFR Binding | Inhibition of growth stimulation of NIH3T3neu | Inhibition of growth stimulation of NIH3T3 | Inhibition of basal growth of A431 |
|---|---|---|---|---|
| JFC30 | 0.014 | 1.25 | 13.87 | 18.86 |
| JCF29 | 0.036 | 43.29 | 185.6 | 38.06 |
| JFC16 | 0.29 | 23.14 | 137.2 | — |
| JFC32 | 0.013 | 1.65 | 111.6 | 23.39 |
| JFC31 | 0.003 | <0.75 | 4.654 | 4.791 |

The structures of the bi-combi-molecules of Table 1, are illustrated below in Scheme 15.

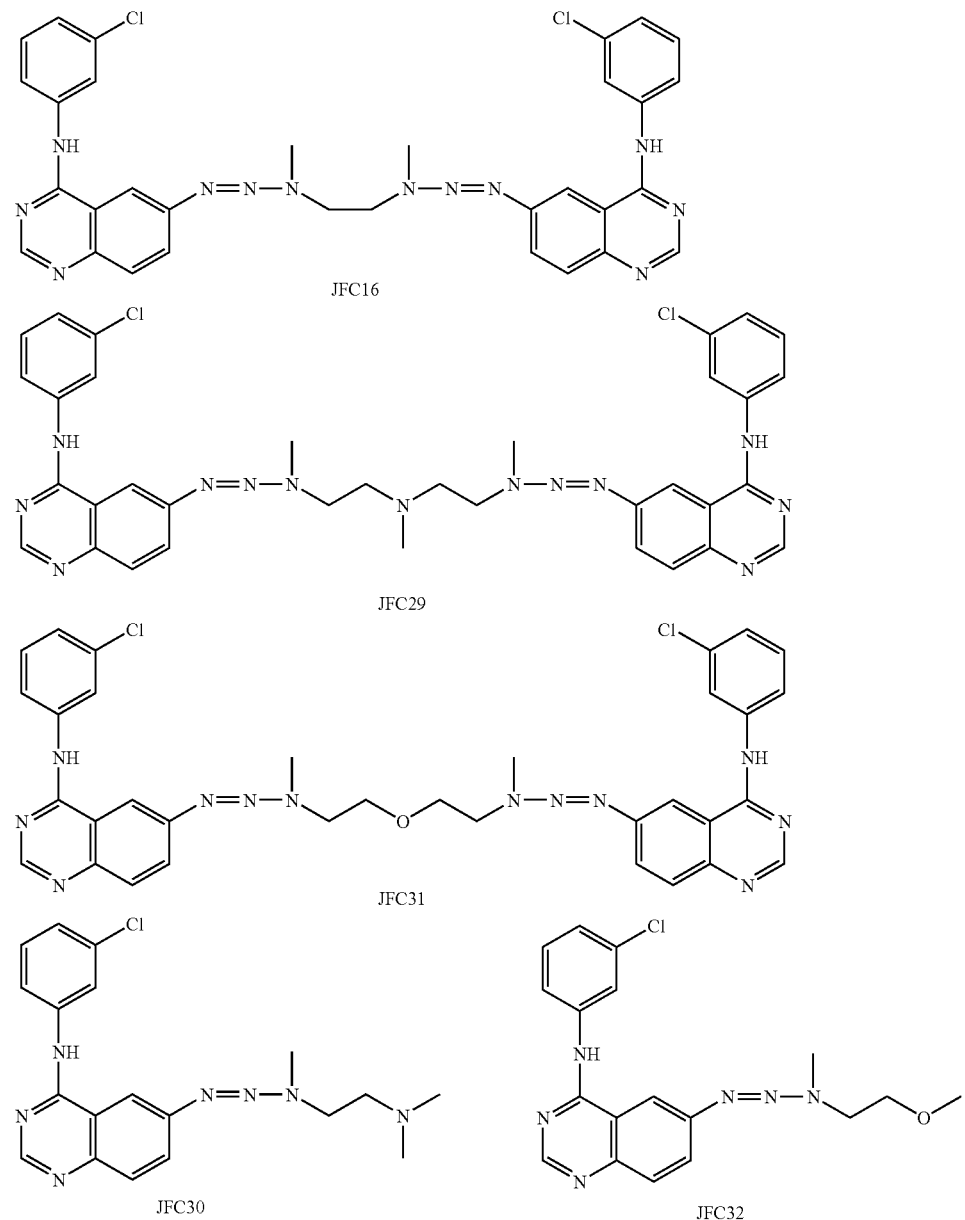
The synthesis of JFC31 is shown below in Scheme 16.

Scheme 16
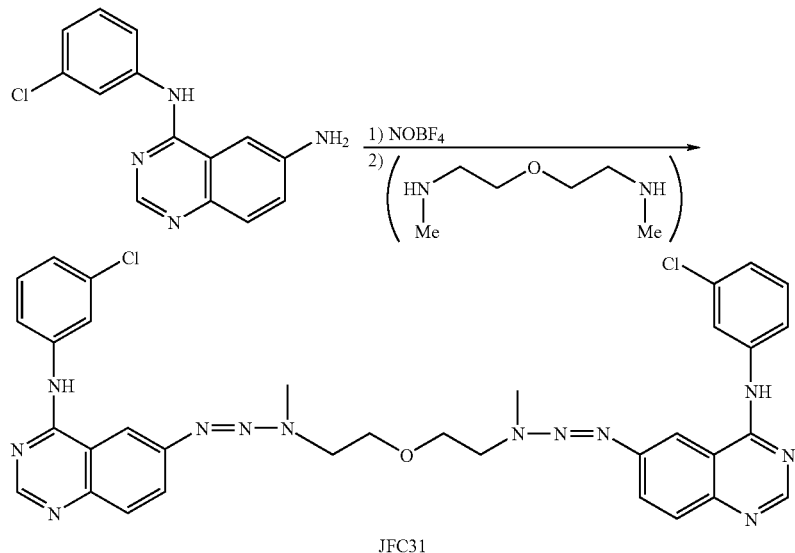
As outlined in Scheme 17, JFC31, when metabolized, is designed to provide 2 moles of inhibitor (I) as well as a bi-functional alkylating agent (TZ).
Scheme 17
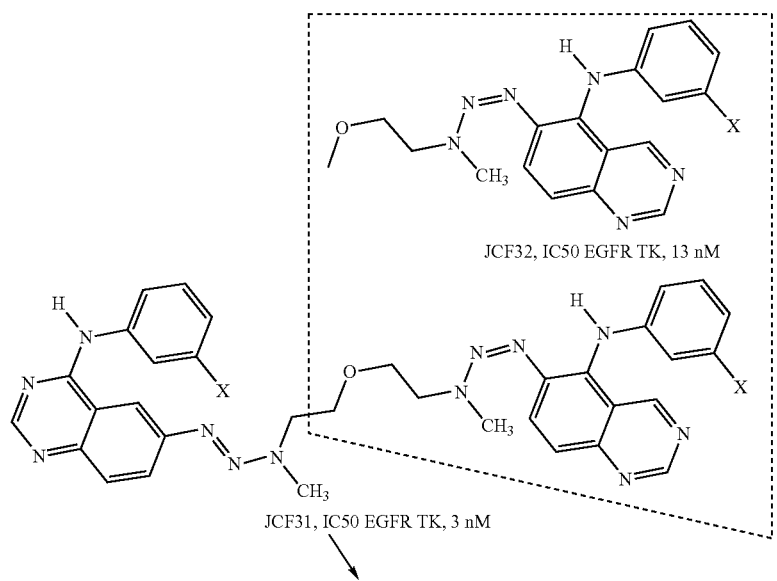

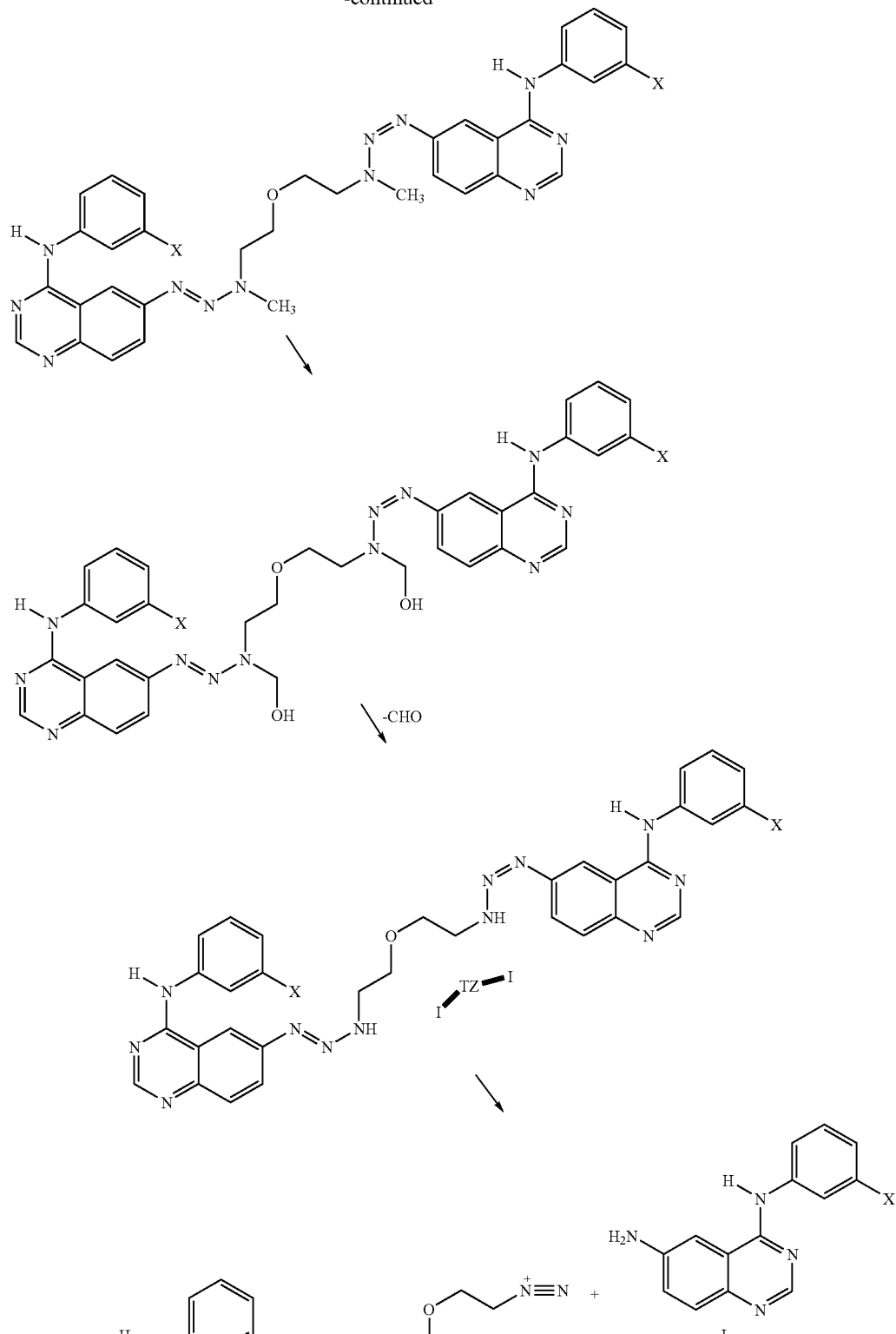

The present invention also relates to monoalkyltriazene combi-molecules having enhanced in vivo bioavailability. Monoalkyltriazene combi-molecules are unstable molecules with half-lives in the 40-50 min range. In order to enhance their in vivo bioavailability, the development of stable combi-molecules like JFC32, requiring metabolic activation was investigated. Examples of such "combi-molecules" having enhanced in vivo bioavailability are illustrated by the general structures shown below in Scheme 18.

Scheme 18

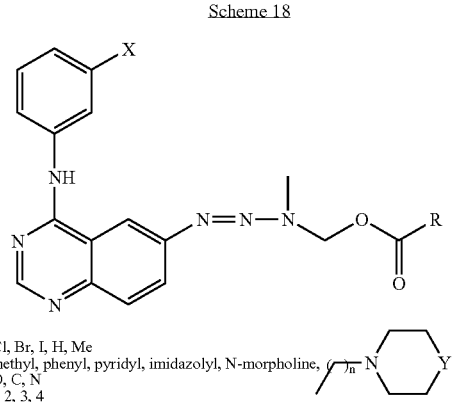

X = Cl, Br, I, H, Me
R = methyl, phenyl, pyridyl, imidazolyl, N-morpholine,
Y = O, C, N
n = 1, 2, 3, 4

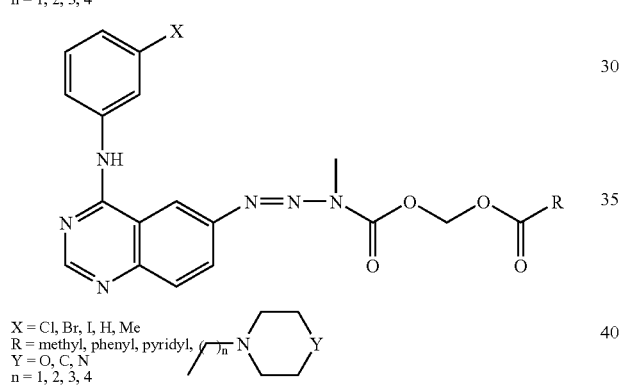

X = Cl, Br, I, H, Me
R = methyl, phenyl, pyridyl,
Y = O, C, N
n = 1, 2, 3, 4

Recently, RB108 was synthesized and was designed to release FD105 and a methyldiazonium species upon metabolic oxidation in vivo as outlined below in Scheme 19. Previous studies by Vaughan et al. (30) have shown that methoxymethyltriazenes of the benzotriazene class are activated in vivo to generate significant antitumor activity in murine tumor models.

Scheme 19

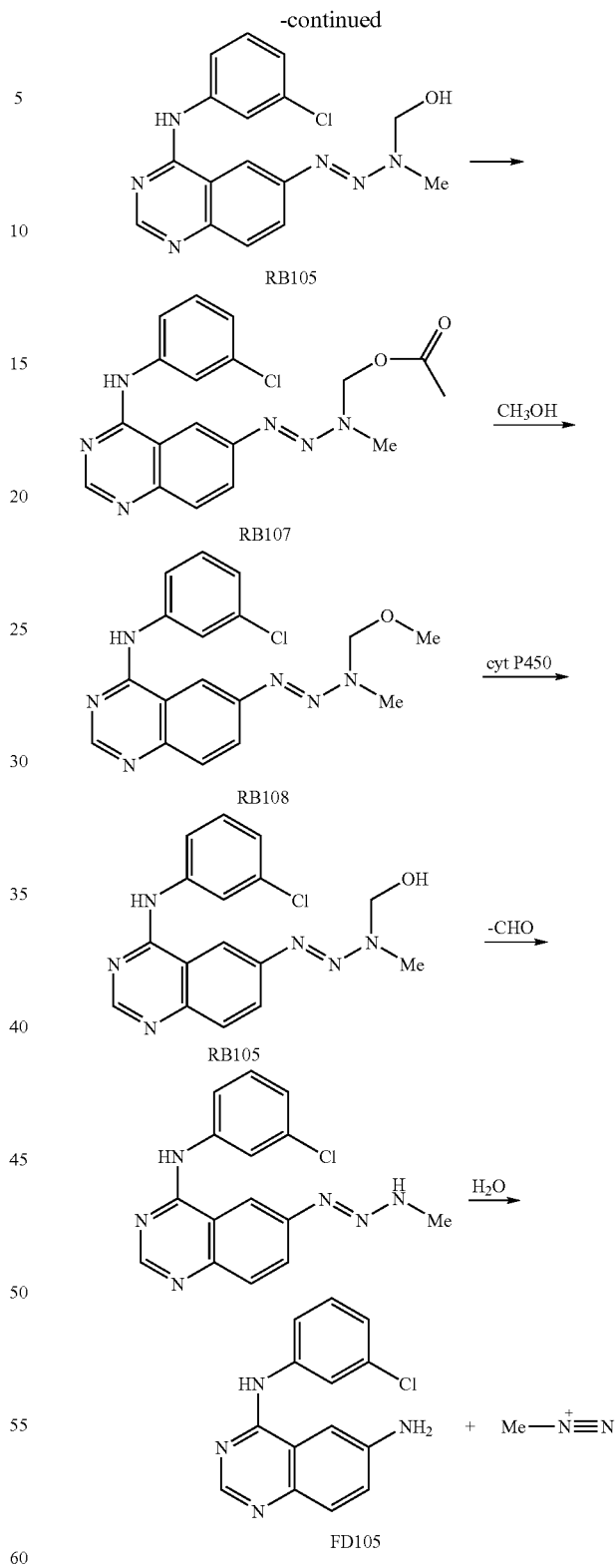

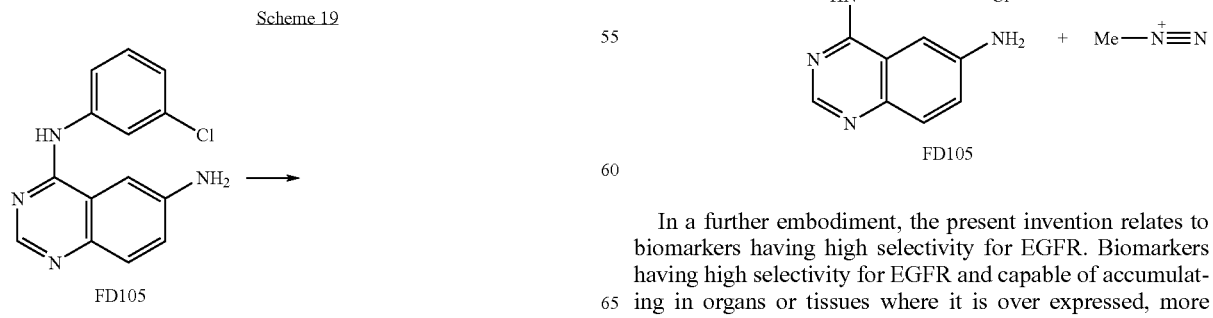

In a further embodiment, the present invention relates to biomarkers having high selectivity for EGFR. Biomarkers having high selectivity for EGFR and capable of accumulating in organs or tissues where it is over expressed, more specifically in cancer, constitute an important novel diagnostic tool. Tumors that concentrate the biomarker, due to an overexpression of EGFR, could thus be rapidly identified and located, and selected for EGFR-targeted therapies, both with immunotherapy or with small molecule inhibitors.

In an embodiment, the present invention relates to biomarkers having high selectivity for EGFR. There is an increasing need to incorporate diagnostics into clinical studies of EGFR-targeted therapies. Therefore, biomarkers having high selectivity for EGFR and which could accumulate in organs or tissues where it is over expressed, more specifically in cancer, are urgently needed. Patients with tumors that concentrate the biomarker could be selected for EGFR-targeted therapies, both with immunotherapy or with small molecule inhibitors.

Materials and Methods

Drug Treatment: FD105, ZR01 and PD168393 were synthesized according to published procedures (9, 14, 22). ZR2002 and ZR2003 were synthesized as described by Rachid et al. (31). In all assays, drug was dissolved in DMSO and subsequently diluted in RPMI-1640 containing 10% fetal bovine serum (FBS) (Wisent Inc. St-Bruno, Canada) or in DMEM containing 10% FBS immediately before the treatment of cell cultures. In all assays, the concentration of DMSO never exceeded 0.2% (v/v).

Cell Culture: The cell lines used in this study, the human breast carcinomas MDA-MB-468, MDA-MB-231 and MDA-MB-453 were obtained from the American Type Culture Collection (Manassas, Va., USA). The mouse fibroblasts NIH3T3HER14 (NIH3T3 cells stably transfected with EGFR gene) and the EGFR transfectant MDA-MB-231EGFR were generous gifts from Dr. Moulay Aloui-Jamali of the Montreal Jewish General Hospital. The MDA-MB-468 cells were maintained in RPMI-1640 supplemented with 10% FBS and antibiotics. The EGFR transfectant MDA-MB-231EGFR were maintained in RPMI-1640 supplemented with FBS (10%), antibiotics and HEPES (12.5 mM) (Wisent, St. Bruno, Canada). The MDA-MB-453 and NIH3T3HER14 cells were maintained in DMEM supplemented with 10% FBS and antibiotics. The mouse fibroblast cell line NIH3T3, its stable EGFR transfectant NIH3T3HER14 and its ErbB2 transfectant NIH3T3neu were maintained in DMEM supplemented with FBS (10%), antibiotics and HEPES (12.5 mM). All cells were maintained in 5% $CO_2$ atmosphere at 37° C.

Kinase assays: The EGFR kinase assay is similar to the one described in previously published procedures (19, 20). Nunc Maxisorp 96-well plates were incubated overnight at 37° C. with 100 µl/well of 0.25 mg/ml poly (L-glutamic acid-L-tyrosine, 4:1) PGT in PBS. Excess PGT was removed and the plate was washed three times with wash buffer (Tween 20 (0.1%) in PBS). The kinase reaction was performed by using 4.5 ng/well EGFR affinity-purified from A431 cells. The compound was added and phosphorylation initiated by the addition of ATP 50 µM. After 8 min at room temperature with constant shaking, the reaction was terminated by aspiration of the reaction mixture and rinsing the plate four times with wash buffer. Phosphorylated PGT was detected following 25 min incubation with 50 µl/well of HRP-conjugated PY20 anti-phosphotyrosine antibody (Santa Cruz Biotechnology, CA) diluted to 0.2 mg/ml in blocking buffer (3% bovine serum albumin; 0.05% Tween 20 in PBS). Antibody was removed by aspiration, and the plate washed four times with wash buffer. The signals were developed by the addition of 50 µl/well of 3,3',5,5'-tetramethylbenzidine peroxidase substrate and following blue color development, 50 µl of $H_2SO_4$ (0.09 M) was added per well, and plates were read at 450 nm using a Bio-Rad ELISA reader (model 2550).

UV fluorescence microscopy analysis: Cells were grown on 2-well chamber slides (Nalge Nunc, Naperville, Ill.) for 24 h until confluency and then incubated with 25 µM ZR2002 or 25 µM ZR1 for 30 min. Thereafter, the cells were washed with PBS and fixed with formaldehyde (3.7% formaldehyde in PBS; 1 mM $MgCl_2$) for 30 min at room temperature. The slides were subsequently washed 3 times with PBS containing 1 mM $MgCl_2$, and cover slips were added using the slow fade light antifade kit (Molecular Probes, Eugene, Oreg.). The slides were examined under a UV fluorescence microscope (magnification 250×) with an excitation at a wavelength of 340 nm.

Autophosphorylation assay: Inhibition of receptor autophosphorylation in viable cells was determined by anti-phosphotyrosine Western blots as previously described (19). Briefly, serum starved cells were pre-incubated for 2 h with the indicated concentrations of ZR2002 prior to stimulation with EGF or heregulin. Equal amounts of cell lysates were analyzed by Western blot using anti-phosphotyrosine antibodies. Membranes were stripped of anti-phosphotyrosine and reprobed with anti-EGFR or anti-erbB2 antibodies (Neo-Markers, Fremont, Calif.). To study whether an inhibition is reversible or not, duplicate sets of cells were treated with 2 µM of designated compound for 2 h. One set of cells was then stimulated with EGF. The other set of cells was washed free of the compound with warmed serum-free media, incubated for 2 h, washed again, incubated for another 2 h, and incubated for a further 4 h after a subsequent wash. This set of cells was then stimulated with EGF. Western blot was performed as previously described. For the study of inhibition of mitogene-activated protein kinase (MAPK) activation by ZR2002, protein lysates were obtained and Western blot was performed as described (23). The membrane was incubated with anti-phosphorylated MAPK (Erk1,2) or anti-Erk 1,2 antibodies (Cell Signaling Technology Inc., Beverly, Mass.).

Autophosphorylation assay (ZR2003): MDA-MB-468 cells were preincubated in a 6-well plate with serum-free media for 18 h, after which they were exposed to the indicated concentrations of ZR2003 for 2 h and subsequently treated with 100 ng/ml EGF for 10 min. Equal amounts of cell lysates were analyzed by Western blotting using anti-phosphotyrosine antibodies (NeoMarkers, Fremont, Calif.). The membrane was stripped, and reprobed with anti-EGFR antibodies (NeoMarkers).

In vitro growth inhibition assay: To study the effect of the compounds on growth factor stimulated-proliferation, cells were grown to 70% of confluence in 48-well plates. They were subsequently washed twice with PBS, incubated in serum-free medium for 18 h and exposed to each drug+growth factors (EGF, TGFα, PDGF or serum) for 72 h. Cell growth was measured using the sulforhodamine B (SRB) assay (24). Briefly, following drug treatment, cells were fixed using 50 µl of cold trichloroacetic acid (50%) for 60 min at 4° C., washed five times with tap water, and stained for 30 min at room temperature with SRB (0.4%) and dissolved in acetic acid (0.5%). The plates were rinsed five times with 1% acetic acid and allowed to air dry. The resulting colored residue was dissolved in 200 µl of Tris base (10 mM), and the optical density read for each well at 450 nm using a Bio-Rad microplate reader (model 2550). To study the reversibility of the antiproliferative effect of ZR2002, cells were exposed to each drug for 2 h, after which they were allowed to recover for 120 h in drug free medium, or continuously for 120 h. To study the reversibility of the antiproliferative effect of ZR2003 and FD105, MDA-MB-468 cells were preincubated in 96-well plates to approximately 70% of confluence and exposed to each drug for 2 h, after which they were allowed to recover for 120 h in drug free medium, or continuously for 120 h. The antiproliferative effect of ZR2002 and ZR2003 in isogenic mouse fibroblast cells NIH3T3, NIH3T3HER14, NIH3T3neu were studied by growing cells in 96-well plates to approximately 70% of confluence and exposing them to each drug for 120 h. Cell growth was measured using SRB assay as described previously.

Annexin V Binding: Cells were grown in 6-well plates until confluence and then incubated with the compounds for 24 h, 48 and 72 h. The cells were then harvested, washed twice with PBS, and centrifuged. Cells ($10^5$) were treated with annexin V-FITC and propidium iodide (PI) using the Apoptosis Detection Kit (BD Bioscience Pharmingen, USA) and the supplier's protocol. Annexin V-FITC and PI binding were analyzed by flow cytometry. Data were collected using logarithmic amplification of both the FL1 (FITC) and FL2 (PI) channels. Quadrant analysis of co-ordinate dot plots was performed with CellQuest software. Unstained cells were used to adjust the photomultiplier voltage and for compensation setting adjustment in order to eliminate spectral overlap between the FL1 and FL2 signals.

Alkaline Comet Assay for quantization of DNA damage: The alkaline comet assay was performed as described in previously published procedures (19, 20). The cells were exposed to drugs for 2 h, harvested with trypsin-EDTA and re-suspended in PBS. Cell suspensions were diluted to approximately $10^6$ cells, and mixed with agarose (1%) in PBS at 37° C. in a 1:10 dilution. The gels were cast on Gelbond strips (Mandel Scientific, Canada) using gel casting chambers and then immediately placed into a lysis buffer [2.5 M NaCl, 0.1 M tetra-sodium EDTA, 10 mM Tris-base and 1% (v/v) Triton X-100, pH 10.0]. After being kept on ice for 30 min, the gels were gently rinsed with distilled water and immersed in a second lysis buffer (2.5 M NaCl, 0.1 M tetra-sodium EDTA, 10 mM Tris-base) containing 1 mg/ml proteinase K for 60 min at 37° C. Thereafter, the gels were rinsed with distilled water, incubated in alkaline electrophoresis buffer for 30 min at 37° C., and electrophoresed at 19 V for 20 min. The gels were subsequently rinsed with distilled water and placed in 1 M ammonium acetate for 30 min. Thereafter, they were soaked in 100% ethanol for 2 h, dried overnight, and stained with SYBR Gold (1/10,000 dilution of stock supplied from Molecular Probes, Eugene, Oreg.) for 20 min. Comets were visualized at 330× magnification and DNA damage was quantitated using the Tail Moment parameter (i.e., the distance between the barycenter of the head and the tail of the comet multiplied by the percentage of DNA within the tail of the comet). A minimum of 50 cell/comets were analyzed for each sample, using ALKOMET version 3.1 image analysis software.

In vivo studies: SCID mice were maintained as per McGill animal safety protocols. In a preliminary model, SCID mice housed in filtered cages were implanted subcutaneously (s.c.) with the human breast carcinoma MDA-MB-468 and treatment began when the tumors were palpable (8 mice/group). ZR2002 at its tolerated dose (50 mg/kg) was delivered by intraperitoneal (i.p.) in a solution of aqueous cremaphore (25%)/ethanol (25%) (0.2 ml) every 3-4 days for one month. The tumor burdens were measured with a caliper and mice were weighed twice weekly. The study was later repeated with the MDA-MB-468 cells implanted in the mammary fat pad, a model that better mimics human breast carcinoma. ZR2003 or FD105 at 5 mg/kg was given i.p. every 3-4 days for one month. The vehicle was diluted to 0.4 ml (cremaphore (12.5%)/ethanol (12.5%) allowing a decrease of the cremaphore/ethanol concentration. Statistical analysis was carried using Student's t test with two tailed.

Results

The effects of the combi-molecule ZR2002 are compared with those of the corresponding free amine ZR01 and PD168393 (Scheme 1), a known irreversible inhibitor of EGFR (13). The results showed that in contrast to ZR01, ZR2002 is a molecule that cumulates multiple antitumor properties. It is an irreversible inhibitor of EGFR with marked DNA damaging properties and superior cytotoxic activity when compared with PD168393. In addition, ZR2002 being a fluorescent molecule, its sub-cellular distribution by UV fluorescence microscopy was examined. The results indicated that the fluorescence intensity/cell increased with increasing levels of EGFR (31). Moreover, using UV fluorescence microscopy, the sub-cellular localization of ZR2002 was analyzed. Despite its DNA damaging property and the ability of the entire molecule to remain bound to its target macromolecules, ZR2002 was concentrated in the perinuclear region, a distribution that parallels that of the non-covalently bound ZR01. This localization could be attributed to the binding of ZR2002 to nascent or maturing EGFR in the golgi and endoplasmic reticulum. Indeed, transfection of the MDA-MB-231 cells with EGFR increases the observed fluorescence intensity in the perinuclear region of the cells. Recent flow cytometric analysis of cells engineered to express fusion proteins of EGFR with the green fluorescence protein (GFP) showed a similar perinuclear localization of EGFR (32). However, it was shown that this did not reflect EGFR distribution in vivo and that redistribution in the perinuclear region was caused by Mowiol, an antifading agent commonly employed in the fixation and mounting processes (32). Nevertheless, since redistribution does not affect the overall EGFR content of the cells, the microscopy detection of increased EGFR content may account for the differences of fluorescence intensities observed by the UV fluorescence microscopy.

Overexpression of EGFR and its related oncoprotein p185neu, the erbB2 gene product, is considered the hallmark of many solid tumors including breast cancer, glioma, laryngeal cancer, squamous cell carcinoma of the head and neck, prostate and ovarian cancers. More importantly, it has become clear that receptors of the erbB family can intensify their transforming signal by forming homo- or heterodimers. Co-expression of these oncogenes is now associated with shortened survival times and increased relapse rates. The development of specific inhibitors of these oncoproteins has become one of the most active fields of research of this century.

Despite the selectivity of the current inhibitors introduced in clinical trial, response rates in patients remain rather moderate and combinations of these inhibitors with classical cytotoxic agents is presently considered a useful alternative. Within the same line of thought, it was recently demonstrated that combi-molecules with binary EGFR targeting/DNA damaging properties and with the ability to be hydrolyzed to another EGFR inhibitor, induced sustained antiproliferative activity in cells overexpressing EGFR (19, 20, 21, 22).

By appending a chloroethyl group to the 6-position of the quinazoline backbone, ZR2002 was designed to inhibit EGFR TK via its quinazoline moiety, and to damage DNA by its alkylating chloroethyl function. Its antiproliferative properties were compared to those of the Michael acceptor-containing inhibitor PD168393 and ZR01, a structurally related quinazoline that lacks the alkylating (chloroethyl) moiety. It was surmised that the 6-(2-chloroethyl)amino group, being a reactive functional group, may react with a cystein residue in the ATP binding site of EGFR, thereby irreversibly inhibiting the receptor. Indeed, Fry et al. (13) and Smaill et al. (14)

demonstrated that acryloyl moieties attached to the 6-position of quinazoline reacted with cystein 773 of EGFR, leaving an irreversibly inhibited receptor. The chloroethyl group of ZR2002, being appended to the same position and being sufficiently reactive to damage DNA, is likely to react with the thiol group of the cystein 773 residue through an $S_N2$ substitution reaction. While the characterization of the alkylated cystein residue was not carried out, it is important to note that the protracted inhibition of EGFR autophosphorylation by ZR2002 is in line with its putative ability to covalently damage the receptor.

In contrast to ZR2002, that partially lost its antiproliferative activities after a 2 h pulse exposure and 120 h recovery, ZR01 was totally inactive under these conditions, indicating that the chloroethyl group plays a significant role in the activity of the molecule. This property may be imputed to its dual ability to damage both the receptor itself and DNA. Its binary targeting properties may also account for its ability to induce apoptosis in MDA-MB-468 cells at a concentration as low as 5 µM. At this concentration, only barely detectable levels of apoptosis could be induced by ZR01 and PD168393 at all time points.

The sustained antiproliferative activity of ZR2002 may also result from a mechanistic interaction between its DNA damaging properties and its ability to block EGFR-mediated signaling. ZR2002 was shown to block MAPK phosphorylation whose activation is associated with c-fos gene expression and mitogenic effects (26, 27). More recently, blockade of MAPK activation using the small molecule inhibitor PD98059 was shown to sensitize ovarian cancer cells to DNA damaging agents, suggesting that the latter signaling protein may be involved in a DNA repair pathway or other mechanism of resistance to DNA damaging agents (28). Furthermore, Yakoub et al. (29) recently demonstrated that EGF up-regulates the DNA repair genes XRCC1 and ERCC1 in prostate cell lines through MAPK signaling. Thus, blockade of EGF-induced signal transduction by the EGFR TK inhibitory effect of ZR2002 may down-regulate DNA repair activities required to rescue the cells, thereby enhancing the cytotoxic effects of the concomitantly induced DNA lesions.

The in vivo antitumor activity of ZR2002 was tested using mice bearing subcutaneously implanted MDA-MB-468 cells. The results showed that ZR2002 (p<0.001) was significantly potent. However, its antitumor activity remained modest in this model. It was surmised that this was due to its reduced water solubility which is in line with the poor solubility associated with 3'-bromoanilino compounds.

The in vitro and in vivo antitumor activities of ZR2003, the 3'chloro analogue of ZR2002, were studied in EGFR-overexpressing MDA-MB-468 human breast cancer cells. ZR2003 is more hydro-soluble than its 3'bromo analogue ZR2002. In vitro studies demonstrated that ZR2003 exhibited EGFR inhibitory properties both in enzyme and in whole cell assay. The observed results parallel those observed for ZR2002. Moreover, ZR2003 exhibits a similar cytotoxicity profile to ZR2002. Indeed, in contrast to ZR2003 that partially lost its antiproliferative activities after a 2 h drug exposure and 120 h recovery, its free counterpart FD105 was totally inactive under these conditions, indicating, as previously observed for ZR2002, that the chloroethyl group plays a significant role in the activity of the molecule. This property may be imputed to its dual ability to damage both the receptor itself and DNA. Indeed, in a previous study it was shown that ZR2002 induced irreversible inhibition of EGF-stimulated autophosphorylation in MDA-MB-468 cells, suggesting that ZR2002 may alkylate the EGFR (33). The binary targeting properties of ZR2003 may also account for its ability to induce significantly higher levels of cell death by apoptosis than the non chloroethyl containing analogue FD105. ZR2003 was tested in vivo in SCID mice having MDA-MB-468 cells implanted in their mammary fat pad. The fact that ZR2003 was significantly more potent than ZR2002 may be due to its superior hydro-solubility. However, its significantly greater potency (p<0.05) when compared to FD105 must be attributed to its superior cytotoxicity.

ZR2002 and ZR2003 thus constitute a prototype of combi-molecules that may directly alkylate EGFR and DNA without the requirement for hydrolytic activation. ZR2002 does not only block EGF-induced signaling but also inhibits heregulin-induced autophosphorylation, suggesting that it may also be an inhibitor of the HER2 gene product. Thus, this is an example of a new class of molecules capable of blocking cell signaling mediated by different members of the erbB family while inflicting cytotoxic DNA damage, a mechanism that may induce significant antiproliferative activity in refractory tumors.

Example 1

Synthesis of ZR2002

The amino compound (1.26 g, 0.4 mmol) was stirred in dry acetonitrile (40 mL) under argon, after which the solution was cooled to −5° C. followed by the addition of nitrosonium tetrafluoroborate (0.9 g, 0.8 mmol) in acetonitrile. The resulting clear solution was stirred for 1 hour at −5° C. to permit the formation of the diazonium salt. It was then added dropwise to another solution of ether (30 mL), water (5 mL), and $Et_3N$ (6 ml) and 2-chloroethylamine hydrochloride (3.24 g, 2.8 mmol) at 0° C. The mixture was stirred at room temperature overnight followed by the subsequent extraction with ethyl acetate. The organic layer was dried over potassium carbonate and evaporated to provide the crude product which was purified by chromatography using a basic alumina column (1:4 triethylamine-AcOEt) to give an oil that solidified upon addition of petroleum ether and ether to give (400 mg, 27%) of ZR2002; mp 167° C.; ESI m/z 377.3 ($MH^+$ with $^{79}Br$), 379.2 ($MH^+$ with $^{81}Br$), 381.2 ($MH^+$ with $^{81}Br$, $^{37}Cl$), 341.3 (M-Cl, 16.68); $^1H$ NMR (400 MHz, DMSO-d6) δ 9.48 (s, 1H, NH), 8.39 (s, 1H, H-2), 8.12 (s, 1H, H-2'), 7.86 (dd, 1H, J=1.2 Hz, J=10.8 Hz, H-6'), 7.55 (1H, d, J=12.4 Hz, H-8), 7.36-7.25 (m, 4H, H-5-7-4'-5'), 6.52 (t, 1H, J=8 Hz NH), 3.85 (t, 2H, J=7.6 Hz, $CH_2$—Cl), 3.62 (q, 2H, J=8 Hz, $CH_2$); $^{13}C$ NMR (100 MHz, DMSO-d6) δ 156.4, 150.3, 147.5, 143.0, 141.9, 131.0, 129.0, 126.4, 124.9, 124.8, 121.8, 121.5, 117.1, 97.6, 45.6, 43.9.

Example 2

Synthesis of ZRBA1 (1-{4-[(3-Chlorophenyl)amino-6-quinazolinyl}-3-(2-N,N-dimethylaminoethyl)triazene)

The amino compound (500 mg, 1.70 mmol) was stirred in dry acetonitrile (15 mL) under argon, after which the solution was cooled to −5° C. followed by the addition of nitrosonium tetrafluoroborate (430 mg, 3.70 mmol) in acetonitrile. The resulting clear solution was stirred for 1 hour at −5° C. to permit the formation of the diazonium salt. It was then added dropwise to another solution of ether (20 mL), water (3 mL), and $Et_3N$ (1 ml) and N,N-dimethylethylenediamine (1.50 ml, 11.90 mmol) at 0° C. The mixture was stirred at room temperature overnight followed by the subsequent extraction with ethyl acetate. The organic layer was dried over potassium carbonate and evaporated to provide the crude product which was purified by chromatography using a basic alumina column (1:3 triethylamine-AcOEt) to give an oil that solidified upon addition of petroleum ether and ether to give (200 mg, 29%) of ZRBA1; mp 150° C.; $^1$H NMR (400 MHz, DMSO-d6) δ 10.63 (br, s, 1H, N=N—NH), 9.89 (s, 1H, NH), 8.57 (s, 1H, H-5), 8.41 (s, 1H, H-2), 8.14 (s, 1H, H-2'), 7.94 (d, 1H, J=8.8 Hz, H-7), 7.87 (d, 1H, J=8.8 Hz, H-8), 7.75 (d, 1H, J=9.5 Hz, H-4'), 7.38 (t, 1H, J=9.5 Hz, H-5'), 7.13 (d, 1H, J=9.5 Hz, H-6'), 3.66 (br, 2H, CH$_2$), 2.56 (t, 2H, J=8.6 Hz, CH$_2$), 2.19 (s, 6H, 2×CH$_3$); $^{13}$C NMR (100 MHz, DMSO-d6) δ 157.1, 152.8, 148.8, 147.8, 141.0, 130.1, 128.6, 125.5, 124.6, 123.8, 121.0, 120.3, 115.5, 114.4, 55.3, 45.2 (2 C overlap), 41.5.

Example 3

Synthesis of ZRBA2 (1-{4-[(3-Chlorophenyl)amino-6-quinazolinyl}-3-(2-pyrrolidinoaminoethyl)triazene)

The amino compound (100 mg, 0.37 mmol) was stirred in dry acetonitrile (5 mL) under argon, after which the solution was cooled to −5° C. followed by the addition of nitrosonium tetrafluoroborate (86 mg, 0.74 mmol) in acetonitrile. The resulting clear solution was stirred for 1 hour at −5° C. to permit the formation of the diazonium salt. It was then added dropwise to another solution of ether (10 mL), water (1 mL), and Et$_3$N (0.36 ml) and 1-(2-aminoethyl)pyrrolidine (0.32 ml, 2.59 mmol) at 0° C. The mixture was stirred at room temperature overnight followed by the subsequent extraction with ethyl acetate. The organic layer was dried over potassium carbonate and evaporated to provide the crude product which was purified by chromatography using a basic alumina column (1:4 triethylamine-AcOEt) to give an oil that solidified upon addition of petroleum ether and ether to give (40 mg, 30%) of ZRBA2; mp 145° C.; $^1$H NMR (400 MHz, DMSO-d6) δ 10.65 (br, s, 1H, N=N—NH), 9.89 (s, 1H, NH), 8.58 (s, 1H, H-5), 8.42 (s, 1H, H-2), 8.14 (s, 1H, H-2'), 7.94 (d, 1H, J=8.8 Hz, H-7), 7.87 (d, 1H, J=8.8 Hz, H-8), 7.75 (d, 1H, J=9.2 Hz, H-4'), 7.39 (t, 1H, J=8.0 Hz, H-5'), 7.13 (d, 1H, J=8.0 Hz, H-6'), 3.68 (br, 2H, CH$_2$), 2.74 (br, 2H, CH$_2$), 1.69 (br, s, 8H, CH$_2$).

Example 4

Synthesis of ZRBA4 (1-{4-[(3-Chlorophenyl)amino-6-quinazolinyl}-3-{2-[N-(2-chloroethyl)-N-methylethylenamine]}triazene)

The amino compound (140 mg, 0.5 mmol) was stirred in dry acetonitrile (5 mL) under argon, after which the solution was cooled to −5° C. followed by the addition of nitrosonium tetrafluoroborate (121 mg, 1.0 mmol) in acetonitrile. The resulting clear solution was stirred for 1 hour at −5° C. to permit the formation of the diazonium salt. It was then added dropwise to another solution of ether (6 mL), water (0.5 mL), and Et$_3$N (0.85 ml) and N-(2-chloroethyl)-N-methylethylenediamine (340 mg, 2.0 mmol) at 0° C. The mixture was stirred at room temperature overnight followed by the subsequent extraction with ethyl acetate. The organic layer was dried over potassium carbonate and evaporated to provide the crude product which was purified by chromatography using a basic alumina column (AcOEt) to give an oil that solidified upon addition of petroleum ether and ether to give (30 mg, 15%) of ZRBA4; mp 150° C.; $^1$H NMR (400 MHz, DMSO-d6) δ 10.6 (br, s, 1H, N=N—NH), 9.88 (s, 1H, NH), 8.58 (s, 1H, H-5), 8.42 (s, 1H, H-2), 8.14 (s, 1H, H-2'), 7.94 (d, 1H, J=8.6 Hz, H-7), 7.88 (d, 1H, J=8.6 Hz, H-8), 7.75 (d, 1H, J=8.0 Hz, H-4'), 7.38 (t, 1H, J=8.0 Hz, H-5'), 7.13 (d, 1H, J=8.0 Hz, H-6'), 3.67 (br, 4H, CH$_2$), 2.75 (br, 4H, CH$_2$), 2.31 (s, 3H, CH$_3$); ESI m/z 418.1 (MH$^+$ with $^{35}$Cl, $^{35}$Cl), 420.1 (MH$^+$ with $^{35}$Cl, $^{37}$Cl), 422.1 (MH$^+$ with $^{37}$Cl, $^{37}$Cl).

Example 5

Synthesis of RB108 [6-(3-methoxymethyl-3-methyl-triazenyl)-4-(3'-chlorophenyl-amino)quinazoline]

To a solution of 4-(3'-chlorophenyl-amino)-6-amino-quinazoline (100 mg, 0.318 mmol) in acetonitrile (20 mL) kept at 0° C. in an ice bath, nitrosonium tetrafluoroborate (74.3 mg, 0.637 mmol) was added dropwise. The solution was stirred for 20 min and 0.9 mL of a mixture of methylamine 40% (0.075 mL, 0.954 mmol), formaldehyde 37% (0.75 mL, 9.54 mmol), and concentrated HCl (0.1 mL) was added all at once. The diazonium solution was subsequently alkalinized with potassium carbonate (400 mg, 2.86 mmol) and the precipitate was filtered to give a white solid contaminated with excess potassium carbonate. The precipitate was therefore re-suspended in THF and the resulting solution filtered. The organic solvent was further evaporated to give 6-(3-hydroxymethyl-3-methyl-triazenyl)-4-(3'-chlorophenyl-amino)quinazoline as a pure brown solid (90 mg, 73%). 6-(3-Hydroxymethyl-3-methyl-triazenyl)-4-(3'-chlorophenyl-amino)quinazoline (100 mg, 0.258 mmol) was dissolved in pyridine (2 mL) after which acetic anhydride (0.055 mL, 0.516 mmol) was slowly added. The solution was further kept on ice for 1.5 h and the pyridine evaporated as an azeotrope with toluene to give 6-(3-Acetoxymethyl-3-methyl-triazenyl)-4-(3'-chlorophenyl-amino)quinazoline as a pure brown residue (105 mg, 95%). 6-(3-Acetoxymethyl-3-methyl-triazenyl)-4-(3'-chlorophenyl-amino)quinazoline (100 mg, 0.260 mmol) was dissolved in anhydrous methanol (2.5 mL) and stirred at room temperature for 24 h. The methanol was then evaporated to provide the title compound 6-(3-methoxymethyl-3-methyl-triazenyl)-4-(3'-chlorophenyl-amino) quinazoline) as a pure brown residue (91 mg, 98%): EI m/z 357.0 (MH$^+$), 253.2 (M-3-methoxymethyl-3-methyl-triazene); $^1$H NMR (400 MHz, DMSO-d6) d 9.94 (s, 1H, NH), 8.60 (s, 1H), 8.54 (s, 1H), 8.14 (s, 1H), 8.01 (d, 1H, J=9.2 Hz), 7.88 (d, 1H, J=6.8 Hz), 7.79 (d, 1H, J=9.2 Hz), 7.39 (t, 1H, J=6.6 Hz), 7.14 (d, 1H, J=9.2 Hz), 5.17 (s, 2H, CH$_2$), 3.25 (s, 3H, CH$_3$,), 3.24 (s, 3H, CH$_3$).

Example 6

Synthesis of o-Xylenediamine (2)

A suspension of sodium hydride (0.55 g, 22.9 mmol, 2.3 eq.) and t-butyl iminocarboxylate (4.94 g, 22.7 mmol, 2.3 eq.) in dry DMF was stirred at 60° C. for 6 h. Thereafter, α,α'-dibromo-o-xylene (2.64 g, 9.9 mmol, 1.0 eq.) was added and the resulting mixture heated at 60° C. for 4 h and diluted to 100-150 mL with water. The mixture was extracted with four 25-mL portions of methylene chloride. The crude oil left on removal of the solvents was cleaved by warming with 25 mL of concentrated hydrochloric acid to give diamine 2 as a hydrochloride hemihydrate (57%): mp 189-191° C.; $^1$H NMR (300 MHz, DMSO-d$_6$) δ 8.62 (br s, 6H, NH$_3$$^+$), 7.54-

7.57 (m, 2H, H-4.5), 7.40-7.43 (m, 2H, H-3.6), 4.14 (br d, 4H, J=4.8 Hz, $NH_3^+CH_2$), 3.48 (br s, 1H, H of hemihydrate).

Example 7

Synthesis of 2-[4-(2-aminoethyl)-piperazin-1-yl]-ethylamine (3)

Chloroacetonitrile (8.4 mL, 25.5 mmol, 2.0 eq.) in 125 mL of acetonitrile was added to piperazine (5.4 g, 62.5 mmol, 1.0 eq.) and anhydrous potassium carbonate (17.5 g, 25.5 mmol, 2.0 eq.) in 125 mL acetonitrile. The reaction mixture was stirred at room temperature overnight. The solid was removed by filtration and the solvent evaporated. The residue was crystallized from methanol to give the cyano intermediate as a white solid which was used directly in the next step (58%). The previously obtained cyano intermediate (3.0 g, 18.3 mmol, 1.0 eq.) in THF (50 mL) was slowly added to a suspension of lithium aluminum hydride (3.0 g, 78.9 mmol, 4.3 eq.) in THF (100 mL). The reaction mixture was refluxed for 3 h and then cooled. A potassium hydroxide solution (50%, 4.4 g of KOH) was carefully added and the resulting precipitate was removed by filtration through celite. Evaporation of the solvent provided diamine 3 as an oil in 80% yield. $^1$H NMR (300 MHz, $CDCl_3$) d 2.77 (t, 4H, J=6.2 Hz, $NH_2CH_2$), 2.47 (br s, 8H, H of piperazine), 2.41 (t, 4H, J=6.2 Hz, $NH_2CH_2CH_2$), 1.59 (br s, 4H, $NH_2$).

Example 8

Synthesis of $N^1$-{2-[(2-Aminoethyl)-methylamino]-ethyl}-$N^1$-methylethane-1,2-diamine (4)

Tetraamine 4 was prepared from N,N'-dimethylethylene-diamine (6.8 mL, 62.5 mmol) as described for 3 (78% from cyano intermediate). $^1$H NMR (300 MHz, $CDCl_3$) δ 2.75 (t, 4H, J=6.2 Hz, $NH_2CH_2$), 2.47 (s, 4H, $N(CH_3)CH_2CH_2N$ $(CH_3)$), 2.41 (t, 4H, J=6.2 Hz, $NH_2CH_2CH_2$), 2.23 (s, 6H, $NCH_3$), 1.72 (br s, 4H, $NH_2$).

Example 9

Synthesis of Double-Arm Combi-Triazenes 5-9; General Coupling Procedure

Amine 1 (Scheme 14) (0.27 g, 1.0 mmol, 1.0 eq.) was added to a $CH_3CN$ solution (5 mL) of $NOBF_4$ (0.19 g, 1.5 mmol, 1.5 eq.) and stirred for 15 min. at −5° C. In a separate flask, diamine spacer (0.5 mmol, 0.5 eq.) was dissolved in chloroform (50 mL) containing DIPEA (0.9 mL, 5.0 mmol, 5.0 eq.) [in case of 5, an additional 2 eq. of DIPEA were used to neutralize the hydrochloride salt of 2 (Scheme 13)]. The diazonium containing solution was added dropwise at −5° C. to the diamine solution and stirred for 5 min. prior to washing with water. The organic phase was dried over potassium carbonate and evaporated under reduced pressure without heating. The resulting solid was washed with diethyl ether and purified by chromatography using a basic alumina column (THF/water).

$^1$H NMR and MS data for double-arm combi-triazenes 5-9.

Double arm combi-triazene 5: $^1$H NMR (300 MHz, DMSO-$d_6$) d 10.97 (br s, 2H, N═N—NH), 9.80 (s, 2H, NH), 8.51 (s, 2H, H-5), 8.34 (s, 2H, H-2) 8.08 (s, 2H, H-2'), 7.90 (d, 2H, J=9.3 Hz, H-7), 7.81 (d, 2H, J=8.7 Hz, H-4'), 7.65 (d, 2H, J=9.3 Hz, H-8), 7.44 (m, 2H, H-b), 7.37 (br s, 4H, H-a), 7.34 (d, 2H, J=8.7 Hz, H-5'), 7.11 (d, 2H, J=8.7 Hz, H-6'), 4.87 (br s, 4H, $CH_2N$═N). ESIMS 699.0 (M+H$^+$).

Double arm combi-triazene 6: $^1$H NMR (300 MHz, DMSO-$d_6$) d 11.07 (br s, 2H, N═N—NH), 9.90 (s, 2H, NH), 8.57 (s, 2H, H-5), 8.43 (s, 2H, H-2), 8.12 (s, 2H, H-2'), 7.96 (d, 2H, J=9.7 Hz, H-7), 7.85 (d, 2H, J=9.7 Hz, H-8), 7.76 (d, 2H, J=9.7 Hz, H-4'), 7.38 (br s, 4H, H-a,b), 7.36 (d, 2H, J=8.7 Hz, H-5'), 7.13 (d, 2H, J=8.7 Hz, H-6'), 4.79 (br s, 4H, $CH_2N$═N). ESIMS 698.9 (M+H$^+$)

Double arm combi-triazene 8: $^1$H NMR (300 MHz, DMSO-$d_6$) d 10.67 (br s, 2H, N═N—NH), 9.84 (s, 2H, NH), 8.55 (s, 2H, H-5), 8.38 (s, 2H, H-2), 8.11 (s, 2H, H-2'), 7.89 (m, 2H, H-7), 7.86 (m, 2H, H-4'), 7.69 (br s, 2H, H-8), 7.36 (dd, J=9.3, 8.7 Hz, 2H, H-5'), 7.12 (d, J=6.3 Hz, 2H, H-6'), 3.66 (br s, 4H, $CH_2N$═N), 3.32 (m, 4H, $NCH_2CH_2N$), 2.71 (br s, 4H, $NCH_2$), 2.27 (s, 3H, $CH_3N$).

Double arm combi-triazene 9: $^1$H NMR (300 MHz, DMSO-$d_6$) δ 10.64 (br s, 2H, N═N—NH), 9.84 (s, 2H, NH), 8.56 (s, 2H, H-5), 8.40 (s, 2H, H-2), 8.12 (s, 2H, H-2'), 7.91 (d, 2H, J=9.0 Hz, H-7), 7.86 (d, 2H, J=8.6 Hz, H-4'), 7.73 (d, 2H, J=9.0 Hz, H-8), 7.37 (dd, 2H, J=8.6, 8.6 Hz, H-5'), 7.12 (ddd, 2H, J=8.6, 6.6, 2.3 Hz, H-6'), 3.70 (br s, 4H, $CH_2N$═N), 2.78 (dd, 4H, J=7.3, 7.3 Hz, $NCH_2$), 2.28 (s, 3H, $CH_3N$). ESIMS m/z=679.9 (M+H$^+$).

Example 10

Inhibition of EGFR TK Activity

Figure 18:
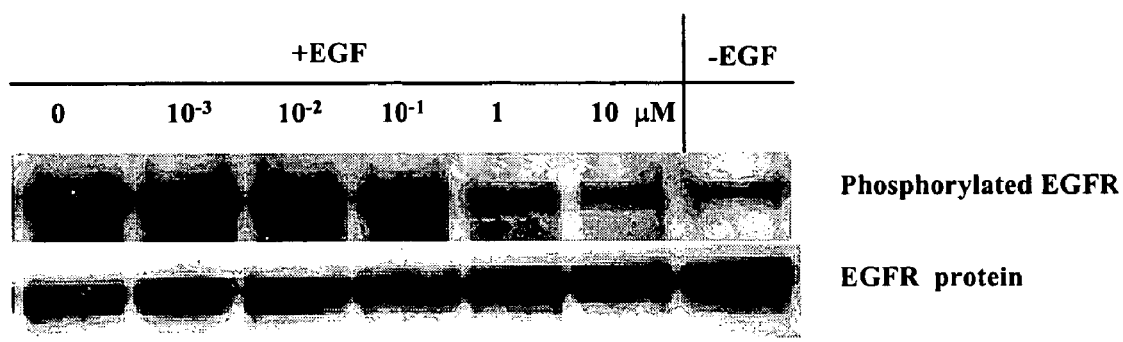
FIG. 18 shows the inhibition of EGFR autophosphorylation by ZR2003. Serum starved MDA-MB-468 cells were preincubated for 2 h with the indicated concentrations of ZR2003 prior to stimulation with 100 ng/ml EGF for 10 min. Equal amount of cell lysates was analyzed by western blot using anti-phosphotyrosine antibody. The membrane was stripped, and reprobed with anti-EGFR antibody.

The EGFR inhibitory properties of ZR2002 were compared with those of ZR01 and PD168393 in an ELISA inhibitory assay. ZR2002 ($IC_{50}$=0.01 μM) showed more than a 4-fold greater EGFR TK inhibitory activity than ZR01 ($IC_{50}$=0.04 μM) in this assay, indicating that the 2-chloroethyl moiety contributes to the enhancement of the EGFR inhibitory activity of the resulting structure. However, it was approximately 3-fold less potent than PD168393 ($IC_{50}$=0.0033 μM) (FIG. 1). ZR2003 ($IC_{50}$=0.026 μM), the 3-chloro analogue of ZR2002, was approximately 2.6-fold less active than ZR2002 but was 7.7-fold stronger EGFR TK inhibitory activity than its structural homologue FD105 ($IC_{50}$=0.2 μM). More importantly, Western blot analysis demonstrated that ZR2003 blocked EGF-induced EGFR autophosphorylation in MDA-MB-468 cells in a dose-dependent manner ($IC_{50}$=0.1 μM) without affecting the levels of EGFR (FIG. 18).

Example 11

Inhibition of EGFR Autophosphorylation

Figure 2:
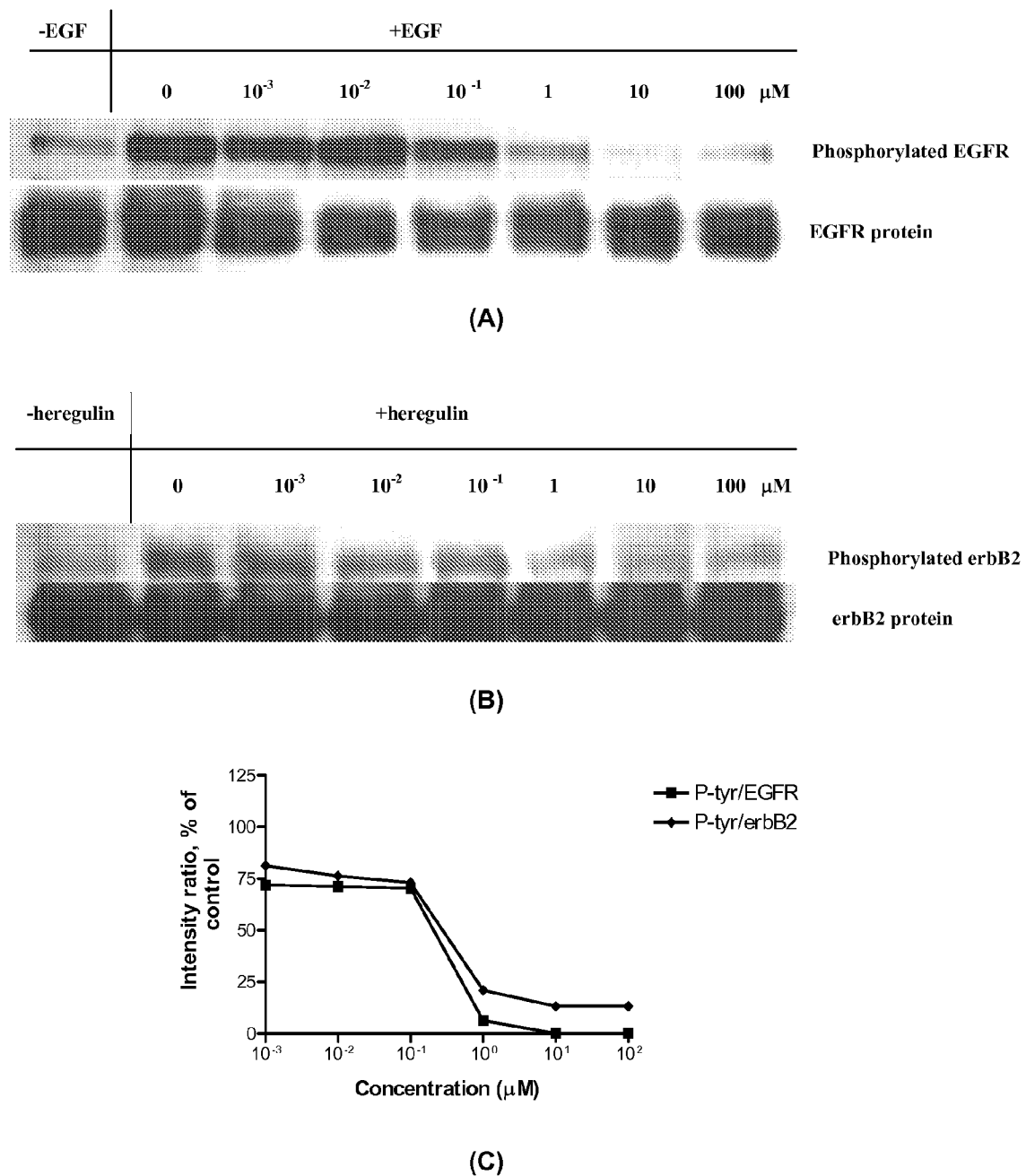
FIG. 2 shows the inhibition of EGFR and erbB2 autophosphorylation by ZR2002. Serum starved MDA-MB-468 cells (A) or MDA-MB-453 cells (B) were pre-incubated for 2 h with the indicated concentrations of ZR2002 prior to stimulation with EGF (A) for 10 min or heregulin (B) for 10 min. Equal amounts of cell lysates were analyzed by western blotting using anti-phosphotyrosine antibodies. Membranes were stripped of anti-phosphotyrosine and reprobed with anti-EGFR or anti-erbB2 antibodies. (C) Comparison of inhibition of EGFR and erbB2-autophosphorylation by ZR2002. The film was scanned and band intensities were measured using the SynGene GeneTools software package. Values are percentages of control of phosphotyrosine/EGFR and phosphotyrosine/erbB2. $IC_{50}$ for EGFR (0.241 μM) and $IC_{50}$ for erbB2 (0.236 μM).

While the enzyme assay is important for the determination of the receptor affinity of the compounds, the evaluation of EGF or heregulin-induced autophosphorylation of EGFR or the erbB2 gene product in whole cells remains the most significant test. Western blot analysis demonstrated that ZR2002 blocked EGF-induced EGFR autophosphorylation in MDA-MB-468 cells and also heregulin-induced autophosphorylation in MDA-MB-453 cells in a dose-dependent manner without affecting the levels of EGFR and erbB2, respectively (FIGS. 2A, B). Inhibitions of EGF and heregulin-induced autophosphorylations were equally blocked by ZR2002 with IC$_{50}$ values of around 0.23 µM (FIG. 2C), indicating that this compound may be active against other members of the EGFR family.

Example 12

Mechanism of EGFR Inhibition

Figure 3:
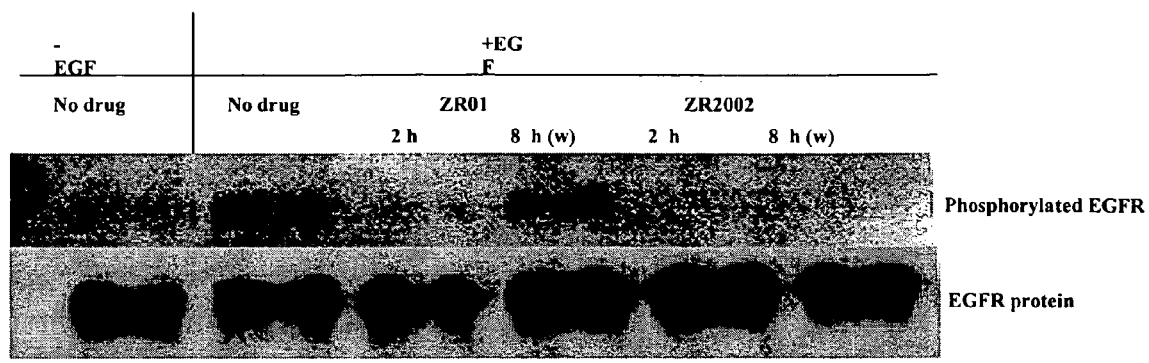
FIG. 3 shows the reverse EGFR autophosphorylation in the presence of ZR2002 or ZR01 in MDA-MB 468 cells. Duplicate sets of cells were treated with 2 μM of designated compound to be tested as a reversible EGFR inhibitor for 2 h. One set of cells was then stimulated with EGF. The other set of cells was stimulated with EGF after 8 h post treatment in drug free media and repeated washouts (8 h w). Western blotting was performed with an anti-phosphotyrosine antibody. The same membrane was stripped and EGFR detected with an anti-EGFR antibody.

Unlike ZR01, ZR2002 is a reactive molecule containing an alkylating chloroethyl group and capable of alkylating nucleophiles. It could therefore inflict some covalent damage to the ATP binding site of EGFR, thereby inducing irreversible inhibition. To test this hypothesis, the reversibility assay described by Fry et al. (13) and Smaill et al. (14) was used, according to which the cells are treated with inhibitors (2 µM) for 2 h and then washed free of drug. After 8 h, EGF was added; after a 10-min incubation the cells were lysed, and the degree of EGFR autophosphorylation measured. As expected, ZR2002 and ZR01 completely suppressed EGF-dependent EGFR autophosphorylation in MDA-MB-468 breast cancer cells immediately after drug exposure. However, at 8 h post-treatment in drug-free medium the reversible inhibitor ZR01 lost almost 95% of its inhibitory action (FIG. 3). Similar results have already been reported for PD168393 (13).

Example 13

Fluorescence Properties of ZR2002

Figure 4:
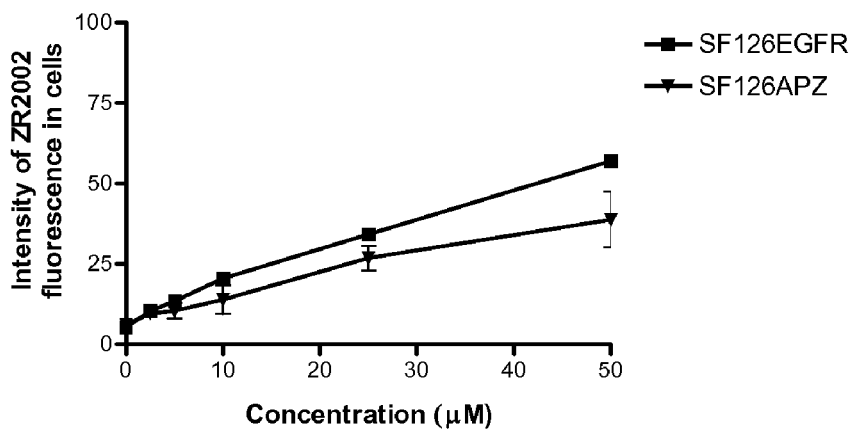
FIG. 4 shows the internalization of ZR2002 in cell lines with different EGFR levels. Cells were incubated with ZR2002 for 30 min and analyzed by flow cytometry (A, and B). Correlation between EGFR levels and fluorescence intensity of ZR2002 in cells [Pearson correlation, r=0.7 (P<0.02)] (C). Each point represents at least two independent experiments.
Figure 4:
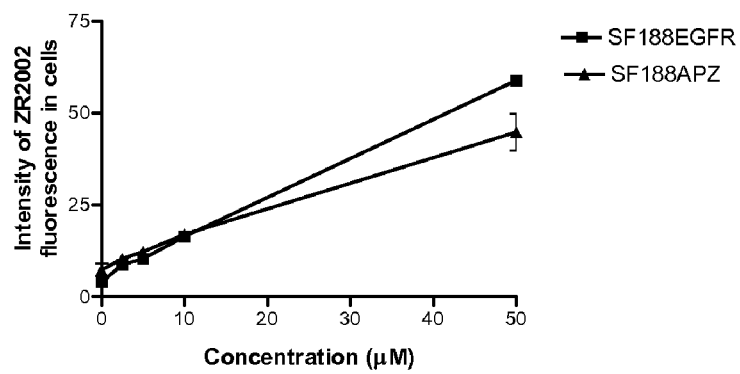
Figure 4:
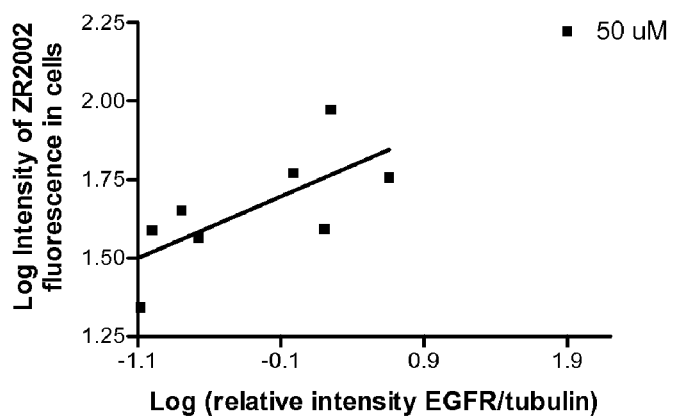
Figure 17:
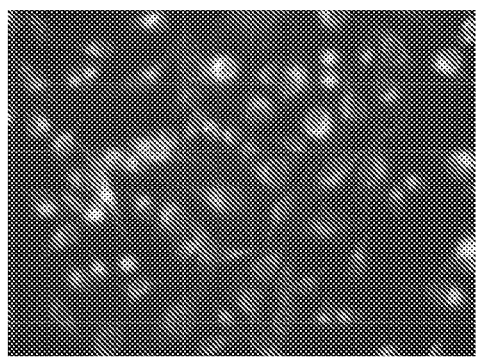
FIG. 17 shows the sub-cellular distribution of ZR2002 and ZR01. MDA-MB-231 (A) and MDA-MB-231EGFR (B) cells were incubated with ZR01 or ZR2002 for 30 min and examined under fluorescence microscopy (magnification 250×) with an excitation wavelength of 340 nm.
Figure 17:
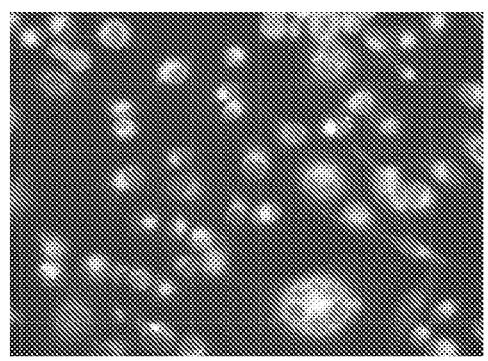
Figure 17:
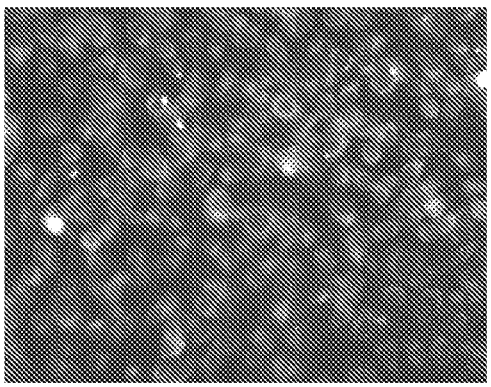
Figure 17:
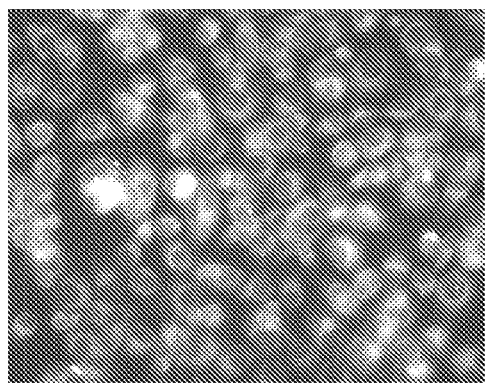

ZR2002 showed fluorescence properties (absorption 270 nm, emission 451 nm). These fluorescence properties were used to determine its selective internalization in EGFR transfected cells and cell lines with different EGFR levels by flow cytometry. The results showed that ZR2002 was more internalized in the transfected cells (FIGS. 4A, B) and a significant correlation existed between the EGFR level and the intensity of ZR2002 fluorescence inside the cells (Pearson correlation r=0.7, p<0.02) (FIG. 4C). Moreover, the results indicated that following cell exposure to ZR2002, the latter was preferentially localized in the perinuclear region as indicated by significant fluorescence intensities observed around the nuclei. Similar results were obtained with ZR01 (FIG. 17). In addition, the transfection of the MDA-MB-231 cells with EGFR increases the observed fluorescence intensity in the perinuclear region of the cells (FIG. 17).

Example 14

Antiproliferative Activity of ZR2002 and ZR2003

(a) Inhibition of Growth Factor-Stimulated Proliferation.

Figure 5:
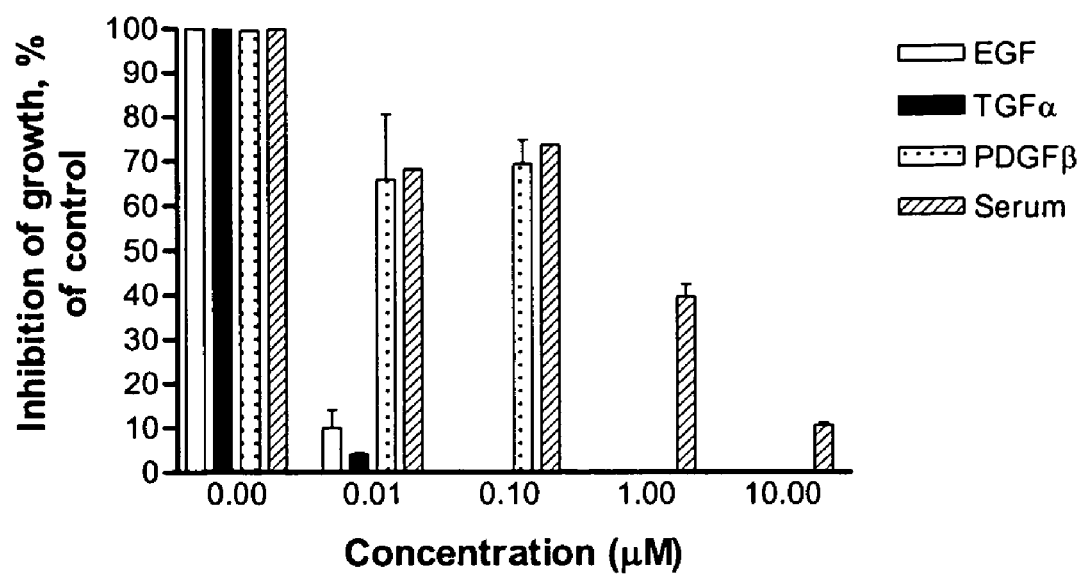
FIG. 5 shows the effect of ZR2002 on growth factor stimulated-proliferation in NIH3T3HER14 cells. Cells were exposed to ZR2002 and growth factors (EGF, TGFα, PDGFβ or serum) for 72 h. Cell growth was measured using SRB assay. Each point represents at least two independent experiments.
Figure 21:
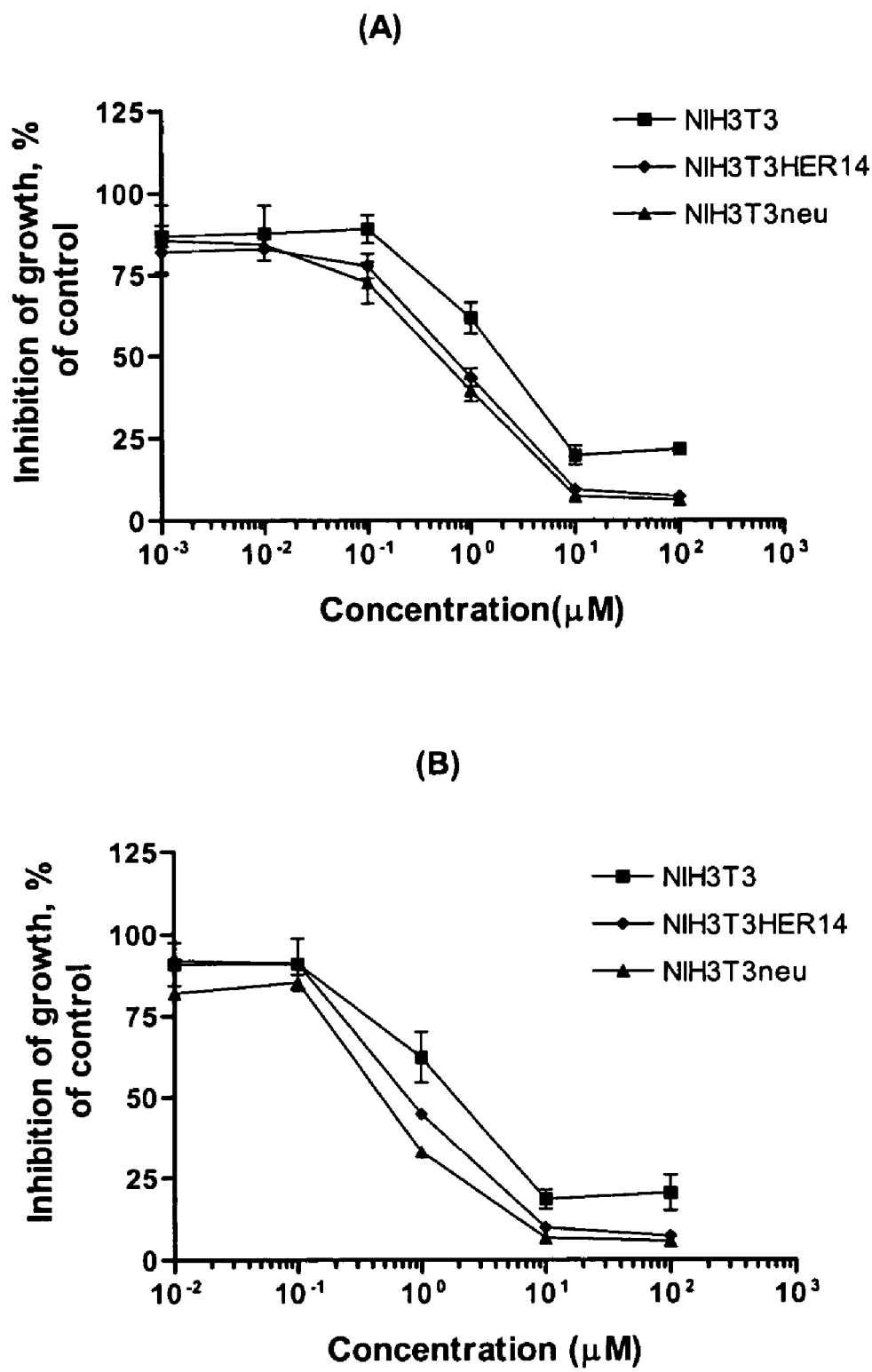
FIG. 21 shows the antiproliferative effect of ZR2003 (A) and ZR2002 (B) in NIH3T3, NIH3T3HER14 and NIH3T3neu. Cells were exposed to each drug for 120 h. Cell growth was measured using SRB assay. Each point represents at least two independent experiments.

Selective growth factor stimulation assay: In order to keep the comparison within one cell line responsive to many different growth factors, NIH3T3HER14 cells was selected (NIH3T3 cells stably transfected with the EGFR gene). SRB assays demonstrated that ZR2002 was capable of selectively blocking EGF or TGFα-induced proliferation in NIH3T3HER14 cells. A maximum 100% inhibition of EGF-stimulated growth was achieved at concentrations as low at 0.1 µM. ZR2002 was 10-fold less effective in inhibiting PDGF-stimulated growth (100% inhibition at 1 µM) and exhibited a lesser effect on serum-stimulated growth in NIH3T3HER14 cells (100% growth inhibition at concentrations >10 µM) (FIG. 5), indicating preferential blockade of EGFR mediated proliferation. Moreover, the selective potency of ZR2002 and ZR2003 was evaluated in a panel of isogenic cell lines NIH3T3, NIH3T3HER14 (transfected with EGFR gene) and NIH3T3neu (transfected with ErbB2 gene). Interestingly, ZR2003 as well as ZR2002 selectively blocked the growth of the transfectants (FIG. 21A, B).

(b) Reversibility of Growth Inhibitory Activity.

Figure 6:
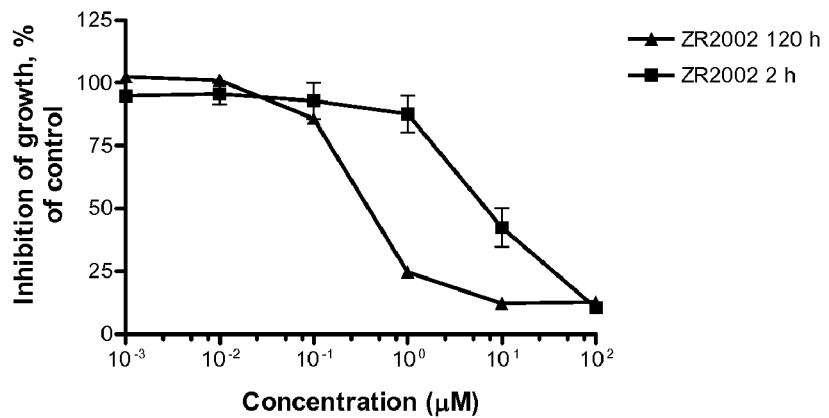
FIG. 6 shows the reversibility of the antiproliferative effect of ZR2002 (A), PD168393 (B) and ZR01 (C) in MDA-MB-468 cells. Cells were exposed to each drug for 2 h, after which they were allowed to recover for 120 h in drug free medium, or continuously for 120 h. Cell growth was measured using SRB assay. ZR2002 2 h ($IC_{50}$=5.164 μM), ZR2002 120 h ($IC_{50}$=0.2345 μM). PD168393 2 h ($IC_{50}$=6.517 μM), PD168393 120 h ($IC_{50}$=0.6285 μM). ZR01 2 h ($IC_{50}$>100 μM), ZR01 120 h ($IC_{50}$=45.74 μM). Each point represents at least two independent experiments.
Figure 6:
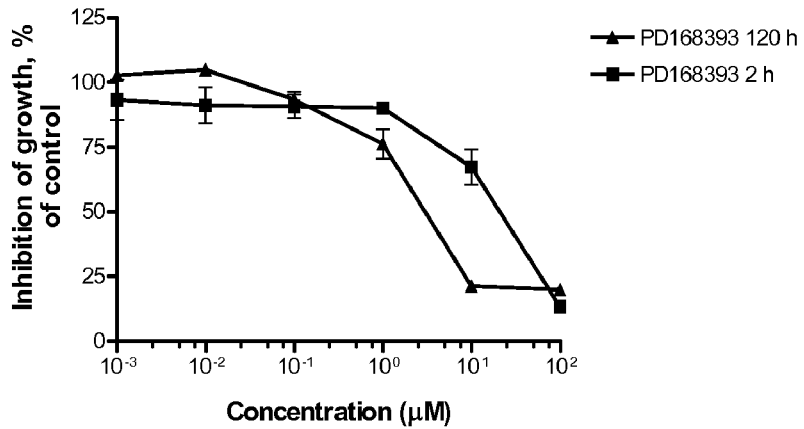
Figure 6:
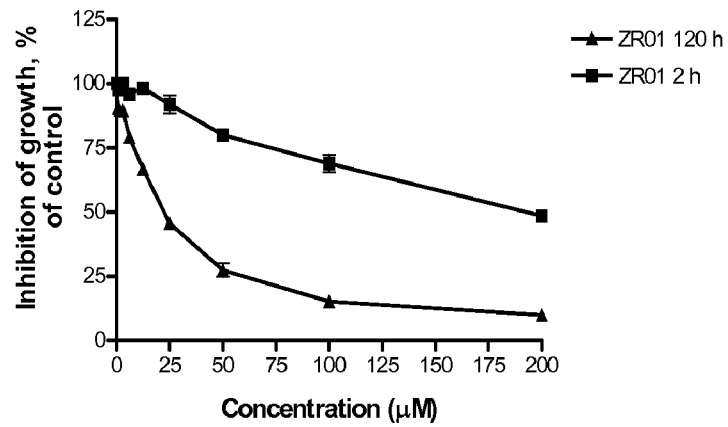
Figure 7:
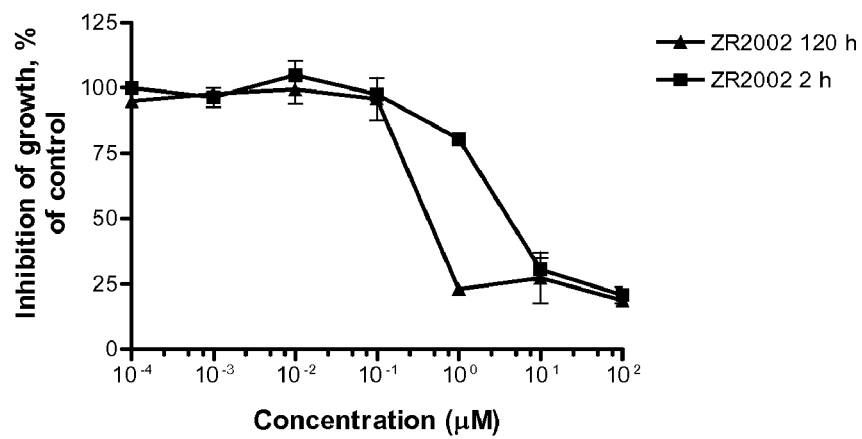
FIG. 7 shows the reversibility of antiproliferative effect of ZR2002 (A), PD168393 (B) and ZR01 (C) in MDA-MB-453. Cells were exposed to each drug for 2 h, after which they were allowed to recover for 120 h in drug free medium, or continuously for 120 h. Cell growth was measured using SRB assay. ZR2002 2 h ($IC_{50}$=4.171 μM), ZR2002 120 h ($IC_{50}$=0.426 μM). PD168393 2 h ($IC_{50}$=11.50 μM), PD168393 120 h ($IC_{50}$=1.708 μM). Each point represents at least two independent experiments.
Figure 7:
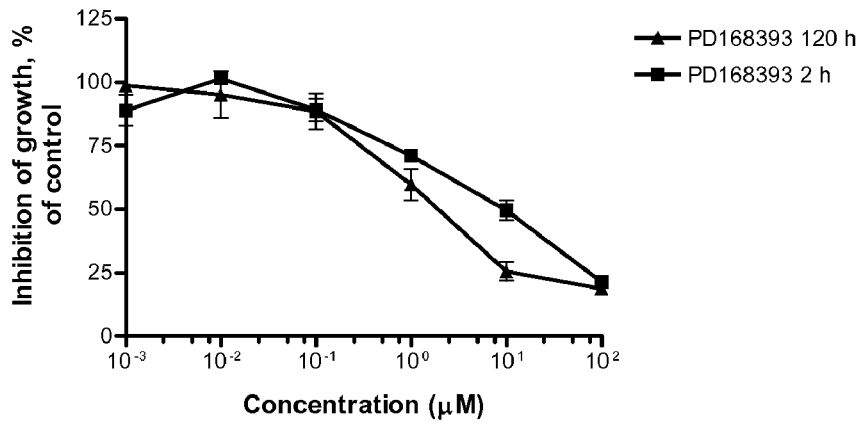
Figure 7:
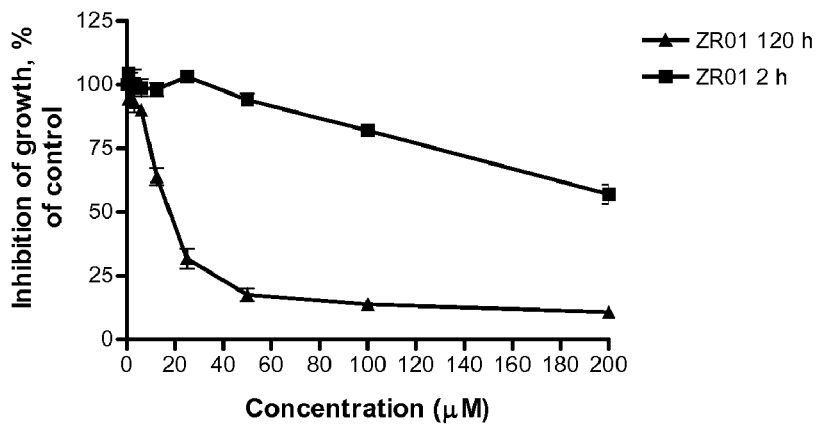

Reversal of growth inhibitory activity: Following 120 h of continuous exposure, the results obtained from SRB assay as illustrated by FIG. 6A, showed that ZR2002 (IC$_{50}$=0.36 µM) was 7.3-fold more potent than PD168393 (IC$_{50}$=2.62 µM, FIG. 6B) and 58-fold more potent than the reversible inhibitor ZR01 (IC$_{50}$=20.87 µM, FIG. 6C), in the EGFR-overexpressing MDA-MB-468 breast cancer cells. More importantly, in a short exposure assay (2 h) followed by 120 h recovery, an almost complete loss of activity was observed for ZR01 in the MDA-MB-468 cell line (IC$_{50}$=174.8 µM, FIG. 6C) indicating that it induced significantly reversible growth inhibitory activity. In contrast, ZR2002 and PD168393 showed significant retention of their activities. However, after the 120 h recovery, ZR2002 was 2,6-fold more potent than PD168393 (IC$_{50}$=7.4 and 19.10 µM, respectively FIGS. 6A, B) indicating a more sustained effect than that induced by PD168393. The same results were obtained in the erbB2 overexpressing breast carcinoma cell line MDA-MB-453. Indeed, following 120 h continuous exposure ZR2002 (IC$_{50}$=0.43 µM, FIG. 7A) showed a 4.2-fold greater inhibitory activity than PD168393 (IC$_{50}$=1.81 µM, FIG. 7B) and a 37-fold greater inhibitory activity than ZR01 (IC$_{50}$=16 µM, FIG. 7C) in this cell line. In a short exposure assay (2 h, followed by 120 h recovery), ZR01 completely lost its activity (IC$_{50}$=212 µM, FIG. 7C) whereas ZR2002 and PD168393 retained a significant antiproliferative effect in MDA-MB-453 cells. Again, as in MDA-MB-468, Zr2002 induced a 2.5-fold greater potency than PD168393 (IC$_{50}$=4.17 µM and 10.32 respectively, FIGS. 7A, B).

Figure 19:
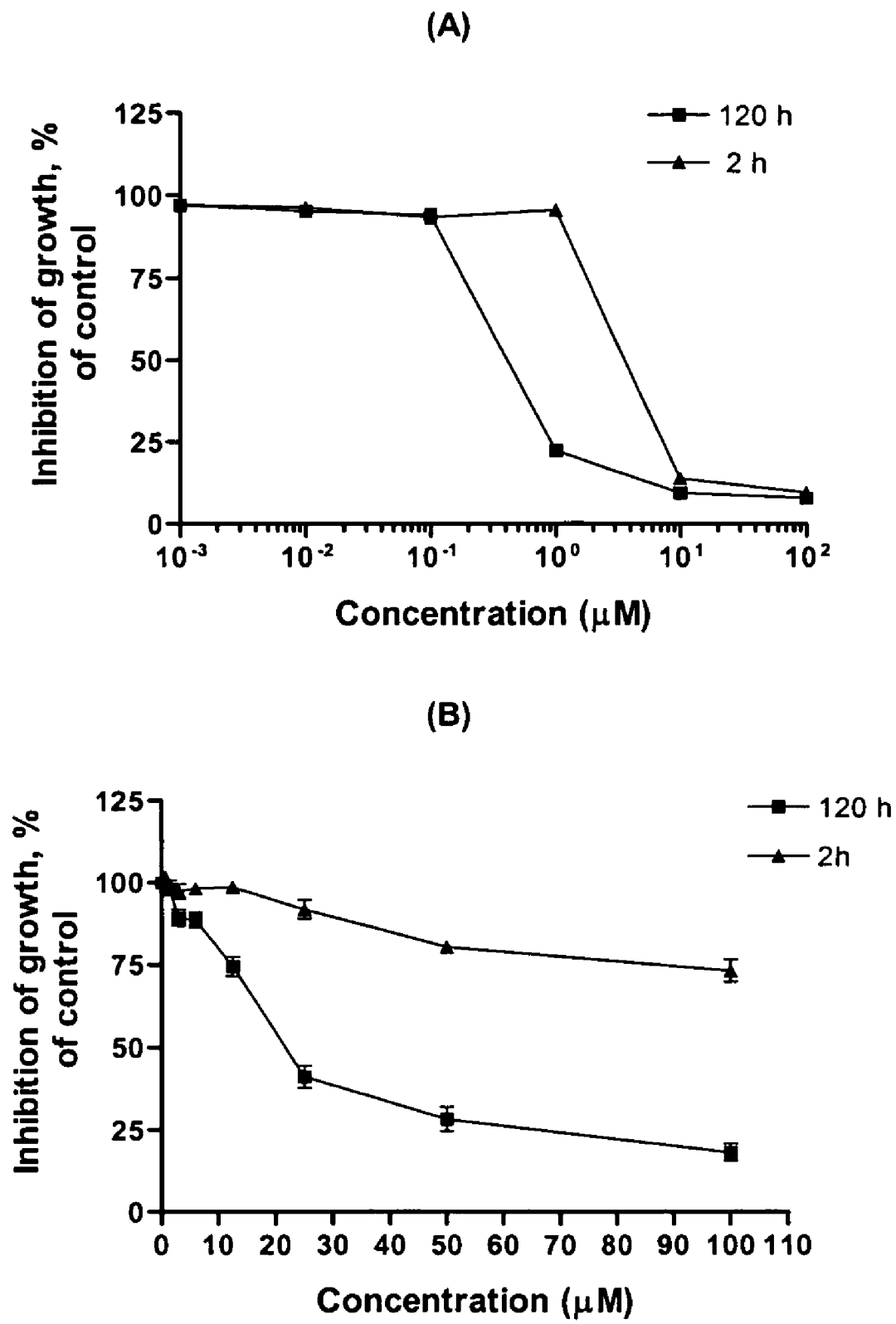
FIG. 19 shows the reversibility of antiproliferative effect of ZR2003 (A) and FD105 (B) in MDA-MB-468. Cells were exposed to each drug for 2 h, after which they were allowed to recover for 120 h in drug free medium, or continuously for 120 h. Cell growth was measured using SRB assay. Each point represents at least two independent experiments.
Figure 20:
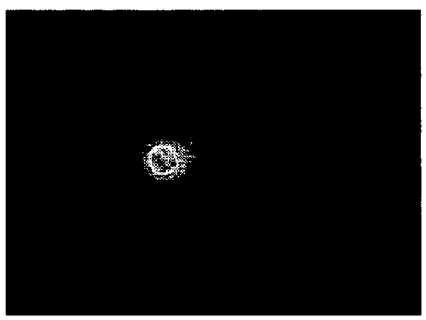
FIG. 20 shows a picture of a comet assay for untreated MDA-MB-468 cells (A) and cells treated with 10 mM ZR2002 for 2 h (B). Comets were visualized examined under fluorescence microscopy at 330× magnification.
Figure 20:
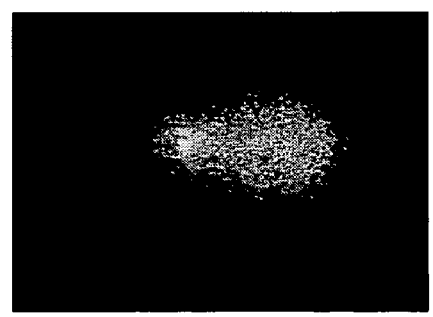

Under 120 h continuous exposure, the results obtained from the SRB assay, as illustrated by FIG. 19A, showed that ZR2003 (IC$_{50}$=0.51 µM) was 46-fold more potent than the reversible inhibitor FD105 (IC$_{50}$=23.59 µM, FIG. 19B) in MDA-MB-468 cells. Importantly, in a short exposure assay (2 h) followed by 120 h recovery, an almost complete loss of activity was observed for FD105 in these cells (IC$_{50}$=191.9 µM, FIG. 19B) indicating that it induced significantly reversible growth inhibitory activity. However after the 120 h recovery, ZR2003 significantly retained its effect (IC$_{50}$=4.81 µM, FIG. 19A) indicating a more sustained growth inhibitory effect of the latter. These results were similar to those of ZR2002 indicating that the chloroethyl group plays a significant role in the activity of the molecule by alkylating the DNA as demonstrated by the comet assay (FIG. 20).

Example 15

Effects on Signal Transduction

Figure 8:
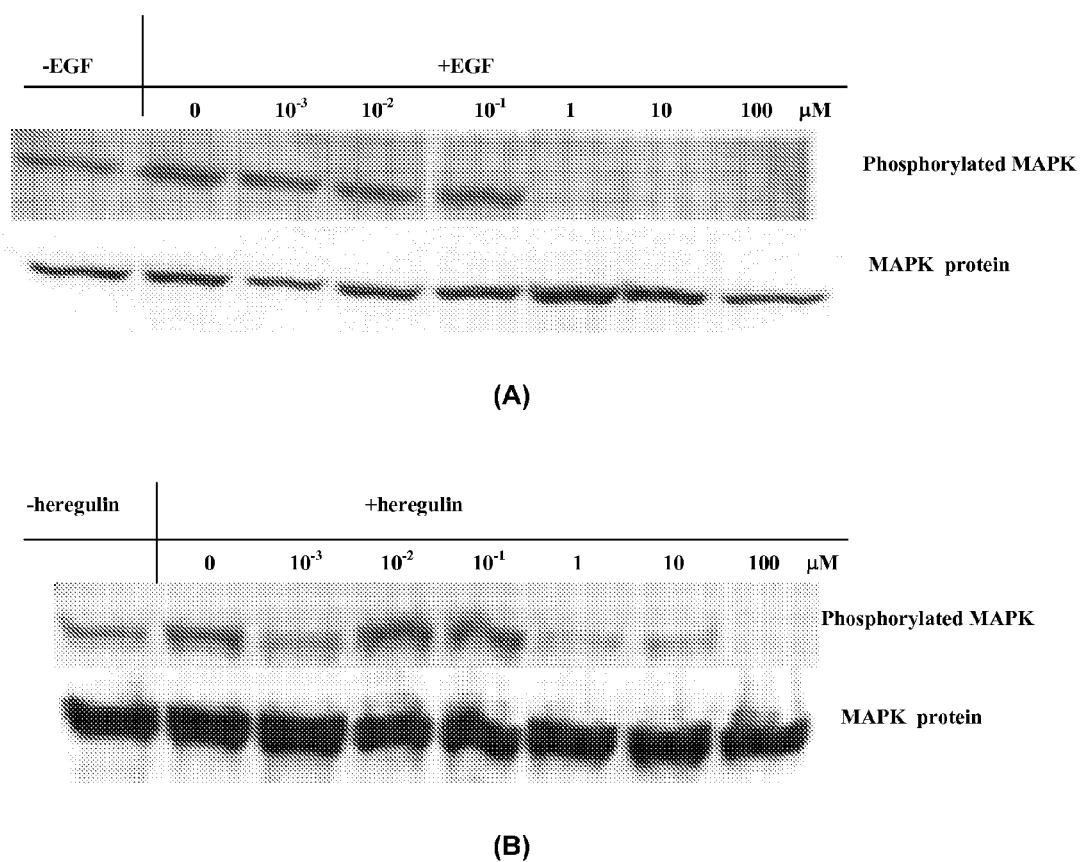
FIG. 8 shows the effects of ZR2002 on MAPK (Erk1, 2) activation in MDA-MB-468 (A) and MDA-MB-453 cells (B). Serum starved cells were preincubated for 2 h with the indicated concentrations of ZR2002 prior to stimulation with EGF or heregulin. Protein lysates were obtained and Western blot was performed as described (23).

The ability of ZR2002 to inhibit the phosphorylation of the key signal transduction mediator MAPK (Erk, 2) was investigated. The results showed that ZR2002 induced 100% inhibition of EGF-stimulated phosphorylation of MAPK at concentrations as low as 1 µM in MDA-MB-468 cells. Similarly, it blocked heregulin-stimulated MAPK phosphorylation in MDA-MB-453 cells (FIGS. 8A, B) suggesting that ZR2002 targets both EGFR and the erbB2 gene product and this may be associated with significant inhibition of downstream signaling.

Example 16

Quantization of DNA Damage

Figure 9:
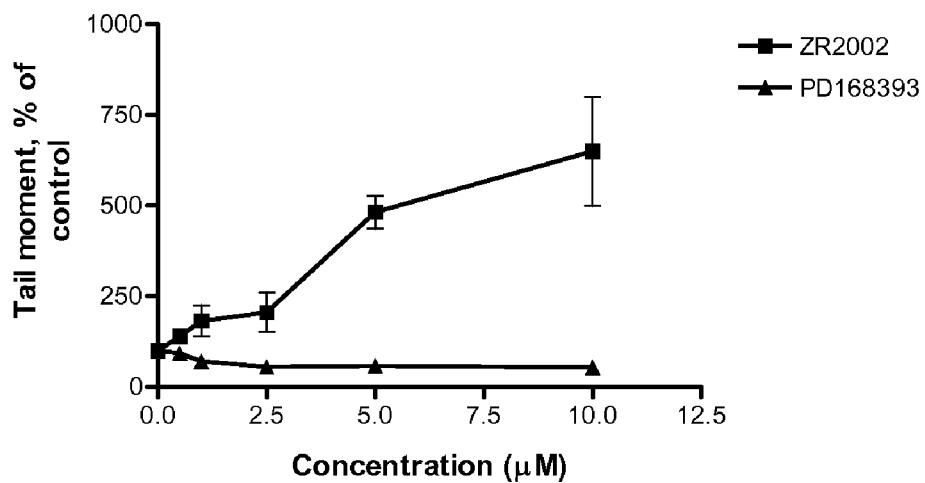
FIG. 9 shows the quantification of DNA damage using the alkaline comet assay. The tail moment was used as a parameter for the detection of DNA damage in MDA-MB-468 cells exposed to ZR2002 (A), PD168393 (A) and ZR01 (B) for 2 h. Each point represents at least two independent experiments.
Figure 9:
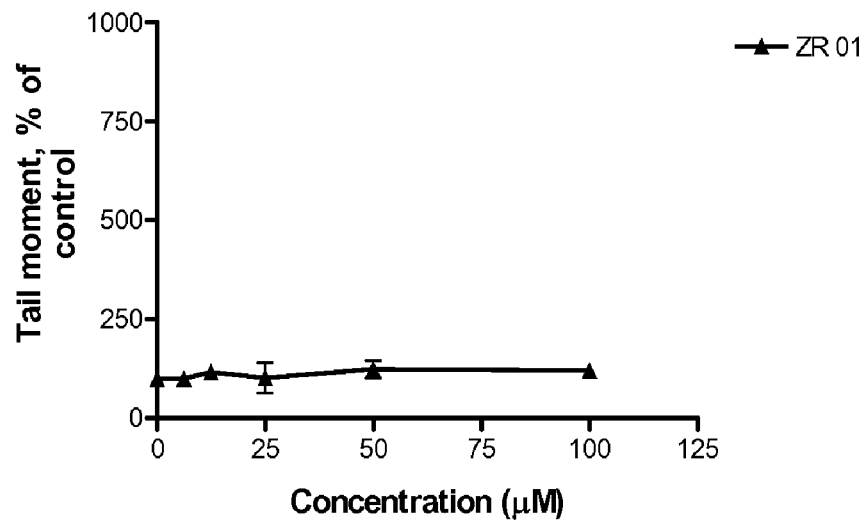

Using the alkylating comet assay, it was demonstrated that in contrast to ZR01 and PD168393, ZR2002 damages DNA in a dose dependent manner, after a 2 h drug exposure (FIGS. 9A, B). It induced significant DNA damage at concentrations of as low as 10 µM, whereas known cytotoxic agents such as temozolomide (20) or BCNU (21) induce the same levels of DNA damage at much higher concentrations (>50 µM) in this assay.

Example 17

Annexin V Binding

Figure 10:
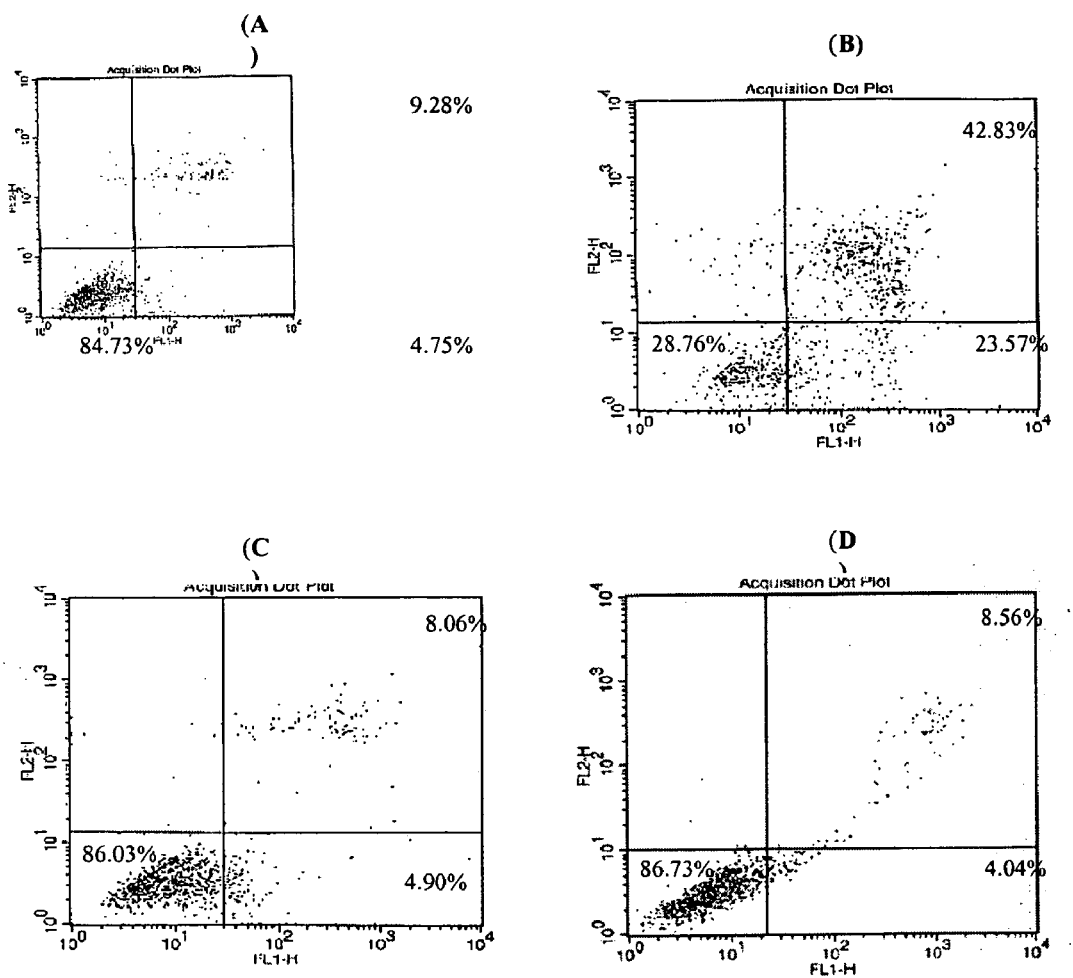
FIG. 10 shows the Annexin V binding analysis following drug treatment in the MDA-MB-468 cell line. Cells were untreated (A), or treated with 5 mM ZR2002 (B), 5 mM ZR01 (C) or with 5 mM PD168393 (D) for 48 h drug exposure. Cells were harvested and incubated with annexin V-FITC and PI. Annexin V-FITC and PI binding were quantified by flow cytometry. Dot plots show annexin V-FITC binding on the X axis (FL1-H) and PI staining on the Y axis (FL2-H). Dots represent cells as follow: lower left quadrant, normal cells (FITC−/PI−); lower right quadrant, early apoptotic cells (FITC+/PI−); upper right quadrant, dead cells by apoptosis (FITC+/PI+); upper left quadrant, necrotic cells (FITC−/PI+).
Figure 11:
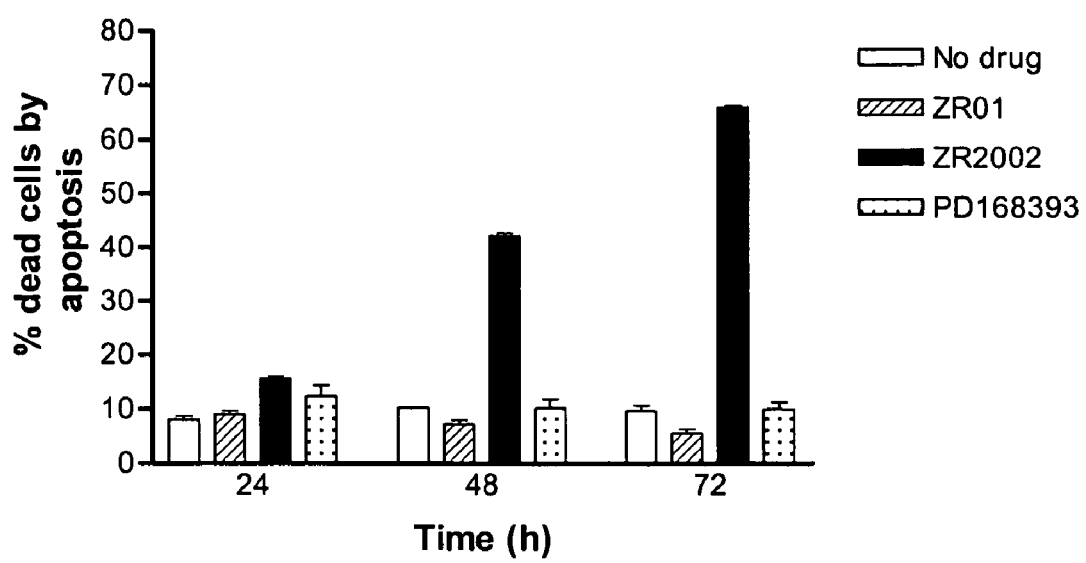
FIG. 11 shows the induction of cell death by apoptosis in the MDA-MB-468 cell line following drug treatment. Cells were untreated or treated with 5 mM ZR2002 or 5 mM ZR01 or 5 mM PD168393 for 24, 48 and 72 h. Each point represents at least two independent experiments.
Figure 22:
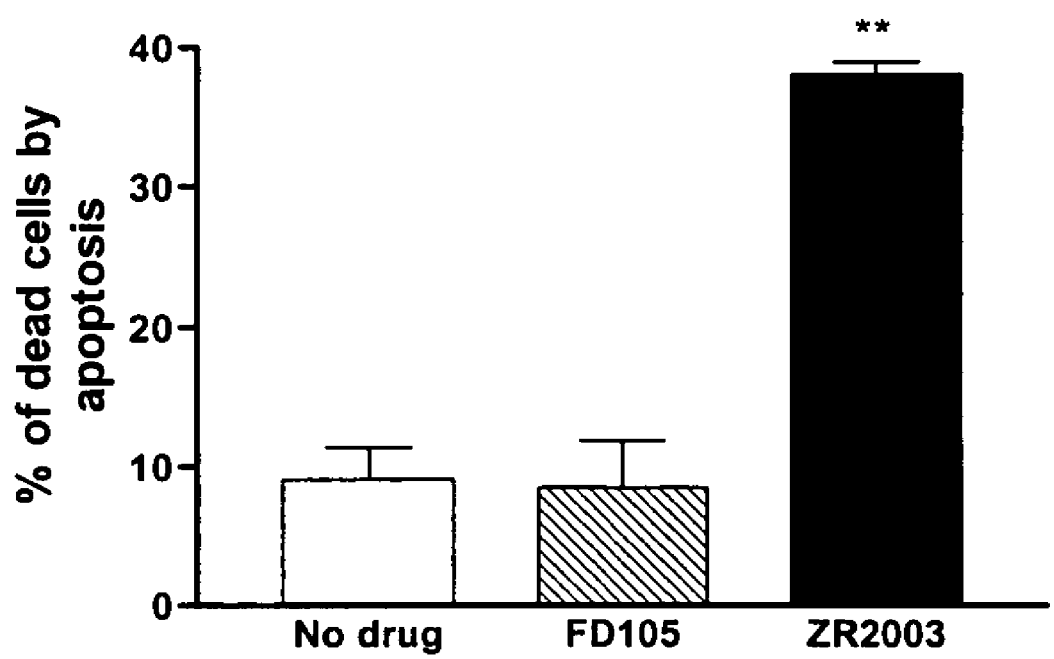
FIG. 22 shows the induction of cell death by apoptosis in the MDA-MB-468 cell line following drug treatment. Cells were untreated or treated with 12 μM ZR2003 or 12 μM FD105 for 48 h. Each point represents at least two independent experiments. Results are shown as mean±SE. Statistical analysis was carried using Student's t test with two tailed, **p<0.01 ZR2003 vs FD105.

Annexin V-FITC (FL1-H) and PI (FL2-H) staining (detected by flow cytometry) was used to distinguish viable (PI−/FITC−), early apoptotic (PI−/FITC+), dead cells by apoptosis (PI+/FITC+) and necrotic (PI+/FITC−) cells (25). Apoptosis was studied at 5 µM, a concentration at which ZR2002 started showing detectable levels of apoptosis in MDA-MB-468 (FIG. 10). Cell death by apoptosis in cells exposed to ZR2002 increased with increasing exposure time. In contrast, barely detectable levels of apoptosis were observed in cells exposed to ZR01 or PD168393 (FIG. 11), indicating that the chloroethyl group has conferred significant cytotoxic properties to ZR2002. Apoptosis was studied at 12 µM, a concentration at which ZR2003 started showing detectable levels of apoptosis (p<0.01) in MDA-MB-468 when compared to its free counterpart FD105 (FIG. 22). This again is indicative that the chloroethyl group has conferred significant cytotoxic properties to ZR2003.

Example 18

Diagnostic Potential

Flow cytometric analysis of ZR2002 in isogenic cells demonstrated that fluorescence intensities were higher in cells overexpressing EGFR. When analyzed in a panel of established cell lines, it was found that the intensities associated with ZR2002 linearly increased with increasing levels of EGFR with a Pearson coefficient of 0.7, p<0.02. This is a highly significant observation since, due to unavailability of a shorter UV laser wavelength, the analysis was performed in the 360 nm range, a wavelength significantly higher than its approximately 290 nm maximum excitation peak. The significantly linear correlation, suggests that ZR2002 is prototypical of a generation of molecules that can be used to stain EGFR in biopsy specimens in lieu of immunodetection which requires expensive antibodies.

Example 19

Decomposition and Alkylating Properties of Double-Arm Combi-Triazenes 5-9

(a) Hydrolysis

The degradation of double-arm combi-triazenes 5-9 has been investigated by HPLC. After 24 h incubation in serum at 37° C., compounds 5 (aromatic spacer) and 9 (aliphatic spacer), showed completely different degradation patterns, the former releasing only negligible quantities of expected parent amine 1, when the latter released 50% of amine 1 (the release of 2 eq. of amine was taken for 100%). The rates of decomposition of bis-triazenes 7, 8 and 9 were measured by fluorescence spectroscopy by monitoring the formation of 1 (excitation: 279 and emission: 451). The determined half-lives ranged from 2 h for 7 and 8 to 3 h 20 min for 9.

(b) Alkylation

The alkylating properties of double-arm combi-triazenes 5-9 were investigated using the NBP assay at 37° C. in Tris buffer at pH 7.5. NBP was dissolved in ethylene glycol and the bis-triazenes in DMSO. The NBP alkylation products were studied by mass spectrometry at the 4 h and 22 h time points. No alkylated product was observed for the double-arm combi-triazenes 5 and 6. In contrast, following a 4 h incubation period, double-arm combi-triazenes 7-9 showed undegraded bis-triazenes in addition to corresponding monoalkylated NBP adducts A with an intact second quinazolinotriazene moiety (Scheme 20). This is indicative of the possibility of a step-wise decomposition, as opposed to a simultaneous decomposition, of the two triazene chains when in the presence of nucleophiles.

Scheme 20

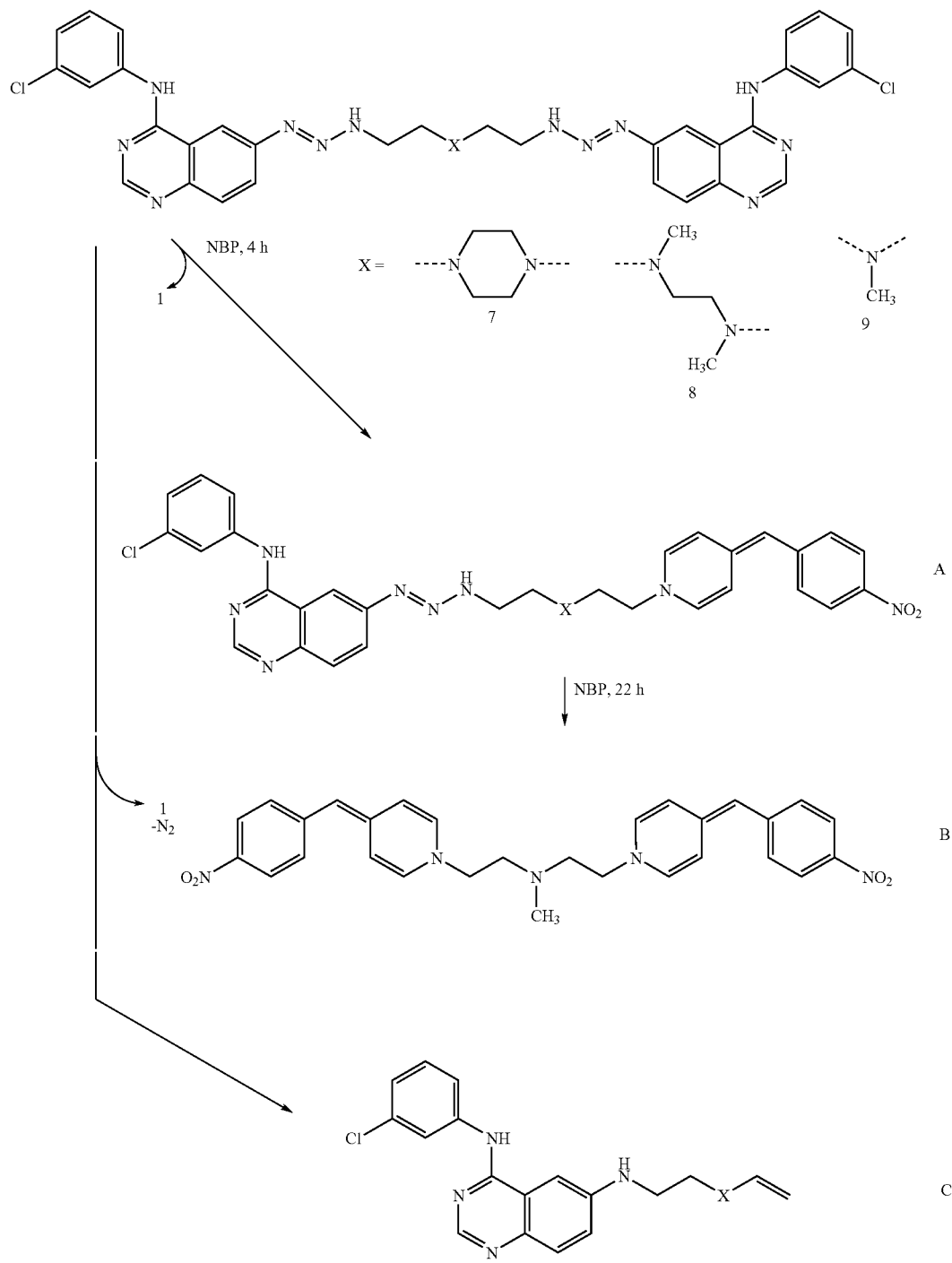

In solution, these double-arm combi-triazenes (7-9) may adopt a conformation in which one triazene is stabilized via interaction with the 2-alkylamine nitrogen, while the other triazene, in a rather non-conjugated form, undergoes rapid cleavage under aqueous conditions. The possible stabilization of one triazene function by an intramolecular hydrogen bond is illustrated below in Scheme 21 with double-arm combi-triazene 9.

Scheme 21

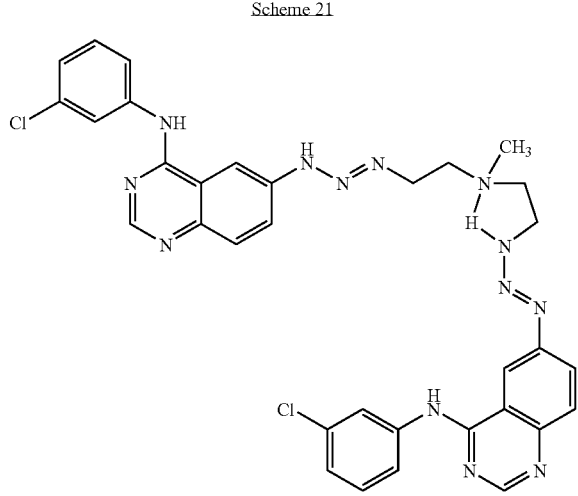

Following an incubation period of 22 h, no starting bis-triazene could be detected; all samples showing a signal corresponding to the mass of a monoalkylated adduct of type A as well as a mass signal in correlation with the loss of one molecule of amine 1 and double $N_2$ elimination (structure C). Double-arm combi-triazene 9, containing a nitrogen mustard spacer, showed a bis-alkylated NBP (B, Scheme 20), reminiscent of DNA cross-link adducts.

Example 20

Biological Activity of Double-Arm Combi-Triazenes 5-9

(a) Purified Enzyme Assay

Figure 13:
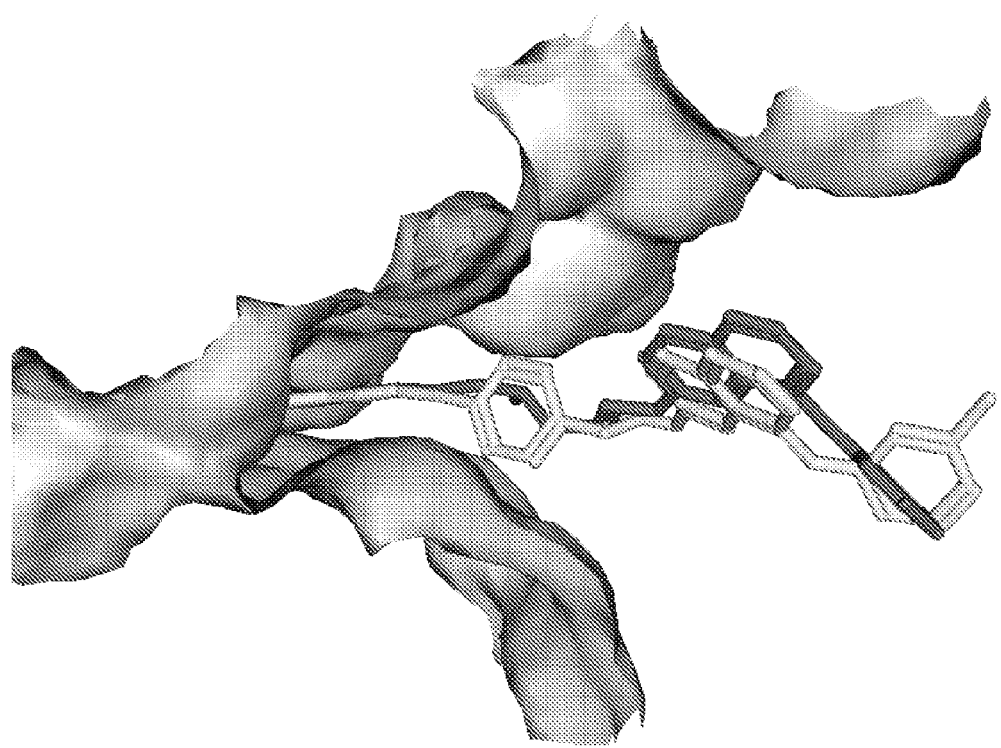
FIG. 13 shows an in silico docking study of double-arm combi-triazenes 6 (in yellow) and 9 (in blue) docked into the EGFR TK ATP binding site.

The EGFR inhibitory potency of the different double-arm combi-triazenes (5-9) was evaluated in a purified enzyme assay. The observed activities were as follows: $IC_{50}$=7 μM (5), $IC_{50}$>10 μM (6), $IC_{50}$=1 μM (7), $IC_{50}$=0.05 μM (8), and $IC_{50}$=0.003 μM (9). The potency of the double-arm combi-triazenes varied with the type of spacer separating the two quinazoline moieties. Spacers containing an aromatic or an aliphatic ring were deleterious to activity. This can be rationalized by an in silico docking study as illustrated in FIG. 13. As can be observed, the aromatic ring of the p-diaminoxylene spacer of 6 clashes with the narrow opening of the EGFR TK ATP binding site. On the other hand, the flexible spacer N,N-bis(2-aminoethyl)methylamine of 9 snakes out of the binding pocket and positions the second anilinoquinazoline moiety in the space open to the solvent such that it could possibly bind to hydrophobic patches near the major binding pocket. Given that the $IC_{50}$ values were determined after a 10 min exposure, they reflect the binding of EGFR TK inhibitory activity of the intact molecules.

(b) Selectivity for Her14 and Neu Transfected NIH3T3 Cell Lines

Figure 14:
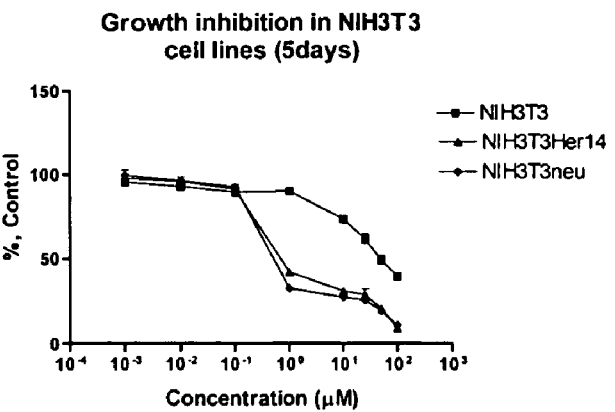
FIG. 14 shows the selective growth inhibition of double-arm combi-triazenes 7-9 on NIH3T3/neu and NIH3T3/Her14 cell lines.
Figure 14:
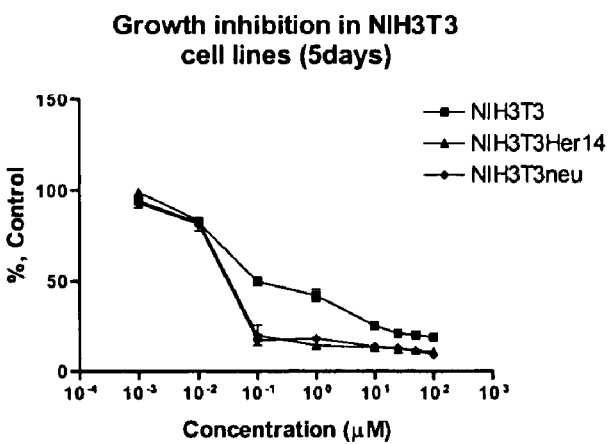
Figure 14:
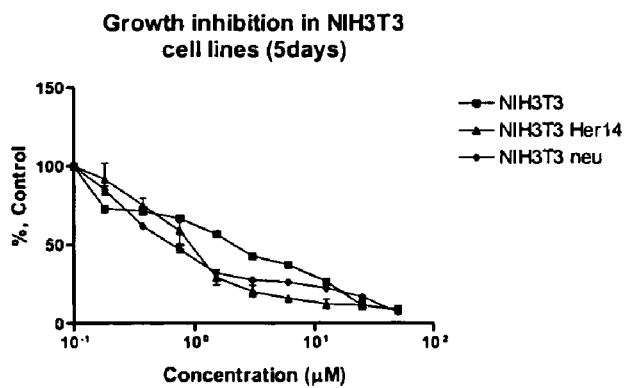

The growth inhibitory potency of double-arm combi-triazenes 7-9 was tested in a panel of isogenic NIH3T3 cells, two of which transfected with the EGFR or the neu oncogene (FIG. 14). Double-arm combi-triazene 7 was the most selective with a 110-fold selectivity for a neu transfectant ($IC_{50}$ (NIH3T3/neu)=0.4 mM; $IC_{50}$ (NIH3T3)=44 mM)) and a 88-fold selectivity for a EGFR transfectant ($IC_{50}$ (NIH3T3/Her14)=0.5 mM). Double-arm combi-triazene 9 was the least selective showing a 4 fold selectivity for EGFR ($IC_{50}$ (NIH3T3/Her14)=0.5 mM, $IC_{50}$ (NIH3T3)=2.3 mM) and a 7-fold selectivity for neu ($IC_{50}$ (NIH3T3/Her14)=0.3 mM). Double-arm combi-triazene 8 showed comparable selectivity, but was 20-fold more active ($IC_{50}$ (NIH3T3)=0.1 mM, $IC_{50}$ (NIH3T3/Her14)=0.02 mM. $IC_{50}$ (NIH3T3/neu)=0.02 mM).

(c) Screening on a Prostate Cancer Cell Line Panel

Figure 15:
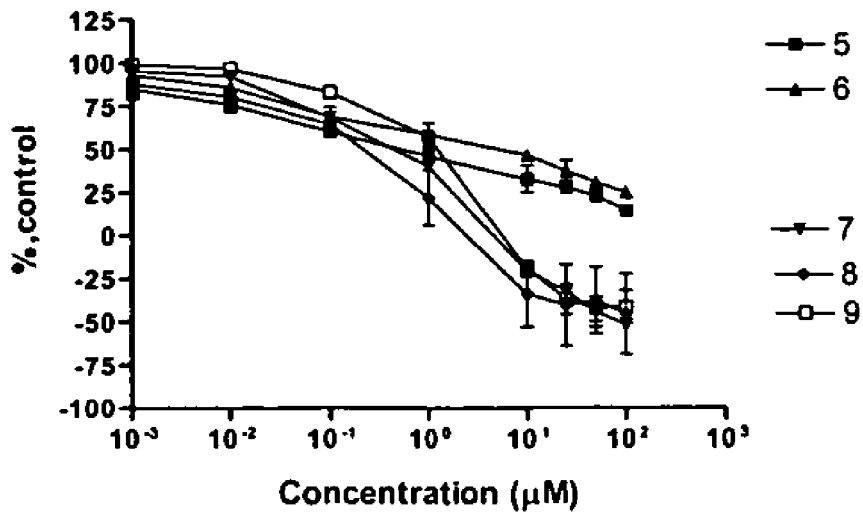
FIG. 15 shows the growth inhibition of double-arm combi-triazenes 5-9 in androgen independent cancer cell line DU145.
Figure 15:
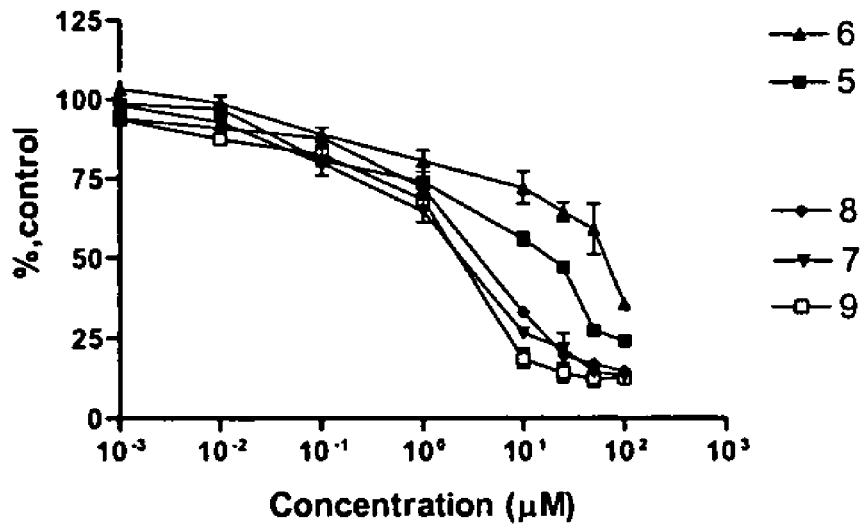
Figure 16:
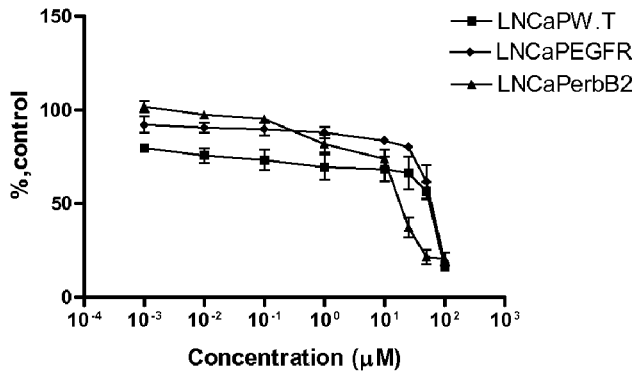
FIG. 16 shows the growth inhibition of double-arm combi-triazenes 5-9 in a panel of androgen sensitive LNCaP cell lines; wild type, EGFR transfected and erbB2 transfected (FIG. 16).
Figure 16:
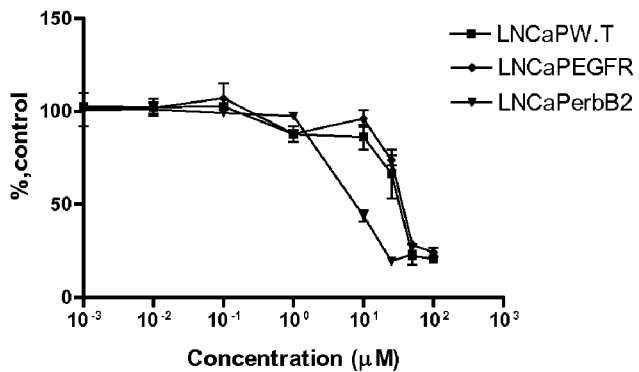
Figure 16:
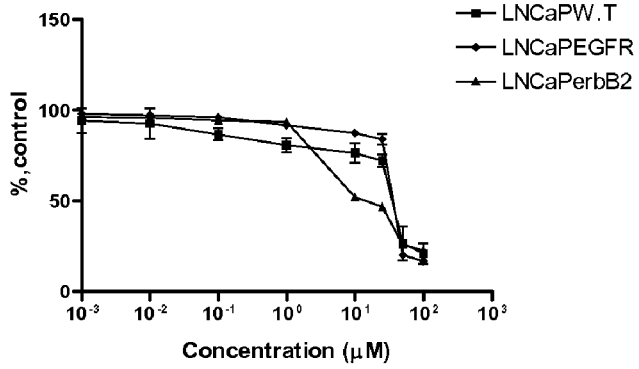
Figure 16:
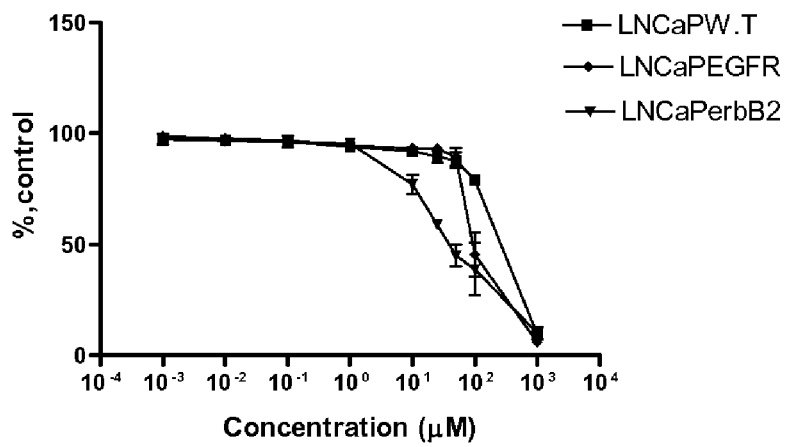
Figure 16:
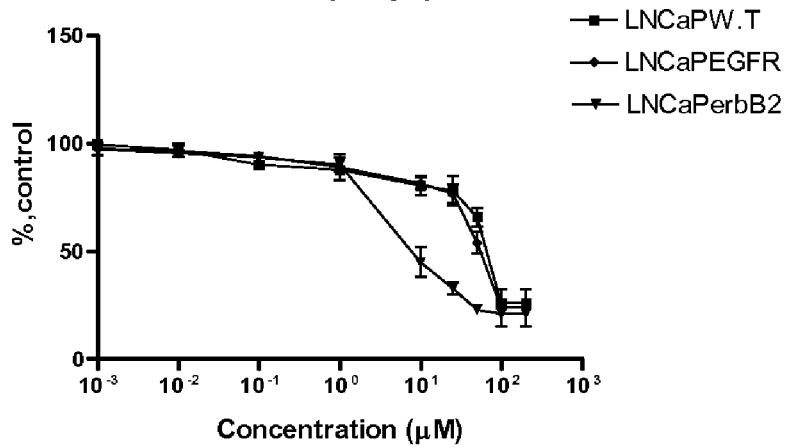

The growth inhibitory potency of double-arm combi-triazenes 5-9 was tested in an androgen independent prostate cancer cell line DU145 (FIG. 15) and in a panel of androgen sensitive LNCaP cell lines: wild type, EGFR transfected and erbB2 transfected (FIG. 16). As shown in the FIG. 15, double-arm combi-triazenes 5 and 6 do not show any significant potency. In contrast, double-arm combi-triazenes 7, 8 and 9 showed significant potency with an $IC_{50}$ of 2.8 μM, 1.0 μM and 2.6 μM, respectfully. The same trend was observed following a 6 day continued growth inhibition assay ($IC_{50}$=12 μM (5), $IC_{50}$=35 μM (6), $IC_{50}$=1.8 μM (7), $IC_{50}$=3.2 μM (8), $IC_{50}$=2.3 μM (9)). As can be observed from FIG. 16, following a 6 day growth inhibition assay, all tested double-arm combi-triazenes showed a clear selectivity for the LNCaPerbB2 transfected cell line assay ($IC_{50}$=18 μM (5), $IC_{50}$=37 μM (6), $IC_{50}$=9 μM (7), $IC_{50}$=6 μM (8), $IC_{50}$=11 μM (9)), but low or none for LNCaPEGFR.

Example 21

In Vivo Activity of ZR2002 and ZR2003

Figure 23:
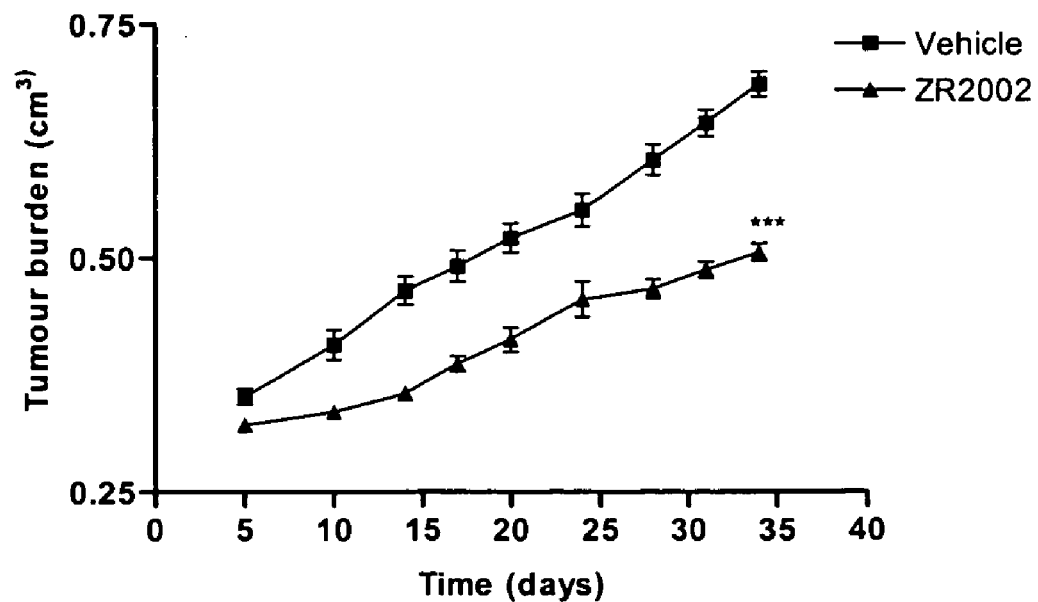
FIG. 23 shows the in vivo efficacy of ZR2002 against human breast MDA-MB-468 in SCID mice. The mice were implanted s.c. and the drug given i.p. in a solution of aqueous cremaphore (25%)/ethanol (25%) (0.2 ml). The drugs at a dose of 50 mg/kg were given every 3-4 days over a period spanning at least one month. Results are shown as mean±SE tumor volume. Statistical analysis was carried using Student's t test with two tailed, ***p<0.001 ZR2002 vs. vehicle.
Figure 24:
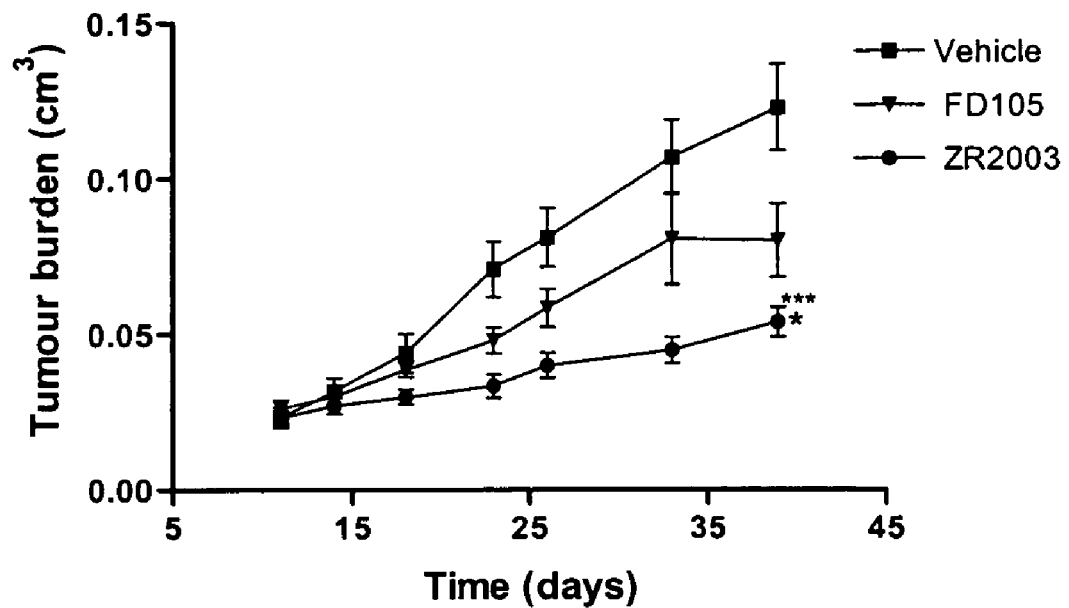
FIG. 24 shows the in vivo efficacy of ZR2003 and FD105 against human breast MDA-MB-468 in SCID mice. The mice were implanted in mammary fat pad and the drug given i.p. in a solution of aqueous cremaphore (12.5%)/ethanol (12.5%) (0.4 ml). The drugs at a dose of 50 mg/kg was given every 3-4 days over a period spanning at least one month. Results are shown as mean±SE tumor volume Statistical analysis was carried using Student's t test, ***p<0.001 ZR2003 vs. vehicle; *p<0.05 ZR2003 vs. FD105.

Having demonstrated the dual EGFR/DNA targeting properties of ZR2002 in vitro, its efficacy against the high EGFR expressing MDA-MB-468 breast cancer cells implanted s.c in SCID mice was tested. The results showed that although, the in vivo antitumor activity of ZR2002 at its tolerated dose 50 mg/kg was significant (p<0.001), it remained that this combi-molecule exerted a moderate antiproliferative activity in this model which was believed to be due to the poor bioavailability of the 3'-bromo-containing ZR2002 (FIG. 23). However, its 3'-chloro analogue ZR2003 at the same dose exerted a strong antiproliferative activity against MDA-MB-468 breast cancer cells implanted in the mammary fat pad in SCID mice. Also, It showed significant superior potency (p<0.05) when compared with its free counterpart FD105 (FIG. 24), suggesting that the addition of the chloroethyl group to the quinazoline backbone confers significant antiproliferative advantage.

Although the present invention has been described hereinabove by way of preferred embodiments thereof, it can be modified without departing from the spirit and nature of the subject invention as defined in the appended claims.

REFERENCES

1. Neal D E, March C, Bennett M K, Abel P D, Hall R R, Sainbury J R, Harris A L; Epidermal-growth-factor receptors in human bladder cancer: comparison of invasive and superficial tumours. *Lancet* 1985; 1: 366-368.
2. Gross M E, Zorbas M A, Danels Y J, Garcia R, Gallick G E, Olive M, Brattain M G, Boman B M, Yeoman L C; Cellular growth response to epidermal growth factor in colon carcinoma cells with an amplified epidermal growth factor receptor derived from a familial adenomatous polyposis patient. *Cancer Res.* 1991; 51: 1452-1459.

3. Damstrup L, Rygaard K, Spang-Thomsen M, Poulsen H S; Expression of the epidermal growth factor receptor in human small cell lung cancer cell lines. *Cancer Res.* 1992; 52: 3089-3093.
4. Koenders P G, Beex L V, Guerts-Moespat A. Heuvel J J. Kienhuis C B, Benraad T J; Epidermal growth factor receptor-negative tumors are predominantly confined to the subgroup of estradiol receptor-positive human primary breast cancers. *Cancer Res.* 1991; 51: 4544-4548.
5. Slamon D J, Godolphin W, Jones L A, Holt J A, Wong S G, Keith D E, Levin W J, Stuart S G, Udove J, Ullrich A, Press M F; Studies of the HER-2/neu proto-oncogene in human breast and ovarian cancer. *Science* 1989; 244: 707-712.
6. Carraway K L, Cantely L C (1994); A neu acquaintance for erbB3 and erbB4: a role for receptor heterodimerization in growth signalling. *Cell,* 1994; 78: 5-8.
7. Stebbing J, Copson E, O'Reilly S; Herceptin (trastuzamab) in advanced breast cancer. *Cancer Treat Rev.* 2000; 26: 287-290.
8. Ciardiello F, Caputo R, Bianco R, Damiano V, Pomatico G, De Placido S, Bianco A R, Tortora G; Antitumor effect and potentiation of cytotoxic drugs activity in human cancer cells by ZD-1839 (Iressa), an epidermal growth factor receptor-sensitive tyrosine kinase inhibitor. *Clin. Cancer Res.* 2000; 6: 2053-2063.
9. Rewcastle G W, Denny W A, Bridges A J, Zhou H, Cody D R, McMichael A, Fry D W; Tyrosine kinase inhibitors: Synthesis and structure-activity relationships for 4-[(phenylmethyl)amino]- and 4-(phenylamino)quinazolines as potent adenosine 5'-triphosphate binding site inhibitors of the tyrosine kinase domain of the epidermal growth factor receptor. *J Med Chem.* 1995; 38: 3482-3487.
10. Rewcastle G W, Bridges A J, Fry D W, Rubin J R, Denny W A; Tyrosine kinase inhibitors: Synthesis and structure-activity relationships for 6-substituted 4-(phenylamino) pyrimido[5,4-d]pyrimidines designed as inhibitors of the epidermal growth factor receptor. *J Med Chem.* 1997; 40: 1820-1826.
11. Rewcastle G W, Murray D K, Elliot W L, Fry D W, Howard C T, Nelson J. M, Roberts B J, Vincent P W, Showalter H D, Winters T R, Denny W A; Tyrosine kinase inhibitors: Structure-activity relationships for methylamino-substituted derivatives of 4-[(3-bromophenyl) amino]-6-(methylamino)-pyrido[3,4-d]pyrimidine (PD 158780), a potent and specific inhibitor of the tyrosine kinase activity of receptors for the EGF family of growth factors. *J Med Chem.* 1998; 41: 742-751.
12. Fry D W; Inhibition of the epidermal growth factor receptor family of tyrosine kinases as an approach to cancer chemotherapy: progression from reversible to irreversible inhibitors. *Pharmacol. Ther.* 1999, 82: 207-218.
13. Fry D W, Bridges A J, Denny W A, Doherty A, Greis K D, Hicks J L, Hook K E, Keller P R, Leopold W R, Loo J A; Specific irreversible inactivation of the epidermal growth factor receptor and erbB2, by a new class of tyrosine kinase inhibitor. *Proc. Natl. Acad. Science.* 1998; 95: 12022-12027.
14. Smaill J B, Rewcastle G W, Loo J A, Greis K D, Chan O H, Reyner E L, Lipka L, Showalter H D, Vincent P W, Elliott W L; Tyrosine kinase inhibitors; Irreversible inhibitors of the epidermal growth factor receptor: 4-(phenylamino)quinazoline and 4-(phenylamino)pyrido[3,2-d]pyrimidine-6-acrylamide bearing additional solubilizing functions. *J Med Chem.* 2000; 43: 1380-1397.
15. Discafani, C M, Carroll, M, Floyd, M B, Hollander, J; Irreversible inhibition of epidermal growth factor tyrosine kinase with in vitro activity by N-[4-[(3-bromophenylamino]-6-quinazolinyl]-2-butynamide (CL-397785). *Biochem. Pharmacol.* 1999, 57, 917-925.
16. Tsou, H R, Mamuya, N; 6-substituted-4-(3-bromophenylamino)quinazolines as putative irreversible inhibitors of the epidermal growth factor receptor (EGFR) and human epidermal growth factor receptor (HER-2). *J. Med. Chem.* 2001; 44, 2719-2734.
17. Sirotnak F M, Zakowski M F, Miller V A, Scher H I, Kris M G; Efficacy of cytotoxic agents against human tumor xenografts is markedly enhanced by co-administration of ZD1839 (Iressa), an inhibitor of EGFR tyrosine kinase. *Clin. Cancer Res.* 2000; 6: 4885-4892.
18. Sirotnak F M, She Y, Lee F, Chen J, Scher H I; Studies with CWR22 xenograft in nude mice suggest that ZD1839 may have a role in the treatment of both androgen-dependent and androgen-independent human prostate cancer. *Clin. Cancer Res.* 2002; 8: 3870-3876.
19. Brahimi F, Matheson S L, McNamee J P, Tari A, Jean-Claude, B J; Inhibition of epidermal growth factor receptor-mediated signalling by "combi-triazene" BJ2000, a new probe for the Combi-Targeting postulates. *J. Pharm. Exp. Ther.* 2002; 303: 238-246.
20. Matheson S L, McNamee J P, Jean-Claude B J; Design of a chimeric 3-methyl-1,2,3-triazene with mixed receptor tyrosine kinase and DNA damaging properties: a novel tumour targeting strategy. *J. Pharm. Exp. Ther.* 2001; 296: 832-840.
21. Qiu Q, Dudouit F, Matheson S L, Brahimi F, Banerjee R, Mcnamee J P, Jean-Claude B J; The combi-targeting concept: a novel 3,3-disubstitued nitrosourea with EGFR tyrosine kinase inhibitory properties. *Cancer Chemother. Pharmacol.* 2003; 51: 1-10.
22. Rachid Z, Brahimi F, Teoh N, Katsoulas A, Jean-Claude B J; Chemical Dissection of the binary properties of a series of combi-triazenes. *J. Med. Chem.* 2003, 46: 4313-4321.
23. Tari A M, Lopez-Berestein G; Serum predominantly activates MAPK and akt kinases in EGFR- and ErbB2-overexpressing cells, respectively. *Int. J. Cancer,* 2000; 86: 295-297.
24. Skehan P, Storeng R, Scudiero D, Monks A, McMahon J, Vistica D, Warren J T, Bokesch H, Kenney S, Boyd M R; New colorimetric cytotoxicity assay for anti-cancer drug screening. *J. Natl. Cancer Inst.* 1990; 82: 1107-1112.
25. Martin S J, Finucane D M, Amarante-Mendes G P, O'Brien G A, Green D R; Phosphatidylserine externalization during CD95-induced apoptosis of cells and cytoplasts requires ICE/CED-3 protease activity. *J. Biol. Chem.* 1996; 271:28753-6.
26. Davis R J; The mitogen-activated protein kinase signal transduction pathway. *J. Biol. Chem.* 1993; 268:14553-14556.
27. Davis R J; Transcriptional regulation by MAP kinases. *Mol. Reprod. Dev.* 1995; 42: 459-67.
28. Mabuchi S, Ohmichi M, Kimura A, Hisamoto K, Hayakawa J, Nishio Y, Adachi K, Takahashi K, Arimoto-Ishida E, Nakatsuji Y, Tasaka K, Murata Y; Inhibition of phosphorylation of BAD and Raf-1 by Akt sensitizes human ovarian cancer cells to paclitaxel. *J Biol Chem.* 2002; 277: 33490-500.
29. Yacoub A, McKinstry R, Hinman D, Chung T, Dent P, Hagan M P; Epidermal growth factor and ionizing radiation up-regulates the DNA repair genes XRCC1 and ERCC1 in DU145 and LNCaP prostate carcinoma through MAPK signaling. *Radiation Res.* 2003; 159: 439-452.

30. Vaughan K, Manning H. W; Open chain nitrogen compounds. Part XIII. 1-Aryl-3-arylthiomethyltriazenes and 3-(arylazo)-1,3-thiazolidines. *Can. J. Chem.*, 66 :2487-2491, 1988.
31. Zakaria Rachid, Fouad Brahimi, Juozas Domarkas, Bertrand Jacques Jean-Claude. Synthesis of half-mustard combi-molecules with fluorescence properties: correlation with EGFR status, Bioorg. Med Chem. Lett., accepted.
32. Brock R, Hamelers I H, Jovin T M. Comparison of fixation protocols for adherent cultured cells applied to a GFP fusion protein of the epidermal growth factor receptor. Cytometry 1999; 35:353-62.
33. Brahimi F, Zakaria R, Qiu Q, McNamee J P, Li Y J, Tari A, Jean-Claude B J. Multiple mechanisms of action of ZR2002 in human breast cancer cells: A novel combi-molecule designed to block signalling mediated by the erb family of oncogenes and to damage genomic DNA. Int. J Cancer 2004; 112: 484-91.

What is claimed is:

1. A combi-molecule of Formula I, or a pharmaceutically acceptable salt thereof:

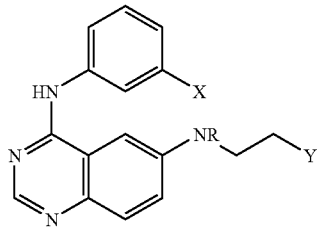

Formula I wherein:
a) R is selected from the group consisting of: H, Me, and 2-chloroethyl;
b) X is selected from the group consisting of Cl, Br, I, H and Me; and
c) Y is selected from the group consisting of Cl, Br, I, OTs, and OMs.

2. A combi-molecule as defined in claim 1, wherein R is H, X is Br, and Y is Cl.

3. A pharmaceutical composition comprising a combi-molecule as defined in claim 1 and at least one pharmaceutically acceptable carrier.

4. A pharmaceutical composition comprising a combi-molecule as defined in claim 2 and at least one pharmaceutically acceptable carrier.

5. A combi-molecule as defined in claim 1, wherein R is H, X is Cl, and Y is Cl.

6. A pharmaceutical composition comprising a combi-molecule as defined in claim 5 and at least one pharmaceutically acceptable carrier.

* * * * *